US012129476B2

United States Patent
Drouin et al.

(10) Patent No.: US 12,129,476 B2
(45) Date of Patent: Oct. 29, 2024

(54) METHODS FOR MEASURING THE POTENCY OF AADC VIRAL VECTORS

(71) Applicant: VOYAGER THERAPEUTICS, INC., Cambridge, MA (US)

(72) Inventors: Lauren M. Drouin, Cambridge, MA (US); Patrick Starremans, Cambridge, MA (US); Eric D. Horowitz, Norwell, MA (US); Carlo Ciatto, Brookline, MA (US); Joseph Mombeleur, Bridgewater, MA (US)

(73) Assignee: Voyager Therapeutics, Inc., Cambridge, MA (US)

( * ) Notice: Subject to any disclaimer, the term of this patent is extended or adjusted under 35 U.S.C. 154(b) by 978 days.

(21) Appl. No.: 17/050,703

(22) PCT Filed: Apr. 26, 2019

(86) PCT No.: PCT/US2019/029297
§ 371 (c)(1),
(2) Date: Oct. 26, 2020

(87) PCT Pub. No.: WO2019/210137
PCT Pub. Date: Oct. 31, 2019

(65) Prior Publication Data
US 2021/0238630 A1    Aug. 5, 2021

Related U.S. Application Data

(60) Provisional application No. 62/663,958, filed on Apr. 27, 2018, provisional application No. 62/703,590, filed on Jul. 26, 2018, provisional application No. 62/741,463, filed on Oct. 4, 2018.

(51) Int. Cl.
C12N 15/86       (2006.01)
A61K 48/00       (2006.01)
G01N 30/02       (2006.01)

(52) U.S. Cl.
CPC ............ *C12N 15/86* (2013.01); *A61K 48/005* (2013.01); *C12N 2750/14143* (2013.01); *G01N 2030/027* (2013.01)

(58) Field of Classification Search
CPC .......... C12N 15/86; C12N 2750/14143; A61K 48/005; G01N 2030/027; G01N 33/9413
See application file for complete search history.

(56) References Cited

FOREIGN PATENT DOCUMENTS

WO    WO-2016073693 A2 *    5/2016    ............. A61K 35/76

OTHER PUBLICATIONS

San Sebastian W et al: "Safety and tolerability of MRI-guided infusion of AAV2-hAADC into the mid-brain of nonhuman primate", Molecular Therapy—Methods & Clinical Develop, vol. 1, Oct. 15, 2014 (Oct. 15, 2014), p. 14049.
Ciesielska A et al: "Carbidopa-Based Modulation of the Functional Effect of the AAV2-hAADC Gene Therapy in 6-OHDA Lesioned Rats", PLOS ONE, vol. 10, No. 4, Apr. 10, 2015 (Apr. 10, 2015), p. e0122708, XP055606510.
Leff S E et al: "Long-term Restoration of Striatal L-Aromatic Amino Acid Decarboxylase Activity using Recombinant Adeno-Associated Viral Vector Gene Transfer in a Rodent Model of Parkinson's Disease", Neuroscience, New York, NY, US, vol. 92, No. 1, May 20, 1999 (May 20, 1999), pp. 185-196.
Duan C L et al: "The assays of activities and function of TH, AADC, and GCH1 and their potential use in ex vivo gene therapy of PD", Brain Research Protocols, Elsevier, Amsterdam, NL, vol. 16, No. 103, Dec. 1, 2005 (Dec. 1, 2005), pp. 37-43.
Dorange F et al: "Analytical approaches to characterize AAV vector production & purification: Advances and challenges", Cell and Gene Therapy Insights, vol. 4, No. 2, Mar. 14, 2018 (Mar. 14, 2018), pp. 119-129.
International Search Report & Written Opinion issued Feb. 15, 2019 in co-pending application No. PCT/US2018/045088, entitled Compositions and Methods for Delivery of AAV.

* cited by examiner

*Primary Examiner* — Paul J Holland
(74) *Attorney, Agent, or Firm* — McCarter & English, LLP; Maria Laccotripe Zacharakis; Yu Lu

(57) ABSTRACT

The present disclosure presents improved analytical tools, systems and methods related to AADC viral vectors, including AADC potency assays for measuring and analyzing AADC expression potency (i.e. enzymatic activity) related to AADC vectors such as adeno-associated virus (AAV) AADC vectors.

20 Claims, 6 Drawing Sheets
Specification includes a Sequence Listing.

SEQUENCE LISTING

<160> NUMBER OF SEQ ID NOS: 14

<210> SEQ ID NO 1
<211> LENGTH: 480
<212> TYPE: PRT
<213> ORGANISM: Homo sapiens

<400> SEQUENCE: 1

```
Met Asn Ala Ser Glu Phe Arg Arg Arg Gly Lys Glu Met Val Asp Tyr
1               5                   10                  15

Val Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Ala Pro Gln
        35                  40                  45

Glu Pro Asp Thr Phe Glu Asp Ile Ile Asn Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
        115                 120                 125

Pro Lys Ala Phe Leu Asn Glu Lys Ala Gly Glu Gly Gly Gly Val Ile
    130                 135                 140

Gln Gly Ser Ala Ser Glu Ala Thr Leu Val Ala Leu Leu Ala Ala Arg
145                 150                 155                 160
```

```
Thr Lys Val Ile His Arg Leu Gln Ala Ala Ser Pro Glu Leu Thr Gln
            165                 170                 175
Ala Ala Ile Met Glu Lys Leu Val Ala Tyr Ser Ser Asp Gln Ala His
        180                 185                 190
Ser Ser Val Glu Arg Ala Gly Leu Ile Gly Gly Val Lys Leu Lys Ala
    195                 200                 205
Ile Pro Ser Asp Gly Asn Phe Ala Met Arg Ala Ser Ala Leu Gln Glu
210                 215                 220
Ala Leu Glu Arg Asp Lys Ala Ala Gly Leu Ile Pro Phe Phe Met Val
225                 230                 235                 240
Ala Thr Leu Gly Thr Thr Thr Cys Cys Ser Phe Asp Asn Leu Leu Glu
                245                 250                 255
Val Gly Pro Ile Cys Asn Lys Glu Asp Ile Trp Leu His Val Asp Ala
            260                 265                 270
Ala Tyr Ala Gly Ser Ala Phe Ile Cys Pro Glu Phe Arg His Leu Leu
        275                 280                 285
Asn Gly Val Glu Phe Ala Asp Ser Phe Asn Phe Asn Pro His Lys Trp
    290                 295                 300
Leu Leu Val Asn Phe Asp Cys Ser Ala Met Trp Val Lys Lys Arg Thr
305                 310                 315                 320
Asp Leu Thr Gly Ala Phe Arg Leu Asp Pro Thr Tyr Leu Lys His Ser
                325                 330                 335
His Gln Asp Ser Gly Leu Ile Thr Asp Tyr Arg His Trp Gln Ile Pro
            340                 345                 350
Leu Gly Arg Arg Phe Arg Ser Leu Lys Met Trp Phe Val Phe Arg Met
        355                 360                 365
Tyr Gly Val Lys Gly Leu Gln Ala Tyr Ile Arg Lys His Val Gln Leu
    370                 375                 380
Ser His Glu Phe Glu Ser Leu Val Arg Gln Asp Pro Arg Phe Glu Ile
385                 390                 395                 400
Cys Val Glu Val Ile Leu Gly Leu Val Cys Phe Arg Leu Lys Gly Ser
                405                 410                 415
Asn Lys Val Asn Glu Ala Leu Leu Gln Arg Ile Asn Ser Ala Lys Lys
            420                 425                 430
Ile His Leu Val Pro Cys His Leu Arg Asp Lys Phe Val Leu Arg Phe
        435                 440                 445
Ala Ile Cys Ser Arg Thr Val Glu Ser Ala His Val Gln Arg Ala Trp
    450                 455                 460
Glu His Ile Lys Glu Leu Ala Ala Asp Val Leu Arg Ala Glu Arg Glu
465                 470                 475                 480

<210> SEQ ID NO 2
<211> LENGTH: 3526
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgtagttaa tgattaaccc gccatgctac ttatctacgt     180
agccatgcgt cgacataacg cgtatatcta gacgttacat aacttacggt aaatggcccg     240
```

```
cctggctgac cgcccaacga cccccgccca ttgacgtcaa taatgacgta tgttcccata    300
gtaacgccaa tagggacttt ccattgacgt caatgggtgg agtatttacg gtaaactgcc    360
cacttggcag tacatcaagt gtatcatatg ccaagtacgc cccctattga cgtcaatgac    420
ggtaaatggc ccgcctggca ttatgcccag tacatgacct tatgggactt tcctacttgg    480
cagtacatct agtattagtc atcgctatta ccatggtgat gcggttttgg cagtacatca    540
atgggcgtgg atagcggttt gactcacggg gatttccaag tctccacccc attgacgtca    600
atgggagttt gttttggcac caaaatcaac gggactttcc aaaatgtcgt aacaactccg    660
ccccattgac gcaaatgggc ggtaggcgtg tacggtggga ggtctatata agcagagctc    720
gtttagtgaa ccgtcagatc gcctggagac gccatccacg ctgttttgac ctccatagaa    780
gacaccggga ccgatccagc ctccgcggat tcgaatcccg gccggaacg gtgcattgga     840
acgcggattc cccgtgccaa gagtgacgta agtaccgcct atagagtcta taggcccaca    900
aaaaatgctt tcttctttta atatactttt ttgtttatct tatttctaat actttcccta    960
atctctttct ttcagggcaa taatgataca atgtatcatg cctctcttgca ccattctaaa   1020
gaataacagt gataatttct gggttaaggc aatagcaata tttctgcata taaatatttc    1080
tgcatataaa ttgtaactga tgtaagaggt ttcatattgc taatagcagc tacaatccag    1140
ctaccattct gcttttattt tatggttggg ataaggctgg attattctga gtccaagcta    1200
ggccccttttg ctaatcatgt tcatacctct tatcttcctc ccacagctcc tgggcaacgt    1260
gctggtctgt gtgctggccc atcactttgg caaagaattg ggattcgaac atcgattgaa    1320
ttccccgggg atccaccatg aacgcaagtg aattccgaag gagagggaag gagatggtgg    1380
attacgtggc caactacatg gaaggcattg agggacgcca ggtctaccct gacgtggagc    1440
ccgggtacct gcggccgctg atccctgccg ctgcccctca ggagccagac acgtttgagg    1500
acatcatcaa cgacgttgag aagataatca tgcctggggt gacgcactgg cacagcccct    1560
acttcttcgc ctacttcccc actgccagct cgtacccggc catgcttgcg gacatgctgt    1620
gcggggccat ggctgcatc ggcttctcct gggcggcaag cccagcatgc acagagctgg     1680
agactgtgat gatggactgg ctcgggaaga tgctggaact accaaaggca ttttgaatg    1740
agaaagctgg agaaggggga ggagtgatcc agggaagtgc cagtgaagcc accctggtgg    1800
ccctgctggc cgctcggacc aaagtgatcc atcggctgca ggcagcgtcc ccagagctca    1860
cacaggccgc tatcatggag aagctggtgg cttactcatc cgatcaggca cactcctcag    1920
tggaaagagc tgggttaatt ggtggagtga aattaaaagc catcccctca gatggcaact    1980
tcgccatgcg tgcgtctgcc ctgcaggaag ccctggagag agacaaagcg gctggcctga    2040
ttcctttctt tatggttgcc accctgggga ccacaacatg ctgctccttt gacaatctct    2100
tagaagtcgg tcctatctgc aacaaggaag acatatggct gcacgttgat gcagcctacg    2160
caggcagtgc attcatctgc cctgagttcc ggcaccttct gaatgagtg gagtttgcag     2220
attcattcaa ctttaatccc cacaaatggc tattggtgaa ttttgactgt tctgccatgt    2280
gggtgaaaaa gagaacagac ttaacgggag cctttagact ggaccccact tacctgaagc    2340
acagccatca ggattcaggg cttatcactg actaccggca ttggcagata ccactgggca    2400
gaagatttcg ctctttgaaa atgtggtttg tatttaggat gtatggagtc aaaggactgc    2460
aggcttatat ccgcaagcat gtccagctgt cccatgagtt tgagtcactg gtgcgccagg    2520
atcccccgct tgaaatctgt gtggaagtca ttctggggct tgtctgcttt cggctaaagg    2580
gttccaacaa agtgaatgaa gctcttctgc aaagaataaa cagtgccaaa aaaatccact    2640
```

```
tggttccatg tcacctcagg gacaagtttg tcctgcgctt tgccatctgt tctcgcacgg    2700
tggaatctgc ccatgtgcag cgggcctggg aacacatcaa agagctggcg gccgacgtgc    2760
tgcgagcaga gagggagtag gagtgaagcc aggacctgca gaagcttgcc tcgagcagcg    2820
ctgctcgaga gatctacggg tggcatccct gtgacccctc cccagtgcct ctcctggccc    2880
tggaagttgc cactccagtg cccaccagcc ttgtcctaat aaaattaagt tgcatcattt    2940
tgtctgacta ggtgtccttc tataatatta tggggtggag ggggtggta tggagcaagg     3000 ggcaagttgg gaagacaacc tgtagggcct gcggggtcta ttgggaacca agctggagtg    3060
cagtggcaca atcttggctc actgcaatct ccgcctcctg ggttcaagcg attctcctgc    3120
ctcagcctcc cgagttgttg ggattccagg catgcatgac caggctcagc taattttgt    3180 tttttggta gagacggggt ttcaccatat tggccaggct ggtctccaac tcctaatctc     3240
aggtgatcta cccaccttgg cctcccaaat tgctggatt acaggcgtga accactgctc     3300
ccttccctgt ccttactaga tttaaatatg tcgtgcatcg atgctacgta gataagtagc    3360
atggcgggtt aatcattaac tacagaggaa cccctagtga tggagttggc cactccctct    3420
ctgcgcgctc gctcgctcac tgaggccggg cgaccaaagg tcgcccgacg cccgggcttt    3480
gcccgggcgg cctcagtgag cgagcgagcg cgcagctgcc tgcagg                   3526
```

<210> SEQ ID NO 3
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 3

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc t                                             141
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 4

```
gtcgacataa cgcgtata                                                   18
```

<210> SEQ ID NO 5
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 5

```
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
```

```
catgaccttta tgggactttc ctacttggca gtacatctag tattagtcat cgctattacc    300
atg                                                                  303

<210> SEQ ID NO 6
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gtgatgcggt tttggcagta catcaatggg cgtggatagc ggtttgactc acggggattt     60
ccaagtctcc accccattga cgtcaatggg agtttgtttt ggcaccaaaa tcaacgggac    120
tttccaaaat gtcgtaacaa ctccgcccca ttgacgcaaa tgggcggtag gcgtgtacgg    180
tgggaggtct atataagcag agct                                           204

<210> SEQ ID NO 7
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tcagatcgcc tggagacgcc atccacgctg ttttgacctc catagaagac accgggaccg     60
atccagcctc cgcggattcg aatcccggcc gggaacggtg cattggaacg cggattcccc    120
gtgccaagag tgac                                                      134

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaagtaccg cctatagagt ctataggccc ac                                   32

<210> SEQ ID NO 9
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
aaaaaatgct tcttcttttt aatatacttt tttgtttatc ttatttctaa tactttccct     60
aatctctttc tttcagggca ataatgatac aatgtatcat gcctctttgc accattctaa    120
agaataacag tgataatttc tgggttaagg caatagcaat atttctgcat ataaatattt    180
ctgcatataa attgtaactg atgtaagagg tttcatattg ctaatagcag ctacaatcca    240
gctaccattc tgctttatt ttatggttgg gataaggctg gattattctg agtccaagct    300 aggcccttt gctaatcatg ttcataccte ttatcttcct cccacag                  347

<210> SEQ ID NO 10
```

```
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctcctgggca acgtgctggt ctgtgtgctg gcccatcact ttggcaaaga att         53

<210> SEQ ID NO 11
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgaacgcaa gtgaattccg aaggagaggg aaggagatgg tggattacgt ggccaactac    60
atggaaggca ttgagggacg ccaggtctac cctgacgtgg agcccgggta cctgcggccg   120
ctgatccctg ccgctgcccc tcaggagcca gacacgtttg aggacatcat caacgacgtt   180
gagaagataa tcatgcctgg ggtgacgcac tggcacagcc cctacttctt cgcctacttc   240
cccactgcca gctcgtaccc ggccatgctt gcggacatgc tgtgcggggc cattggctgc   300
atcggcttct cctgggcggc aagcccagca tgcacagagc tggagactgt gatgatggac   360
tggctcggga agatgctgga actaccaaag gcattttga atgagaaagc tggagaaggg   420
ggaggagtga tccagggaag tgccagtgaa gccaccctgg tggccctgct ggccgctcgg   480
accaaagtga tccatcggct gcaggcagcg tccccagagc tcacacaggc cgctatcatg   540
gagaagctgt ggcttactc atccgatcag gcacactcct cagtgaaaag agctgggtta   600
attggtggag tgaaattaaa agccatcccc tcagatggca acttcgccat gcgtgcgtct   660
gccctgcagg aagccctgga gagagacaaa gcggctggcc tgattccttt ctttatggtt   720
gccaccctgg ggaccacaac atgctgctcc tttgacaatc tcttagaagt cggtcctatc   780
tgcaacaagg aagacatatg gctgcacgtt gatgcagcct acgcaggcag tgcattcatc   840
tgccctgagt ccggcaccct tctgaatgga gtggagtttg cagattcatt caactttaat   900
ccccacaaat ggctattggt gaattttgac tgttctgcca tgtgggtgaa aaagagaaca   960
gacttaacgg gagcctttag actggacccc acttacctga agcacagcca tcaggattca  1020
gggcttatca ctgactaccg gcattggcag ataccactgg gcagaagatt tcgctctttg  1080
aaaatgtggt ttgtatttag gatgtatgga gtcaaaggac tgcaggctta tatccgcaag  1140
catgtccagc tgtcccatga gtttgagtca ctggtgcgcc aggatccccg ctttgaaatc  1200
tgtgtggaag tcattctggg gcttgtctgc tttcggctaa agggttccaa caaagtgaat  1260
gaagctcttc tgcaaagaat aaacagtgcc aaaaaaatcc acttggttcc atgtcacctc  1320
agggacaagt ttgtcctgcg ctttgccatc tgttctcgca cggtggaatc tgcccatgtg  1380
cagcgggcct gggaacacat caaagagctg gcggccgacg tgctgcgagc agagagggag  1440

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 12
gctgctcgag agatctac                                                    18

<210> SEQ ID NO 13
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gggtggcatc cctgtgaccc ctccccagtg cctctcctgg ccctggaagt tgccactcca      60
gtgcccacca gccttgtcct aataaaatta agttgcatca ttttgtctga ctaggtgtcc     120
ttctataata ttatggggtg gagggggtg gtatggagca aggggcaagt tgggaagaca      180
acctgtaggg cctgcggggt ctattgggaa ccaagctgga gtgcagtggc acaatcttgg    240
ctcactgcaa tctccgcctc ctgggttcaa gcgattctcc tgcctcagcc tcccgagttg    300
ttgggattcc aggcatgcat gaccaggctc agctaatttt tgttttttg gtagagacgg     360 ggtttcacca tattggccag gctggtctcc aactcctaat ctcaggtgat ctacccacct    420
tggcctccca aattgctggg attacaggcg tgaaccactg ctcccttccc tgtcctt       477

<210> SEQ ID NO 14
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcctgcag g                                              141
```

METHODS FOR MEASURING THE POTENCY OF AADC VIRAL VECTORS

CROSS REFERENCE TO RELATED APPLICATIONS

This application is a 35 U.S.C. § 371 U.S. National Stage Entry of International Application No. PCT/US2019/029297, filed Apr. 26, 2019; which claims the benefit of U.S. Provisional Patent Application No. 62/663,958, filed Apr. 27, 2018, and U.S. Provisional Patent Application No. 62/703,590, filed Jul. 26, 2018, and U.S. 62/741,463, filed Oct. 4, 2018; the contents of which are each incorporated herein by reference in their entirety.

REFERENCE TO SEQUENCE LISTING

The present application is being filed along with a Sequence Listing in electronic format. The Sequence Listing is provided as a file entitled 20571058US371_SL.txt, created on Oct. 26, 2020, which is 15,952 bytes in size. The information in the electronic format of the sequence listing is incorporated herein by reference in its entirety.

FIELD OF THE DISCLOSURE

The present disclosure presents improved analytical tools, systems and methods related to AADC viral vectors, including AADC potency assays for measuring and analyzing AADC expression and biological potency (i.e. enzymatic activity) related to AADC vectors such as adeno-associated virus (AAV) AADC vectors.

BACKGROUND

Parkinson's Disease

Aromatic L-amino acid decarboxylase (AADC) is a homodimeric pyridoxal phosphate-dependent enzyme responsible for the synthesis of dopamine and serotonin. The encoded protein catalyzes the decarboxylation of L-3,4-dihydroxyphenylalanine (L-DOPA or levodopa) to dopamine; L-5-hydroxytryptophan to serotonin; and L-tryptophan to tryptamine. Defects in this gene are the cause of aromatic L-amino-acid decarboxylase deficiency (AADCD), which is an inborn error in neurotransmitter metabolism leading to combined serotonin and catecholamine deficiency that results in severe motor and autonomic dysfunctions.

Parkinson's Disease (PD) is a progressive neurodegenerative disease of the central nervous system (CNS) producing sensory and motor symptoms. Dopamine replacement (i.e., levodopa) has been the standard pharmacotherapy for motor impairment in PD. However, the benefit of dopamine therapy becomes less marked over time, due, in part, to the progressive death of dopamine-generating cells and corresponding loss of AADC activity. Furthermore, systemic administration of high-dose dopamine is complicated by side effects, such as fluctuations in motor performance, dyskinesias, and hallucinations, resulting from dopaminergic stimulation of the mesolimbic system. One strategy to restore dopaminergic function and minimize side effects is the use of gene therapy to deliver AADC directly to a targeted region of the CNS.

The adeno-associated virus (AAV) has emerged as an attractive vector for gene therapy due to its long-term gene expression, the inability to autonomously replicate without a helpervirus, the ability to transduce dividing and non-dividing cells, and the lack of pathogenicity from wild-type infections (See e.g., Hadaczek et al. Mol. Ther. 18(8), 1458-1461, August 2010). AAV is a helper-dependent DNA parvovirus which belongs to the genus Dependovirus.

Adeno-Associated Virus (AAV)

AAVs have emerged as one of the most widely studied and utilized viral vectors for gene transfer to mammalian cells. See, e.g., Tratschin et al., *Mol. Cell Biol.*, 5(11):3251-3260 (1985) and Grimm et al., Hum. Gene Ther., 10(15): 2445-2450 (1999), the contents of which are herein incorporated by reference in their entirety.

Adeno-associated viral (AAV) vectors are promising candidates for therapeutic gene delivery and have proven safe and efficacious in clinical trials. The design and production of improved AAV particles for this purpose is an active field of study.

The Parvoviridae family of viruses consist of two subfamilies: Parvovirinae, which infect vertebrates, and Densovirinae, which infect invertebrates. The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are herein incorporated by reference in their entirety.

Dependoviruses include the viral family of the adeno-associated viruses (AAV) which are capable of replication in vertebrate hosts including, but not limited to, human, primate, bovine, canine, equine, and ovine species.

The AAV genome is a linear, single-stranded DNA (ssDNA) molecule approximately 5,000 nucleotides (nt) in length. Inverted terminal repeats (ITRs) flank the coding nucleotide sequences for the non-structural proteins (encoded by Rep genes) and the structural proteins (encoded by capsid genes or Cap genes). The AAV genome includes a characteristic T-shaped hairpin structure defined by the self-complementary terminal 145 nt of the 5' and 3 ends of the ssDNA which form an energetically stable double stranded region. The double stranded hairpin structures include multiple functions including, but not limited to, acting as an origin for DNA replication by functioning as primers for the endogenous DNA polymerase complex of the host viral production cell.

The Rep genes encode the non-structural proteins which regulate functions such as the replication of the AAV genome. Rep78 and Rep68 are generally transcribed from the p5 promoter, and Rep52 and Rep40 are generally transcribed from the p19 promoter.

The Cap gene encodes the structural proteins, VP1, VP2 and/or VP3 that assemble to form the viral capsid. The Cap genes are generally transcribed from the p40 promoter. The capsid proteins of the AAV are generally assembled in a tetrahedron form using 3 proteins (VP1, VP2 and VP3) expressed from one or more open reading frames (ORF).

SUMMARY

Current methods to determine expression of proteins including AADC, such as the AADC ELISA kit, measure the protein concentration, which is not a direct indicator of biological activity. Moreover, these methods can lead to variability among the sample replicates. Thus, there is a longfelt need for improved analytical tools for AADC viral vectors, including improved methods for measuring the potency of AADC viral vectors which offer consistency among various sample replicates.

The present disclosure provides improved analytical tools, systems and methods related to AADC viral vectors, including AADC potency assays for measuring and analyzing AADC expression and biological potency (i.e. enzymatic activity) related to AADC vectors such as adeno-associated virus (AAV) AADC vectors.

The present disclosure presents improved analytical tools, systems and methods, as well as improved combinations of analytical tools, systems and methods, related to AADC viral vectors. In certain embodiments, the analytical tools, systems and methods are AADC potency assays and methods for measuring AADC potency. In certain embodiments, the AADC potency assays measure potency of an AADC vector, for example, a viral vector, e.g., adeno-associated virus (AAV) vector. In certain embodiments, the AADC potency assays measure potency of an AADC vector, for example, a viral vector, e.g., AAV vector, based on AADC enzymatic activity.

In certain embodiments, provided herein is a method for measuring the potency of an AADC viral vector, comprising adding L-DOPA to a cell lysate produced from cells transduced with the viral vector comprising a polynucleotide encoding AADC and measuring the amount of dopamine produced in the cell lysate after addition of L-DOPA. In another embodiment, provided herein is a method for measuring the potency of an AADC AAV vector, comprising adding L-DOPA to a cell lysate produced from cells transduced with the AAV vector comprising a polynucleotide encoding AADC and measuring the amount of dopamine produced in the cell lysate after addition of L-DOPA. In certain embodiments, the AADC is human AADC. In certain embodiments, the AAV is AAV2.

Also provided herein is a method for determining the potency of an AADC viral vector, comprising adding L-DOPA to a cell lysate produced from cells transduced with a first viral vector comprising a polynucleotide encoding AADC, measuring the amount of dopamine produced in the cell lysate after addition of L-DOPA, and comparing the amount of dopamine produced to that produced when a viral vector reference standard is utilized, such that the relative potency of the first viral vector is determined. In certain embodiments, provided herein is a method for determining the potency of an AADC AAV vector, comprising adding L-DOPA to a cell lysate produced from cells transduced with a first AAV vector comprising a polynucleotide encoding AADC, measuring the amount of dopamine produced in the cell lysate after addition of L-DOPA, and comparing the amount of dopamine produced to that produced when an AAV vector reference standard is utilized, such that the relative potency of the first AAV vector is determined. In certain embodiments, the AADC is human AADC. In certain embodiments, the AAV is AAV2.

In some embodiments, the amount of dopamine produced by a viral, e.g., AAV, vector reference standard is determined by adding L-DOPA to a cell lysate produced from cells transduced with the viral, e.g., AAV, vector comprising a polynucleotide encoding AADC and measuring the amount of dopamine produced in the cell lysate after the addition of L-DOPA. In certain embodiments, the AADC is human AADC. In certain embodiments, the AAV is AAV2.

In some embodiments, the cells utilized in the assays and methods presented herein are mammalian cells. In certain embodiments, the cells are human cells. In specific embodiments, the cells are sarcoma cells. In other embodiments, the cells are fibrosarcoma cells. In certain embodiments, the cells are primary cells or primary cell cultures. In certain embodiments, the cells are cell lines. In specific embodiments, the cells are HT1080 cells.

In some embodiments, the cells are plated at a density of $1\times10^2$ cells/well to $1\times10^6$ cells/well. In specific embodiments, the cells are plated at a density of $1\times10^3$ cells/well to $1\times10^6$ cells/well. In some embodiments, the cells are plated at a density of $1\times10^3$ cells/well to $1\times10^5$ cells/well. In specific embodiments, the cells are plated at a density of $1-9\times10^4$ cells/well. In specific embodiments, the cells are plated at a density of $1-5\times10^4$ cells/well. In specific embodiments, the cells are plated at a density of $1\times10^4$ cells/well.

In certain embodiments, for example, when multiple plate formats are utilized, the density of plated cells can be adjusted on a per $cm^2$ basis. In certain embodiments, cells are plated at a density of about $3\times10^2$ cells/$cm^2$ to about $3\times10^8$ cells/$cm^2$, for example, about $3\times10^2$ cells/$cm^2$ to about $3\times10^5$ cells/$cm^2$, or about $3\times10^3$ cells/$cm^2$ to about $3\times10^6$ cells/$cm^2$.

In certain embodiments, the AADC viral vector is transduced into the cells at a concentration of about 1 vg/cell to about $1\times10^8$ vg/cell. In some embodiments, the AADC viral vector is transduced into the cells at a concentration of about 10 vg/cell to about $1\times10^5$ vg/cell.

In some embodiments, the cells are harvested after 44-52 hours post transduction. In some embodiments, the AADC viral vector is transduced into the cells at a concentration of $1\times10^6$ vg/µL–$1\times10^{11}$ vg/µL. In some embodiments, the AADC viral vector is transduced into the cells at a concentration of $5\times10^6$ vg/µL–$5\times10^{10}$ vg/µL. In some embodiments, the AADC viral vector is transduced into the cells at a concentration of $1\times10^7$ vg/µL–$1\times10^{10}$ vg/µL. In some embodiments, the AADC viral vector is transduced into the cells at a concentration of $2\times10^7$ vg/µL–$2\times10^{10}$ vg/L. In some embodiments, the AADC AAV vector is transduced into the cells at a concentration of $1\times10^6$ vg/µL–$1\times10^{11}$ vg/µL. In some embodiments, the AADC AAV vector is transduced into the cells at a concentration of $5\times10^6$ vg/µL–$5\times10^{10}$ vg/µL. In some embodiments, the AADC AAV vector is transduced into the cells at a concentration of $1\times10^7$ vg/µL–$1\times10^{10}$ vg/µL. In some embodiments, the AADC AAV vector is transduced into the cells at a concentration of $2\times10^7$ vg/µL–$2\times10^{10}$ vg/µL.

In some embodiments, the cells from which cell lysates are made are harvested after 18-72 hours post transduction. In some embodiments, the cells are harvested after 24 hours post transduction. In some embodiments, the cells are harvested after 36 hours post transduction. In some embodiments, the cells are harvested after 48 hours post transduction.

In some embodiments, the cell lysate is formed from cells that are lysed using chemical and/or mechanical lysis. In some embodiments, the chemical lysis comprises use of a lysis buffer comprising a protease inhibitor, a buffer, for example, phosphate buffer saline, and a surfactant, for example, a non-ionic surfactant, e.g., Triton X100. In some embodiments, the lysis process involves cell centrifugation to clear the lysate and remove debris, for example, centrifugation at 3750 RPM (revolutions per minute) for 10 minutes at room temperature.

In some embodiments, an AADC reaction buffer is added to the cell lysate with the L-DOPA. In certain embodiments, the AADC reaction buffer comprises a buffer, for example, phosphate buffer, such as sodium phosphate buffer, e.g., 50 mM sodium phosphate buffer. In some embodiments, the AADC reaction buffer comprises 50 mM sodium phosphate buffer, ascorbic acid, pyridoxal-5'-phosphate DL-dithiothreitol, EDTA, and pargyline. In some embodiments, the AADC reaction buffer comprises a 50 mM sodium phosphate buffer, pH 7.2, 0.1 mM ascorbic acid, 0.1 mM pyridoxal-5'-phosphate, 1 mM DL-dithiothreitol, 0.1 mM EDTA, and 0.1 mM pargyline. In some embodiments, the AADC reaction buffer comprises octanesulfonic acid sodium salt, sodium phosphate monobasic, and acetonitrile. In some embodiments, the AADC reaction buffer comprises 3.0 mM, 3.2 mM or 3.5 mM octanesulfonic acid sodium salt, pH 3.0, 72.5 mM sodium phosphate monobasic (NaH2PO4), and 10% acetonitrile. In some embodiments, the AADC reaction buffer comprises 3.0-4.0 mM, 3.0-3.7 mM, 3.0-3.5 mM, 3.0-3.2 mM, 3.0 mM, 3.1 mM, 3.2 mM, 3.3 mM, 3.4 mM, 3.5 mM, 3.6 mM, 3.7 mM, 3.8 mM, 3.9 mM, or 4.0 mM.

In some embodiments, the concentration of L-DOPA added to the cell lysate is 0.1 mM to 100 mM. In certain embodiments, the concentration of L-DOPA added to the cell lysate is 0.1 mM to 50 mM. In certain embodiments, the concentration of L-DOPA added to the cell lysate is 0.1 mM to 1 mM. In certain embodiments, the concentration of L-DOPA added to the cell lysate is 5 mM to 30 mM. In some embodiments, the concentration of L-DOPA added to the cell lysate is 0.3 mM. In some embodiments, the concentration of L-DOPA added to the cell lysate is 20 mM.

In some embodiments, the AADC reaction with L-DOPA is carried out at 37° C. In some embodiments, the AADC reaction with L-DOPA is carried out for about 10-120 minutes. In some embodiments, the AADC reaction with L-DOPA is carried out for about 10-90 minutes. In some embodiments, the AADC reaction with L-DOPA is carried out for about 20-60 minutes. In some embodiments, the AADC reaction with L-DOPA is carried out for about 30±1-3 minutes. In specific embodiments, the AADC reaction with L-DOPA is carried out at 37° C. for about 30±1–3 minutes.

In some embodiments, the AADC reaction with L-DOPA is quenched with perchloric acid, for example, by adding ice-cold perchloric acid. In some embodiments, the perchloric acid, for example, ice-cold perchloric acid, is added at a concentration of 0.1 M to 1 M. In some embodiments, the perchloric acid, for example, ice-cold perchloric acid, is added at a concentration of 0.5 M.

In some embodiments, the amount of dopamine produced is measured using chromatography, for example, liquid chromatography such as high-performance liquid chromatography. In certain embodiments, the amount of dopamine produced is measured using Ultra High-Performance Liquid Chromatography with an Electrochemical Detector ("UHPLC-ECD"). In some embodiments, the amount of dopamine produced is measured using UHPLC-ECD by comparing the amount of dopamine to a dopamine standard curve. In certain embodiments, the amount of dopamine produced is measured using Ultra High-Performance Liquid Chromatography with an Ultraviolet Detector ("UHPLC-UV"). In some embodiments, the amount of dopamine produced is measured using UHPLC-UV by comparing the amount of dopamine to a dopamine standard curve.

DETAILED DESCRIPTION

Figure 1:
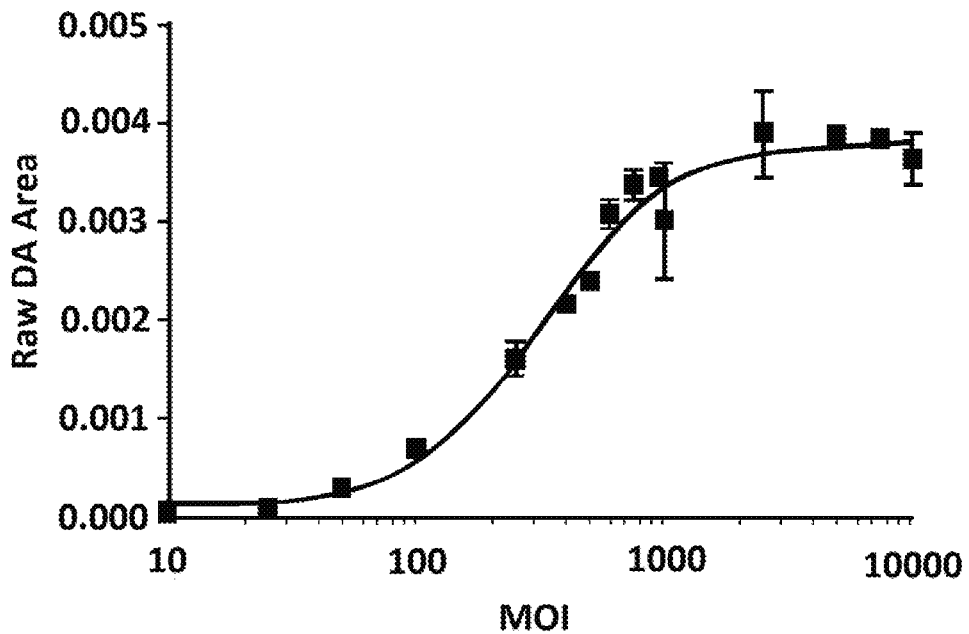
FIG. 1 shows the in vitro dose response curve to the transduction of HT1080 cells with AAV2.AADC vector.

The present application provides methods to measure a viral vector's potency. In some embodiments, the viral vector comprises a polynucleotide encoding a molecule of interest. In some embodiments, the present application provides methods to measure a viral vector's potency, wherein the viral vector comprises a polynucleotide encoding a molecule of interest, based on the activity of the molecule of interest.

In some embodiments of the methods, the viral vector comprises a polynucleotide encoding a protein of interest, based on the enzymatic activity of the protein of interest. In some embodiments, the protein of interest is AADC. In some embodiments, the present application provides methods to measure the potency of AADC viral vectors based on AADC enzymatic activity.

I. Compositions

Adeno-Associated Viruses (AAVs) and AAV Particles

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

The Parvoviridae family comprises the Dependovirus genus which includes adeno-associated viruses (AAV) capable of replication in vertebrate hosts including, but not limited to, human, primate, bovine, canine, equine, and ovine species.

The vector genome is a linear, single-stranded DNA (ssDNA) molecule approximately 5,000 nucleotides (nt) in length. The AAV viral genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV viral genome typically comprises two ITR sequences. The vector genome comprises a characteristic T-shaped hairpin structure defined by the self-complementary terminal 145 nt of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In addition to the encoded heterologous payload, AAV particles may comprise the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000), the contents of each of which are incorporated herein by reference in their entirety.

In one embodiment, AAV particles of the present disclosure are recombinant AAV particles which are replication defective, lacking sequences encoding functional Rep and Cap proteins within their viral genome. These defective AAV particles may lack most or all parental coding sequences and essentially carry only one or two AAV ITR sequences and the nucleic acid of interest for delivery to a cell, a tissue, an organ or an organism.

In one embodiment, the viral genome of the AAV particles of the present disclosure comprise at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present disclosure, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV particles of the present disclosure may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV particles (e.g., ssAAVs), the present disclosure also provides for self-complementary AAV (scAAVs) particles. scAAV particles contain DNA strands which anneal together to form double stranded DNA. By skipping second strand synthesis, ScAAVs allow for rapid expression in the cell.

In one embodiment, the AAV particle of the present disclosure is an scAAV.

In one embodiment, the AAV particle of the present disclosure is an ssAAV.

Methods for producing and/or modifying AAV particles are disclosed in the art such as pseudotyped AAV particles (PCT Patent Publication Nos. WO200028004; WO200123001; WO2004112727; WO 2005005610 and WO 2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In some embodiments the capsids of the AAV particles are engineered according to the methods described in US Publication Number US 20130195801, the contents of which are incorporated herein by reference in their entirety.

In one embodiment, the AAV particles comprising a payload region encoding the polypeptides of the disclosure may be introduced into mammalian cells.

Viral Genome Component: Inverted Terminal Repeats (ITRs)

The AAV particles of the present disclosure comprise a viral genome with at least one FIR region and a payload region. In one embodiment, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the disclosure may be comprised of naturally occurring polynucleotide sequences or recombinantly derived polynucleotide sequences.

The ITRs may be derived from the same serotype as the capsid. The ITR may be of a different serotype than the capsid. In one embodiment, the AAV particle has more than one ITR. In a non-limiting example, the AAV particle has a viral genome comprising two ITRs. In one embodiment, the ITRs are of the same serotype as one another. In another embodiment, the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment, the ITRs are 140-142 nucleotides in length. Non-limiting examples of ITR length are 102, 140, 141, 142, 145 nucleotides in length, and those having at least 95% identity thereto.

Viral Genome Component: Promoters

In one embodiment, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the disclosure in a target cell may require a specific promoter, including but not limited to, a promoter that is species specific, inducible, tissue-specific, or cell cycle-specific (Parr et al., Nat. Med. 3:1145-9 (1997): the contents of which are herein incorporated by reference in their entirety).

In one embodiment, the promoter is deemed to be efficient when it drives expression of the polypeptide(s) encoded in the payload region of the viral genome of the AAV particle. As a non-limiting example, that polypeptide is AADC.

In one embodiment, the promoter is a promoter deemed to be efficient when it drives expression in the cell being targeted.

In one embodiment, the promoter is a promoter having a tropism for the cell being targeted.

In one embodiment, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues.

In one embodiment, the promoter drives expression of the polypeptides of the disclosure for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US 20110212529, the contents of which are herein incorporated by reference in their entirety).

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In one embodiment, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 nucleotides. The promoter may have a length between 200-300, 200-400, 200-500, 200-600, 200-700, 200-800, 300400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300400, 300-500, 300-600, 300-700, 300-800, 400-500, 400-600, 400-700, 400-800, 500-600, 500-700, 500-800, 600-700, 600-800 or 700-800. In one embodiment, the promoter is a combination of a 382 nucleotide CMV-enhancer sequence and a 260 nucleotide CBA-promoter sequence.

In one embodiment, the viral genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EFIα, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HβH construct with a hGUSB promoter, a HSV-1 LAT promoter and an NSE promoter and found that the HβH construct showed weaker expression than NSE in mouse brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920-nucleotide promoter which are both absent in the liver but NFH is abundant in the sensory proprioceptive neurons, brain and spinal cord and NFH is present in the heart. SCN8A is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements in the promoter region of the sodium channel gene SCN8A*. Mamm Genome (2007) 18:723-731; and Raymond et al. *Expression of Alternatively Spliced Sodium Channel a-subunit genes*, Journal of Biological Chemistry (2004) 279(44) 46234-46241; the contents of each of which are herein incorporated by reference in their entireties).

Any of promoters taught by the aforementioned Yu, Soderblom, Gill, Husain, Passini, Xu, Drews or Raymond may be used in the present disclosures.

In one embodiment, the promoter is not cell specific.

In one embodiment, the promoter is an ubiquitin c (UBC) promoter. The UBC promoter may have a size of 300-350 nucleotides. As a non-limiting example, the UBC promoter is 332 nucleotides.

In one embodiment, the promoter is a β-glucuronidase (GUSB) promoter. The GUSB promoter may have a size of 350-400 nucleotides. As a non-limiting example, the GUSB promoter is 378 nucleotides.

In one embodiment, the promoter is a neurofilament light (NFL) promoter. The NFL promoter may have a size of 600-700 nucleotides. As a non-limiting example, the NFL promoter is 650 nucleotides.

In one embodiment, the promoter is a neurofilament heavy (NFH) promoter. The NFH promoter may have a size of 900-950 nucleotides. As a non-limiting example, the NFH promoter is 920 nucleotides.

In one embodiment, the promoter is a SCN8A promoter. The SCN8A promoter may have a size of 450-500 nucleotides. As a non-limiting example, the SCN8A promoter is 470 nucleotides.

In one embodiment, the promoter is a frataxin (FXN) promoter. The FXN promoter may also be referred to as the FRDA promoter.

In one embodiment, the promoter is a phosphoglycerate kinase 1 (PGK) promoter.

In one embodiment, the promoter is a chicken β-actin (CBA) promoter.

In one embodiment, the promoter is a cytomegalovirus (CMV) promoter.

In one embodiment, the promoter is a H1 promoter.

In one embodiment, the promoter is an engineered promoter.

In one embodiment, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12.

In one embodiment, the promoter is a RNA pol III promoter. As a non-limiting example, the RNA pol III promoter is U6. As a non-limiting example, the RNA pol III promoter is H1.

In one embodiment, the viral genome comprises two promoters. As a non-limiting example, the promoters are an EF1α promoter and a CMV promoter.

In one embodiment, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron: (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter and (9) GFAP promoter.

In one embodiment, the viral genome comprises an engineered promoter.

In another embodiment, the viral genome comprises a promoter from a naturally expressed protein.

In one embodiment, a region located approximately ~5 kb upstream of the first exon of the payload in order to allow for expression of the payload with the promoter. (See e.g., Puspasari et al. *Long Range Regulation of Human FXN Gene Expression*, PLOS ONE, 2011; the contents of which is herein incorporated by reference in its entirety; a 17 bp region located approximately 4.9 kb upstream of the first exon of the frataxin gene in order to allow for expression with the FRDA promoter).

In one embodiment, the vector genome may comprise a promoter such as, but not limited to, CMV or U6. As a non-limiting example, the promoter for the AAV particles comprising the payload of the present disclosure is a CMV promoter. As another non-limiting example, the promoter for the AAV particles comprising the payload of the present disclosure is a U6 promoter.

In one embodiment, the vector genome may comprise a CMV and a U6 promoter.

In one embodiment, the vector genome may comprise a CBA promoter.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VII) may be used in the viral genomes of the AAV particles of the disclosure to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A) (U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message n vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

In one embodiment, the viral genome may include at least one miRNA seed, binding site or full sequence. microRNAs (or miRNA or miR) are 19-25 nucleotide noncoding RNAs that bind to the sites of nucleic acid targets and downregulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In one embodiment, the viral genome may be engineered to include, alter or remove at least one miRNA binding site, sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTRs which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

In one embodiment, the viral genome of the AAV particles of the present disclosure comprise at least one polyadenylation sequence. The viral genome of the AAV particle may comprise a polyadenylation sequence between the 3' end of the payload coding sequence and the 5' end of the 3' ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

Viral Genome Component: Introns

In one embodiment, the payload region comprises at least one element to enhance the expression such as one or more introns or portions thereof. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80400, 80450, 80-500, 200-300, 200400, 200-500, 300400, 300-500, or 400-500.

In one embodiment, the vector genome comprises at least one element to enhance the transgene target specificity and expression (See e.g., Powell et al. *Viral Expression Cassette Elements to Enhance Transgene Target Specificity and Expression in Gene Therapy*, 2015: the contents of which are herein incorporated by reference in its entirety) such as an intron. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300400, 300-500, or 400-500.

Viral Genome Component: Filler Sequence

In one embodiment, the viral genome comprises one or more filler sequences.

In one embodiment, the viral genome comprises one or more filler sequences in order to have the length of the viral genome be the optimal size for packaging. As a non-limiting example, the viral genome comprises at least one filler sequence in order to have the length of the viral genome be about 2.3 kb. As a non-limiting example, the viral genome comprises at least one filler sequence in order to have the length of the viral genome be about 4.6 kb.

In one embodiment, the viral genome is a single stranded (ss) viral genome and comprises one or more filler sequences which have a length about between 0.1 kb-3.8 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, or 3.8 kb. As a non-limiting example, the total length filler sequence in the vector genome is 3.1 kb. As a non-limiting example, the total length filler sequence in the vector genome is 2.7 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb.

In one embodiment, the viral genome is a self-complementary (sc) viral genome and comprises one or more filler sequences which have a length about between 0.1 kb-1.5 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, or 1.5 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb In one embodiment, the viral genome comprises any portion of a filler sequence. The viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of a filler sequence.

In one embodiment, the viral genome is a single stranded (ss) viral genome and comprises one or more filler sequences in order to have the length of the viral genome be about 4.6 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3 to the polyadenylation signal sequence. As a non-limiting example, the viral genome comprises at least one filler sequence and the filler sequence is located 5' to the 3' ITR sequence. As a non-limiting example, the viral genome comprises at least one filler sequence, and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome is a self-complementary (sc) viral genome and comprises one or more filler sequences in order to have the length of the viral genome be about 2.3 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3' to the polyadenylation signal sequence. As a non-limiting example, the viral genome comprises at least one filler sequence and the filler sequence is located 5' to the 3' ITR sequence. As a non-limiting example, the viral genome comprises at least one filler sequence and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome may comprise one or more filler sequences between one of more regions of the viral genome. In one embodiment, the filler region may be located before a region such as, but not limited to, a payload region, an inverted terminal repeat (ITR), a promoter region, an intron region, an enhancer region, a polyadenylation signal sequence region, a multiple cloning site (MCS) region, and/or an exon region. In one embodiment, the filler region may be located after a region such as, but not limited to, a payload region, an inverted terminal repeat (ITR), a promoter region, an intron region, an enhancer region, a polyadenylation signal sequence region, a multiple cloning site (MCS) region, and/or an exon region. In one embodiment, the filler region may be located before and after a region such as, but not limited to, a payload region, an inverted terminal repeat (ITR), a promoter region, an intron region, an enhancer region, a polyadenylation signal sequence region, a multiple cloning site (MCS) region, and/or an exon region.

In one embodiment, the viral genome may comprise one or more filler sequences which bifurcates at least one region of the viral genome. The bifurcated region of the viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of the of the region to the 5' of the filler sequence region. As a non-limiting example, the filler sequence may bifurcate at least one region so that 10% of the region is located 5' to the filler sequence and 90% of the region is located 3' to the filler sequence. As a non-limiting example, the filler sequence may bifurcate at least one region so that 20% of the region is located 5' to the filler sequence and 80% of the region is located 3' to the filler sequence. As a non-limiting example, the filler sequence may bifurcate at least one region so that 30% of the region is located 5' to the filler sequence and 70% of the region is located 3' to the filler sequence. As a non-limiting example, the filler sequence may bifurcate at least one region so that 40% of the region is located 5' to the filler sequence and 60% of the region is located 3' to the filler sequence. As a non-limiting example, the filler sequence may bifurcate at least one region so that 50% of the region is located 5' to the filler sequence and 50% of the region is located 3' to the filler sequence. As a non-limiting example, the filler sequence may bifurcate at least one region so that 60% of the region is located 5' to the filler sequence and 40% of the region is located 3' to the filler sequence. As a non-limiting example, the filler sequence may bifurcate at least one region so that 70% of the region is located 5' to the filler sequence and 30% of the region is located 3' to the filler sequence. As a non-limiting example, the filler sequence may bifurcate at least one region so that 80% of the region is located 5' to the filler sequence and 20% of the region is located 3' to the filler sequence. As a non-limiting example, the filler sequence may bifurcate at least one region so that 90% of the region is located 5' to the filler sequence and 10% of the region is located 3' to the filler sequence.

In one embodiment, the viral genome comprises a filler sequence after the 5' ITR.

In one embodiment, the viral genome comprises a filler sequence after the promoter region. In one embodiment, the viral genome comprises a filler sequence after the payload region. In one embodiment, the viral genome comprises a filler sequence after the intron region. In one embodiment, the viral genome comprises a filler sequence after the enhancer region. In one embodiment, the viral genome comprises a filler sequence after the polyadenylation signal sequence region. In one embodiment, the viral genome comprises a filler sequence after the MCS region. In one embodiment, the viral genome comprises a filler sequence after the exon region.

In one embodiment, the viral genome comprises a filler sequence before the promoter region. In one embodiment, the viral genome comprises a filler sequence before the payload region. In one embodiment, the viral genome comprises a filler sequence before the intron region. In one embodiment, the viral genome comprises a filler sequence before the enhancer region. In one embodiment, the viral genome comprises a filler sequence before the polyadenylation signal sequence region. In one embodiment, the viral genome comprises a filler sequence before the MCS region. In one embodiment, the viral genome comprises a filler sequence before the exon region.

In one embodiment, the viral genome comprises a filler sequence before the 3' ITR.

In one embodiment, a filler sequence may be located between two regions, such as, but not limited to, the 5' ITR and the promoter region. In one embodiment, a filler sequence may be located between two regions, such as, but not limited to, the 5' ITR and the payload region. In one embodiment, a filler sequence may be located between two regions, such as, but not limited to, the 5' ITR and the intron region. In one embodiment, a filler sequence may be located between two regions, such as, but not limited to, the 5' ITR and the enhancer region. In one embodiment, a filler sequence may be located between two regions, such as, but not limited to, the 5' ITR and the polyadenylation signal sequence region. In one embodiment, a filler sequence may be located between two regions, such as, but not limited to, the 5' ITR and the MCS region.

In one embodiment, a filler sequence may be located between two regions, such as, but not limited to, the 5' ITR and the exon region.

In one embodiment, a filler sequence may be located between two regions, such as, but not limited to, the promoter region and the payload region. In one embodiment, a filler sequence may be located between two regions, such as, but not limited to, the promoter region and the intron region. In one embodiment, a filler sequence may be located between two regions, such as, but not limited to, the promoter region and the enhancer region. In one embodiment, a filler sequence may be located between two regions, such as, but not limited to, the promoter region and the polyadenylation signal sequence region. In one embodiment, a filler sequence may be located between two regions, such as, but not limited to, the promoter region and the MCS region. In one embodiment, a filler sequence may be located between two regions, such as, but not limited to, the promoter region and the exon region. In one embodiment, a filler sequence may be located between two regions, such as, but not limited to, the promoter region and the 3' ITR.

In one embodiment, a filler sequence may be located between two regions, such as, but not limited to, the payload region and the intron region. In one embodiment, a filler sequence may be located between two regions, such as, but not limited to, the payload region and the enhancer region. In one embodiment, a filler sequence may be located between two regions, such as, but not limited to, the payload region and the polyadenylation signal sequence region. In one embodiment, a filler sequence may be located between two regions, such as, but not limited to, the payload region and the MCS region. In one embodiment, a filler sequence may be located between two regions, such as, but not limited to, the payload region and the exon region.

In one embodiment, a filler sequence may be located between two regions, such as, but not limited to, the payload region and the 3' ITR.

In one embodiment, a filler sequence may be located between two regions, such as, but not limited to, the intron region and the enhancer region. In one embodiment, a filler sequence may be located between two regions, such as, but not limited to, the intron region and the polyadenylation signal sequence region. In one embodiment, a filler sequence may be located between two regions, such as, but not limited to, the intron region and the MCS region. In one embodiment, a filler sequence may be located between two regions, such as, but not limited to, the intron region and the exon region. In one embodiment, a filler sequence may be located between two regions, such as, but not limited to, the intron region and the 3' ITR. In one embodiment, a filler sequence may be located between two regions, such as, but not limited to, the enhancer region and the polyadenylation signal sequence region. In one embodiment, a filler sequence may be located between two regions, such as, but not limited to, the enhancer region and the MCS region. In one embodiment, a filler sequence may be located between two regions, such as, but not limited to, the enhancer region and the exon region. In one embodiment, a filler sequence may be located between two regions, such as, but not limited to, the enhancer region and the 3' ITR.

In one embodiment, a filler sequence may be located between two regions, such as, but not limited to, the polyadenylation signal sequence region and the MCS region. In one embodiment, a filler sequence may be located between two regions, such as, but not limited to, the polyadenylation signal sequence region and the exon region. In one embodiment, a filler sequence may be located between two regions, such as, but not limited to, the polyadenylation signal sequence region and the 3' ITR.

In one embodiment, a filler sequence may be located between two regions, such as, but not limited to, the MCS region and the exon region. In one embodiment, a filler sequence may be located between two regions, such as, but not limited to, the MCS region and the 3' ITR.

In one embodiment, a filler sequence may be located between two regions, such as, but not limited to, the exon region and the 3' ITR.

In one embodiment, a viral genome may comprise two filler sequences, the first filler sequence may be located between the 5' ITR and promoter region, and the second filler sequence may be located between the promoter region and payload region. In one embodiment, a viral genome may comprise two filler sequences, the first filler sequence may be located between the 5' ITR and promoter region, and the second filler sequence may be located between the promoter region and intron region. In one embodiment, a viral genome may comprise two filler sequences, the first filler sequence may be located between the 5' ITR and promoter region, and the second filler sequence may be located between the promoter region and enhancer region. In one embodiment, a viral genome may comprise two filler sequences, the first filler sequence may be located between the 5' ITR and promoter region, and the second filler sequence may be located between the promoter region and polyadenylation signal sequence region. In one embodiment, a viral genome may comprise two filler sequences, the first filler sequence may be located between the 5' ITR and promoter region, and the second filler sequence may be located between the promoter region and MCS region. In one embodiment, a viral genome may comprise two filler sequences, the first filler sequence may be located between the 5' ITR and promoter region, and the second filler sequence may be located between the promoter region and exon region. In one embodiment, a viral genome may comprise two filler sequences, the first filler sequence may be located between the 5' ITR and promoter region, and the second filler sequence may be located between the promoter region and 3' ITR In one embodiment, a viral genome may comprise two filler sequences, the first filler sequence may be located between the 5" ITR and promoter region, and the second filler sequence may be located between the payload region and intron region. In one embodiment, a viral genome may comprise two filler sequences, the first filler sequence may be located between the 5' ITR and promoter region, and the second filler sequence may be located between the payload region and enhancer region. In one embodiment, a viral genome may comprise two filler sequences, the first filler sequence may be located between the 5' ITR and promoter region, and the second filler sequence may be located between the payload region and polyadenylation signal sequence region. In one embodiment, a viral genome may comprise two filler sequences, the first filler sequence may be located between the 5' ITR and promoter region, and the second filler sequence may be located between the payload region and MCS region. In one embodiment, a viral genome may comprise two filler sequences, the first filler sequence may be located between the 5' ITR and promoter region, and the second filler sequence may be located between the payload region and exon region. In one embodiment, a viral genome may comprise two filler sequences, the first filler sequence may be located between the 5' ITR and promoter region, and the second filler sequence may be located between the payload region and 3' ITR. In one embodiment, a viral genome may comprise two filler sequences, the first filler sequence may be located between the 5' ITR and promoter region, and the second filler sequence may be located between the intron region and enhancer region. In one embodiment, a viral genome may comprise two filler sequences, the first filler sequence may be located between the 5' ITR and promoter region, and the second filler sequence may be located between the intron region and polyadenylation signal sequence region. In one embodiment, a viral genome may comprise two filler sequences, the first filler sequence may be located between the 5' ITR and promoter region, and the second filler sequence may be located between the intron region and MCS region. In one embodiment, a viral genome may comprise two filler sequences, the first filler sequence may be located between the 5' ITR and promoter region, and the second filler sequence may be located between the intron region and exon region. In one embodiment, a viral genome may comprise two filler sequences, the first filler sequence may be located between the 5' ITR and promoter region, and the second filler sequence may be located between the intron region and 3' ITR. In one embodiment, a viral genome may comprise two filler sequences, the first filler sequence may be located between the 5' ITR and promoter region, and the second filler sequence may be located between the enhancer region and polyadenylation signal sequence region. In one embodiment, a viral genome may comprise two filler sequences, the first filler sequence may be located between the 5' ITR and promoter region, and the second filler sequence may be located between the enhancer region and MCS region. In one embodiment, a viral genome may comprise two filler sequences, the first filler sequence may be located between the 5' ITR and promoter region, and the second filler sequence may be located between the enhancer region and exon region. In one embodiment, a viral genome may comprise two filler sequences, the first filler sequence may be located between the 5' ITR and promoter region, and the second filler sequence may be located between the enhancer region and 3' ITR. In one embodiment, a viral genome may comprise two filler sequences, the first filler sequence may be located between the 5' ITR and promoter region, and the second filler sequence may be located between the polyadenylation signal sequence region and MCS region. In one embodiment, a viral genome may comprise two filler sequences, the first filler sequence may be located between the 5' ITR and promoter region, and the second filler sequence may be located between the polyadenylation signal sequence region and exon region. In one embodiment, a viral genome may comprise two filler sequences, the first filler sequence may be located between the 5' ITR and promoter region, and the second filler sequence may be located between the polyadenylation signal sequence region and 3' ITR. In one embodiment, a viral genome may comprise two filler sequences, the first filler sequence may be located between the 5' ITR and promoter region, and the second filler sequence may be located between the MCS region and exon region. In one embodiment, a viral genome may comprise two filler sequences, the first filler sequence may be located between the 5' ITR and promoter region, and the second filler sequence may be located between the MCS region and 3' ITR. In one embodiment, a viral genome may comprise two filler sequences, the first filler sequence may be located between the 5' ITR and promoter region, and the second filler sequence may be located between the exon region and 3' ITR.

In one embodiment, a viral genome may comprise two filler sequences, the first filler sequence may be located between the 5' ITR and payload region, and the second filler sequence may be located between the promoter region and payload region. In one embodiment, a viral genome may comprise two filler sequences, the first filler sequence may be located between the 5' ITR and payload region, and the second filler sequence may be located between the promoter region and intron region. In one embodiment, a viral genome may comprise two filler sequences, the first filler sequence may be located between the 5' ITR and payload region, and the second filler sequence may be located between the promoter region and enhancer region. In one embodiment, a viral genome may comprise two filler sequences, the first filler sequence may be located between the 5' ITR and payload region, and the second filler sequence may be located between the promoter region and polyadenylation signal sequence region. In one embodiment, a viral genome may comprise two filler sequences, the first filler sequence may be located between the 5' ITR and payload region, and the second filler sequence may be located between the promoter region and MCS region. In one embodiment, a viral genome may comprise two filler sequences, the first filler sequence may be located between the 5' ITR and payload region, and the second filler sequence may be located between the promoter region and exon region. In one embodiment, a viral genome may comprise two filler sequences, the first filler sequence may be located between the 5' ITR and payload region, and the second filler sequence may be located between the promoter region and 3' ITR. In one embodiment, a viral genome may comprise two filler sequences, the first filler sequence may be located between the 5' ITR and payload region, and the second filler sequence may be located between the payload region and intron region. In one embodiment, a viral genome may comprise two filler sequences, the first filler sequence may be located between the 5' ITR and payload region, and the second filler sequence may be located between the payload region and enhancer region. In one embodiment, a viral genome may comprise two filler sequences, the first filler sequence may be located between the 5' ITR and payload region, and the second filler sequence may be located between the payload region and polyadenylation signal sequence region. In one embodiment, a viral genome may comprise two filler sequences, the first filler sequence may be located between the 5' ITR and payload region, and the second filler sequence may be located between the payload region and MCS region. In one embodiment, a viral genome may comprise two filler sequences, the first filler sequence may be located between the 5' ITR and payload region, and the second filler sequence may be located between the payload region and exon region. In one embodiment, a viral genome may comprise two filler sequences, the first filler sequence may be located between the 5' ITR and payload region, and the second filler sequence may be located between the payload region and 3' ITR. In one embodiment, a viral genome may comprise two filler sequences, the first filler sequence may be located between the 5' ITR and payload region, and the second filler sequence may be located between the intron region and enhancer region. In one embodiment, a viral genome may comprise two filler sequences, the first filler sequence may be located between the 5' ITR and payload region, and the second filler sequence may be located between the intron region and polyadenylation signal sequence region. In one embodiment, a viral genome may comprise two filler sequences, the first filler sequence may be located between the 5' ITR and payload region, and the second filler sequence may be located between the intron region and MCS region. In one embodiment, a viral genome may comprise two filler sequences, the first filler sequence may be located between the 5' ITR and payload region, and the second filler sequence may be located between the intron region and exon region. In one embodiment, a viral genome may comprise two filler sequences, the first filler sequence may be located between the 5' ITR and payload region, and the second filler sequence may be located between the intron region and 3' ITR. In one embodiment, a viral genome may comprise two filler sequences, the first filler sequence may be located between the 5' ITR and payload region, and the second filler sequence may be located between the enhancer region and polyadenylation signal sequence region. In one embodiment, a viral genome may comprise two filler sequences, the first filler sequence may be located between the 5' ITR and payload region, and the second filler sequence may be located between the enhancer region and MCS region. In one embodiment, a viral genome may comprise two filler sequences, the first filler sequence may be located between the 5' ITR and payload region, and the second filler sequence may be located between the enhancer region and exon region. In one embodiment, a viral genome may comprise two filler sequences, the first filler sequence may be located between the 5' ITR and payload region, and the second filler sequence may be located between the enhancer region and 3' ITR. In one embodiment, a viral genome may comprise two filler sequences, the first filler sequence may be located between the 5' ITR and payload region, and the second filler sequence may be located between the polyadenylation signal sequence region and MCS region. In one embodiment, a viral genome may comprise two filler sequences, the first filler sequence may be located between the 5' ITR and payload region, and the second filler sequence may be located between the polyadenylation signal sequence region and exon region. In one embodiment, a viral genome may comprise two filler sequences, the first filler sequence may be located between the 5' ITR and payload region, and the second filler sequence may be located between the polyadenylation signal sequence region and 3' ITR. In one embodiment, a viral genome may comprise two filler sequences, the first filler sequence may be located between the 5' ITR and payload region, and the second filler sequence may be located between the MCS region and exon region. In one embodiment, a viral genome may comprise two filler sequences, the first filler sequence may be located between the 5' ITR and payload region, and the second filler sequence may be located between the MCS region and 3' ITR. In one embodiment, a viral genome may comprise two filler sequences, the first filler sequence may be located between the 5' ITR and payload region, and the second filler sequence may be located between the exon region and 3' ITR.

In one embodiment, a viral genome may comprise two filler sequences, the first filler sequence may be located between the 5' ITR and intron region, and the second filler sequence may be located between the promoter region and payload region. In one embodiment, a viral genome may comprise two filler sequences, the first filler sequence may be located between the 5' ITR and intron region, and the second filler sequence may be located between the promoter region and intron region. In one embodiment, a viral genome may comprise two filler sequences, the first filler sequence may be located between the 5' ITR and intron region, and the second filler sequence may be located between the promoter region and enhancer region. In one embodiment, a viral genome may comprise two filler sequences, the first filler sequence may be located between the 5' ITR and intron region, and the second filler sequence may be located between the promoter region and polyadenylation signal sequence region. In one embodiment, a viral genome may comprise two filler sequences, the first filler sequence may be located between the 5' ITR and intron region, and the second filler sequence may be located between the promoter region and MCS region. In one embodiment, a viral genome may comprise two filler sequences, the first filler sequence may be located between the 5' ITR and intron region, and the second filler sequence may be located between the promoter region and exon region. In one embodiment, a viral genome may comprise two filler sequences, the first filler sequence may be located between the 5' ITR and intron region, and the second filler sequence may be located between the promoter region and 3' ITR. In one embodiment, a viral genome may comprise two filler sequences, the first filler sequence may be located between the 5' ITR and intron region, and the second filler sequence may be located between the payload region and intron region. In one embodiment, a viral genome may comprise two filler sequences, the first filler sequence may be located between the 5' ITR and intron region, and the second filler sequence may be located between the payload region and enhancer region. In one embodiment, a viral genome may comprise two filler sequences, the first filler sequence may be located between the 5' ITR and intron region, and the second filler sequence may be located between the payload region and polyadenylation signal sequence region. In one embodiment, a viral genome may comprise two filler sequences, the first filler sequence may be located between the 5' ITR and intron region, and the second filler sequence may be located between the payload region and MCS region. In one embodiment, a viral genome may comprise two filler sequences, the first filler sequence may be located between the 5' ITR and intron region, and the second filler sequence may be located between the payload region and exon region. In one embodiment, a viral genome may comprise two filler sequences, the first filler sequence may be located between the 5' ITR and intron region, and the second filler sequence may be located between the payload region and 3' ITR. In one embodiment, a viral genome may comprise two filler sequences, the first filler sequence may be located between the 5' ITR and intron region, and the second filler sequence may be located between the intron region and enhancer region. In one embodiment, a viral genome may comprise two filler sequences, the first filler sequence may be located between the 5' ITR and intron region, and the second filler sequence may be located between the intron region and polyadenylation signal sequence region. In one embodiment, a viral genome may comprise two filler sequences, the first filler sequence may be located between the 5' ITR and intron region, and the second filler sequence may be located between the intron region and MCS region. In one embodiment, a viral genome may comprise two filler sequences, the first filler sequence may be located between the 5' ITR and intron region, and the second filler sequence may be located between the intron region and exon region. In one embodiment, a viral genome may comprise two filler sequences, the first filler sequence may be located between the 5' ITR and intron region, and the second filler sequence may be located between the intron region and 3' ITR. In one embodiment, a viral genome may comprise two filler sequences, the first filler sequence may be located between the 5' ITR and intron region, and the second filler sequence may be located between the enhancer region and polyadenylation signal sequence region. In one embodiment, a viral genome may comprise two filler sequences, the first filler sequence may be located between the 5' ITR and intron region, and the second filler sequence may be located between the enhancer region and MCS region. In one embodiment, a viral genome may comprise two filler sequences, the first filler sequence may be located between the 5' ITR and intron region, and the second filler sequence may be located between the enhancer region and exon region. In one embodiment, a viral genome may comprise two filler sequences, the first filler sequence may be located between the 5' ITR and intron region, and the second filler sequence may be located between the enhancer region and 3' ITR. In one embodiment, a viral genome may comprise two filler sequences, the first filler sequence may be located between the 5' ITR and intron region, and the second filler sequence may be located between the polyadenylation signal sequence region and MCS region. In one embodiment, a viral genome may comprise two filler sequences, the first filler sequence may be located between the 5' ITR and intron region, and the second filler sequence may be located between the polyadenylation signal sequence region and exon region. In one embodiment, a viral genome may comprise two filler sequences, the first filler sequence may be located between the 5' ITR and intron region, and the second filler sequence may be located between the polyadenylation signal sequence region and 3' ITR. In one embodiment, a viral genome may comprise two filler sequences, the first filler sequence may be located between the 5' ITR and intron region, and the second filler sequence may be located between the MCS region and exon region. In one embodiment, a viral genome may comprise two filler sequences, the first filler sequence may be located between the 5' ITR and intron region, and the second filler sequence may be located between the MCS region and 3' ITR. In one embodiment, a viral genome may comprise two filler sequences, the first filler sequence may be located between the 5' ITR and intron region, and the second filler sequence may be located between the exon region and 3' ITR.

In one embodiment, a viral genome may comprise two filler sequences, the first filler sequence may be located between the 5' ITR and enhancer region, and the second filler sequence may be located between the promoter region and payload region. In one embodiment, a viral genome may comprise two filler sequences, the first filler sequence may be located between the 5' ITR and enhancer region, and the second filler sequence may be located between the promoter region and intron region. In one embodiment, a viral genome may comprise two filler sequences, the first filler sequence may be located between the 5' ITR and enhancer region, and the second filler sequence may be located between the promoter region and enhancer region. In one embodiment, a viral genome may comprise two filler sequences, the first filler sequence may be located between the 5' ITR and enhancer region, and the second filler sequence may be located between the promoter region and polyadenylation signal sequence region. In one embodiment, a viral genome may comprise two filler sequences, the first filler sequence may be located between the 5' ITR and enhancer region, and the second filler sequence may be located between the promoter region and MCS region. In one embodiment, a viral genome may comprise two filler sequences, the first filler sequence may be located between the 5' ITR and enhancer region, and the second filler sequence may be located between the promoter region and exon region. In one embodiment, a viral genome may comprise two filler sequences, the first filler sequence may be located between the 5' ITR and enhancer region, and the second filler sequence may be located between the promoter region and 3' ITR. In one embodiment, a viral genome may comprise two filler sequences, the first filler sequence may be located between the 5' ITR and enhancer region, and the second filler sequence may be located between the payload region and intron region. In one embodiment, a viral genome may comprise two filler sequences, the first filler sequence may be located between the 5' ITR and enhancer region, and the second filler sequence may be located between the payload region and enhancer region. In one embodiment, a viral genome may comprise two filler sequences, the first filler sequence may be located between the 5' ITR and enhancer region, and the second filler sequence may be located between the payload region and polyadenylation signal sequence region. In one embodiment, a viral genome may comprise two filler sequences, the first filler sequence may be located between the 5' ITR and enhancer region, and the second filler sequence may be located between the payload region and MCS region. In one embodiment, a viral genome may comprise two filler sequences, the first filler sequence may be located between the 5' ITR and enhancer region, and the second filler sequence may be located between the payload region and exon region. In one embodiment, a viral genome may comprise two filler sequences, the first filler sequence may be located between the 5' ITR and enhancer region, and the second filler sequence may be located between the payload region and 3' ITR. In one embodiment, a viral genome may comprise two filler sequences, the first filler sequence may be located between the 5' ITR and enhancer region, and the second filler sequence may be located between the intron region and enhancer region. In one embodiment, a viral genome may comprise two filler sequences, the first filler sequence may be located between the 5' ITR and enhancer region, and the second filler sequence may be located between the intron region and polyadenylation signal sequence region. In one embodiment, a viral genome may comprise two filler sequences, the first filler sequence may be located between the 5' ITR and enhancer region, and the second filler sequence may be located between the intron region and MCS region. In one embodiment, a viral genome may comprise two filler sequences, the first filler sequence may be located between the 5' ITR and enhancer region, and the second filler sequence may be located between the intron region and exon region. In one embodiment, a viral genome may comprise two filler sequences, the first filler sequence may be located between the 5' ITR and enhancer region, and the second filler sequence may be located between the intron region and 3' ITR. In one embodiment, a viral genome may comprise two filler sequences, the first filler sequence may be located between the 5' ITR and enhancer region, and the second filler sequence may be located between the enhancer region and polyadenylation signal sequence region. In one embodiment, a viral genome may comprise two filler sequences, the first filler sequence may be located between the 5' ITR and enhancer region, and the second filler sequence may be located between the enhancer region and MCS region. In one embodiment, a viral genome may comprise two filler sequences, the first filler sequence may be located between the 5' ITR and enhancer region, and the second filler sequence may be located between the enhancer region and exon region. In one embodiment, a viral genome may comprise two filler sequences, the first filler sequence may be located between the 5' ITR and enhancer region, and the second filler sequence may be located between the enhancer region and 3' ITR. In one embodiment, a viral genome may comprise two filler sequences, the first filler sequence may be located between the 5' ITR and enhancer region, and the second filler sequence may be located between the polyadenylation signal sequence region and MCS region. In one embodiment, a viral genome may comprise two filler sequences, the first filler sequence may be located between the 5' ITR and enhancer region, and the second filler sequence may be located between the polyadenylation signal sequence region and exon region. In one embodiment, a viral genome may comprise two filler sequences, the first filler sequence may be located between the 5' ITR and enhancer region, and the second filler sequence may be located between the polyadenylation signal sequence region and 3' ITR. In one embodiment, a viral genome may comprise two filler sequences, the first filler sequence may be located between the 5' ITR and enhancer region, and the second filler sequence may be located between the MCS region and exon region. In one embodiment, a viral genome may comprise two filler sequences, the first filler sequence may be located between the 5' ITR and enhancer region, and the second filler sequence may be located between the MCS region and 3' ITR. In one embodiment, a viral genome may comprise two filler sequences, the first filler sequence may be located between the 5' ITR and enhancer region, and the second filler sequence may be located between the exon region and 3' ITR In one embodiment, a viral genome may comprise two filler sequences, the first filler sequence may be located between the 5' ITR and polyadenylation signal sequence region, and the second filler sequence may be located between the promoter region and payload region. In one embodiment, a viral genome may comprise two filler sequences, the first filler sequence may be located between the 5' ITR and polyadenylation signal sequence region, and the second filler sequence may be located between the promoter region and intron region. In one embodiment, a viral genome may comprise two filler sequences, the first filler sequence may be located between the 5' ITR and polyadenylation signal sequence region, and the second filler sequence may be located between the promoter region and enhancer region. In one embodiment, a viral genome may comprise two filler sequences, the first filler sequence may be located between the 5' ITR and polyadenylation signal sequence region, and the second filler sequence may be located between the promoter region and polyadenylation signal sequence region. In one embodiment, a viral genome may comprise two filler sequences, the first filler sequence may be located between the 5' ITR and promoter region and MCS region. In one embodiment, a viral genome may comprise two filler sequences, the first filler sequence may be located between the 5' ITR and polyadenylation signal sequence region, and the second filler sequence may be located between the promoter region and exon region. In one embodiment, a viral genome may comprise two filler sequences, the first filler sequence may be located between the 5' ITR and polyadenylation signal sequence region, and the second filler sequence may be located between the promoter region and 3' ITR. In one embodiment, a viral genome may comprise two filler sequences, the first filler sequence may be located between the 5' ITR and polyadenylation signal sequence region, and the second filler sequence may be located between the payload region and intron region. In one embodiment, a viral genome may comprise two filler sequences, the first filler sequence may be located between the 5' ITR and polyadenylation signal sequence region, and the second filler sequence may be located between the payload region and enhancer region. In one embodiment, a viral genome may comprise two filler sequences, the first filler sequence may be located between the 5' ITR and polyadenylation signal sequence region, and the second filler sequence may be located between the payload region and polyadenylation signal sequence region. In one embodiment, a viral genome may comprise two filler sequences, the first filler sequence may be located between the 5' ITR and polyadenylation signal sequence region, and the second filler sequence may be located between the payload region and MCS region. In one embodiment, a viral genome may comprise two filler sequences, the first filler sequence may be located between the 5' ITR and polyadenylation signal sequence region, and the second filler sequence may be located between the payload region and exon region. In one embodiment, a viral genome may comprise two filler sequences, the first filler sequence may be located between the 5' ITR and polyadenylation signal sequence region, and the second filler sequence may be located between the payload region and 3' ITR. In one embodiment, a viral genome may comprise two filler sequences, the first filler sequence may be located between the 5' ITR and polyadenylation signal sequence region, and the second filler sequence may be located between the intron region and enhancer region. In one embodiment, a viral genome may comprise two filler sequences, the first filler sequence may be located between the 5' ITR and polyadenylation signal sequence region, and the second filler sequence may be located between the intron region and polyadenylation signal sequence region. In one embodiment, a viral genome may comprise two filler sequences, the first filler sequence may be located between the 5' ITR and intron region and MCS region. In one embodiment, a viral genome may comprise two filler sequences, the first filler sequence may be located between the 5' ITR and polyadenylation signal sequence region, and the second filler sequence may be located between the intron region and exon region. In one embodiment, a viral genome may comprise two filler sequences, the first filler sequence may be located between the 5' ITR and polyadenylation signal sequence region, and the second filler sequence may be located between the intron region and 3' ITR. In one embodiment, a viral genome may comprise two filler sequences, the first filler sequence may be located between the 5' ITR and polyadenylation signal sequence region, and the second filler sequence may be located between the enhancer region and polyadenylation signal sequence region. In one embodiment, a viral genome may comprise two filler sequences, the first filler sequence may be located between the 5' ITR and polyadenylation signal sequence region, and the second filler sequence may be located between the enhancer region and MCS region. In one embodiment, a viral genome may comprise two filler sequences, the first filler sequence may be located between the 5' ITR and polyadenylation signal sequence region, and the second filler sequence may be located between the enhancer region and exon region. In one embodiment, a viral genome may comprise two filler sequences, the first filler sequence may be located between the 5' ITR and polyadenylation signal sequence region, and the second filler sequence may be located between the enhancer region and 3' ITR. In one embodiment, a viral genome may comprise two filler sequences, the first filler sequence may be located between the 5' ITR and polyadenylation signal sequence region, and the second filler sequence may be located between the polyadenylation signal sequence region and MCS region. In one embodiment, a viral genome may comprise two filler sequences, the first filler sequence may be located between the 5' ITR and polyadenylation signal sequence region, and the second filler sequence may be located between the polyadenylation signal sequence region and exon region. In one embodiment, a viral genome may comprise two filler sequences, the first filler sequence may be located between the 5' ITR and polyadenylation signal sequence region, and the second filler sequence may be located between the polyadenylation signal sequence region and 3' ITR In one embodiment, a viral genome may comprise two filler sequences, the first filler sequence may be located between the 5' ITR and polyadenylation signal sequence region, and the second filler sequence may be located between the MCS region and exon region. In one embodiment, a viral genome may comprise two filler sequences, the first filler sequence may be located between the 5' ITR and polyadenylation signal sequence region, and the second filler sequence may be located between the MCS region and 3' ITR. In one embodiment, a viral genome may comprise two filler sequences, the first filler sequence may be located between the 5' ITR and polyadenylation signal sequence region, and the second filler sequence may be located between the exon region and 3' ITR.

In one embodiment, a viral genome may comprise two filler sequences, the first filler sequence may be located between the 5' ITR and MCS region, and the second filler sequence may be located between the promoter region and payload region. In one embodiment, a viral genome may comprise two filler sequences, the first filler sequence may be located between the 5' ITR and MCS region, and the second filler sequence may be located between the promoter region and intron region. In one embodiment, a viral genome may comprise two filler sequences, the first filler sequence may be located between the 5' ITR and MCS region, and the second filler sequence may be located between the promoter region and enhancer region. In one embodiment, a viral genome may comprise two filler sequences, the first filler sequence may be located between the 5' ITR and MCS region, and the second filler sequence may be located between the promoter region and polyadenylation signal sequence region. In one embodiment, a viral genome may comprise two filler sequences, the first filler sequence may be located between the 5' ITR and MCS region, and the second filler sequence may be located between the promoter region and MCS region. In one embodiment, a viral genome may comprise two filler sequences, the first filler sequence may be located between the 5' ITR and MCS region, and the second filler sequence may be located between the promoter region and exon region. In one embodiment, a viral genome may comprise two filler sequences, the first filler sequence may be located between the 5' ITR and MCS region, and the second filler sequence may be located between the promoter region and 3' ITR. In one embodiment, a viral genome may comprise two filler sequences, the first filler sequence may be located between the 5' ITR and MCS region, and the second filler sequence may be located between the payload region and intron region. In one embodiment, a viral genome may comprise two filler sequences, the first filler sequence may be located between the 5' ITR and MCS region, and the second filler sequence may be located between the payload region and enhancer region. In one embodiment, a viral genome may comprise two filler sequences, the first filler sequence may be located between the 5' ITR and MCS region, and the second filler sequence may be located between the payload region and polyadenylation signal sequence region. In one embodiment, a viral genome may comprise two filler sequences, the first filler sequence may be located between the 5' ITR and MCS region, and the second filler sequence may be located between the payload region and MCS region. In one embodiment, a viral genome may comprise two filler sequences, the first filler sequence may be located between the 5' ITR and MCS region, and the second filler sequence may be located between the payload region and exon region. In one embodiment, a viral genome may comprise two filler sequences, the first filler sequence may be located between the 5' ITR and MCS region, and the second filler sequence may be located between the payload region and 3' ITR In one embodiment, a viral genome may comprise two filler sequences, the first filler sequence may be located between the 5' ITR and MCS region, and the second filler sequence may be located between the intron region and enhancer region. In one embodiment, a viral genome may comprise two filler sequences, the first filler sequence may be located between the 5' ITR and MCS region, and the second filler sequence may be located between the intron region and polyadenylation signal sequence region. In one embodiment, a viral genome may comprise two filler sequences, the first filler sequence may be located between the 5' ITR and MCS region, and the second filler sequence may be located between the intron region and MCS region. In one embodiment, a viral genome may comprise two filler sequences, the first filler sequence may be located between the 5' ITR and MCS region, and the second filler sequence may be located between the intron region and exon region. In one embodiment, a viral genome may comprise two filler sequences, the first filler sequence may be located between the 5' ITR and MCS region, and the second filler sequence may be located between the intron region and 3' ITR. In one embodiment, a viral genome may comprise two filler sequences, the first filler sequence may be located between the 5' ITR and MCS region, and the second filler sequence may be located between the enhancer region and polyadenylation signal sequence region. In one embodiment, a viral genome may comprise two filler sequences, the first filler sequence may be located between the 5' ITR and MCS region, and the second filler sequence may be located between the enhancer region and MCS region. In one embodiment, a viral genome may comprise two filler sequences, the first filler sequence may be located between the 5' ITR and MCS region, and the second filler sequence may be located between the enhancer region and exon region. In one embodiment, a viral genome may comprise two filler sequences, the first filler sequence may be located between the 5' ITR and MCS region, and the second filler sequence may be located between the enhancer region and 3' ITR. In one embodiment, a viral genome may comprise two filler sequences, the first filler sequence may be located between the 5' ITR and MCS region, and the second filler sequence may be located between the polyadenylation signal sequence region and MCS region. In one embodiment, a viral genome may comprise two filler sequences, the first filler sequence may be located between the 5' ITR and MCS region, and the second filler sequence may be located between the polyadenylation signal sequence region and exon region. In one embodiment, a viral genome may comprise two filler sequences, the first filler sequence may be located between the 5' ITR and MCS region, and the second filler sequence may be located between the polyadenylation signal sequence region and 3' ITR. In one embodiment, a viral genome may comprise two filler sequences, the first filler sequence may be located between the 5' ITR and MCS region, and the second filler sequence may be located between the MCS region and exon region. In one embodiment, a viral genome may comprise two filler sequences, the first filler sequence may be located between the 5' FR and MCS region, and the second filler sequence may be located between the MCS region and 3' ITR. In one embodiment, a viral genome may comprise two filler sequences, the first filler sequence may be located between the 5' ITR and MCS region, and the second filler sequence may be located between the exon region and 3' ITR.

In one embodiment, a viral genome may comprise two filler sequences, the first filler sequence may be located between the 5' ITR and exon region, and the second filler sequence may be located between the promoter region and payload region. In one embodiment, a viral genome may comprise two filler sequences, the first filler sequence may be located between the 5' ITR and exon region, and the second filler sequence may be located between the promoter region and intron region. In one embodiment, a viral genome may comprise two filler sequences, the first filler sequence may be located between the 5' ITR and exon region, and the second filler sequence may be located between the promoter region and enhancer region. In one embodiment, a viral genome may comprise two filler sequences, the first filler sequence may be located between the 5' ITR and exon region, and the second filler sequence may be located between the promoter region and polyadenylation signal sequence region. In one embodiment, a viral genome may comprise two filler sequences, the first filler sequence may be located between the 5' ITR and exon region, and the second filler sequence may be located between the promoter region and MCS region. In one embodiment, a viral genome may comprise two filler sequences, the first filler sequence may be located between the 5' ITR and exon region, and the second filler sequence may be located between the promoter region and exon region. In one embodiment, a viral genome may comprise two filler sequences, the first filler sequence may be located between the 5' ITR and exon region, and the second filler sequence may be located between the promoter region and 3' ITR. In one embodiment, a viral genome may comprise two filler sequences, the first filler sequence may be located between the 5' ITR and exon region, and the second filler sequence may be located between the payload region and intron region. In one embodiment, a viral genome may comprise two filler sequences, the first filler sequence may be located between the 5' ITR and exon region, and the second filler sequence may be located between the payload region and enhancer region. In one embodiment, a viral genome may comprise two filler sequences, the first filler sequence may be located between the 5' ITR and exon region, and the second filler sequence may be located between the payload region and polyadenylation signal sequence region. In one embodiment, a viral genome may comprise two filler sequences, the first filler sequence may be located between the 5' ITR and exon region, and the second filler sequence may be located between the payload region and MCS region. In one embodiment, a viral genome may comprise two filler sequences, the first filler sequence may be located between the 5' ITR and exon region, and the second filler sequence may be located between the payload region and exon region. In one embodiment, a viral genome may comprise two filler sequences, the first filler sequence may be located between the 5' ITR and exon region, and the second filler sequence may be located between the payload region and 3' ITR. In one embodiment, a viral genome may comprise two filler sequences, the first filler sequence may be located between the 5' ITR and exon region, and the second filler sequence may be located between the intron region and enhancer region. In one embodiment, a viral genome may comprise two filler sequences, the first filler sequence may be located between the 5' ITR and exon region, and the second filler sequence may be located between the intron region and polyadenylation signal sequence region. In one embodiment, a viral genome may comprise two filler sequences, the first filler sequence may be located between the 5' ITR and exon region, and the second filler sequence may be located between the intron region and MCS region. In one embodiment, a viral genome may comprise two filler sequences, the first filler sequence may be located between the 5' ITR and exon region, and the second filler sequence may be located between the intron region and exon region. In one embodiment, a viral genome may comprise two filler sequences, the first filler sequence may be located between the 5' ITR and exon region, and the second filler sequence may be located between the intron region and 3' ITR. In one embodiment, a viral genome may comprise two filler sequences, the first filler sequence may be located between the 5' ITR and exon region, and the second filler sequence may be located between the enhancer region and polyadenylation signal sequence region. In one embodiment, a viral genome may comprise two filler sequences, the first filler sequence may be located between the 5' ITR and exon region, and the second filler sequence may be located between the enhancer region and MCS region. In one embodiment, a viral genome may comprise two filler sequences, the first filler sequence may be located between the 5' ITR and exon region, and the second filler sequence may be located between the enhancer region and exon region. In one embodiment, a viral genome may comprise two filler sequences, the first filler sequence may be located between the 5' ITR and exon region, and the second filler sequence may be located between the enhancer region and 3' ITR. In one embodiment, a viral genome may comprise two filler sequences, the first filler sequence may be located between the 5' ITR and exon region, and the second filler sequence may be located between the polyadenylation signal sequence region and MCS region. In one embodiment, a viral genome may comprise two filler sequences, the first filler sequence may be located between the 5' ITR and exon region, and the second filler sequence may be located between the polyadenylation signal sequence region and exon region. In one embodiment, a viral genome may comprise two filler sequences, the first filler sequence may be located between the 5' ITR and exon region, and the second filler sequence may be located between the polyadenylation signal sequence region and 3' ITR. In one embodiment, a viral genome may comprise two filler sequences, the first filler sequence may be located between the 5' ITR and exon region, and the second filler sequence may be located between the MCS region and exon region. In one embodiment, a viral genome may comprise two filler sequences, the first filler sequence may be located between the 5' ITR and exon region, and the second filler sequence may be located between the MCS region and 3' ITR. In one embodiment, a viral genome may comprise two filler sequences, the first filler sequence may be located between the 5' ITR and exon region, and the second filler sequence may be located between the exon region and 3' ITR.

In one embodiment, a viral genome may comprise two filler sequences, the first filler sequence may be located between the promoter region and payload region, and the second filler sequence may be located between the payload region and intron region. In one embodiment, a viral genome may comprise two filler sequences, the first filler sequence may be located between the promoter region and payload region, and the second filler sequence may be located between the payload region and enhancer region. In one embodiment, a viral genome may comprise two filler sequences, the first filler sequence may be located between the promoter region and payload region, and the second filler sequence may be located between the payload region and polyadenylation signal sequence region. In one embodiment, a viral genome may comprise two filler sequences, the first filler sequence may be located between the promoter region and payload region, and the second filler sequence may be located between the payload region and MCS region. In one embodiment, a viral genome may comprise two filler sequences, the first filler sequence may be located between the promoter region and payload region, and the second filler sequence may be located between the payload region and exon region. In one embodiment, a viral genome may comprise two filler sequences, the first filler sequence may be located between the promoter region and payload region, and the second filler sequence may be located between the payload region and 3' ITR. In one embodiment, a viral genome may comprise two filler sequences, the first filler sequence may be located between the promoter region and payload region, and the second filler sequence may be located between the intron region and enhancer region. In one embodiment, a viral genome may comprise two filler sequences, the first filler sequence may be located between the promoter region and payload region, and the second filler sequence may be located between the intron region and polyadenylation signal sequence region. In one embodiment, a viral genome may comprise two filler sequences, the first filler sequence may be located between the promoter region and payload region, and the second filler sequence may be located between the intron region and MCS region. In one embodiment, a viral genome may comprise two filler sequences, the first filler sequence may be located between the promoter region and payload region, and the second filler sequence may be located between the intron region and exon region. In one embodiment, a viral genome may comprise two filler sequences, the first filler sequence may be located between the promoter region and payload region, and the second filler sequence may be located between the intron region and 3' ITR. In one embodiment, a viral genome may comprise two filler sequences, the first filler sequence may be located between the promoter region and payload region, and the second filler sequence may be located between the enhancer region and polyadenylation signal sequence region. In one embodiment, a viral genome may comprise two filler sequences, the first filler sequence may be located between the promoter region and payload region, and the second filler sequence may be located between the enhancer region and MCS region. In one embodiment, a viral genome may comprise two filler sequences, the first filler sequence may be located between the promoter region and payload region, and the second filler sequence may be located between the enhancer region and exon region. In one embodiment, a viral genome may comprise two filler sequences, the first filler sequence may be located between the promoter region and payload region, and the second filler sequence may be located between the enhancer region and 3' ITR. In one embodiment, a viral genome may comprise two filler sequences, the first filler sequence may be located between the promoter region and payload region, and the second filler sequence may be located between the polyadenylation signal sequence region and MCS region. In one embodiment, a viral genome may comprise two filler sequences, the first filler sequence may be located between the promoter region and payload region, and the second filler sequence may be located between the polyadenylation signal sequence region and exon region. In one embodiment, a viral genome may comprise two filler sequences, the first filler sequence may be located between the promoter region and payload region, and the second filler sequence may be located between the polyadenylation signal sequence region and 3' ITR. In one embodiment, a viral genome may comprise two filler sequences, the first filler sequence may be located between the promoter region and payload region, and the second filler sequence may be located between the MCS region and exon region. In one embodiment, a viral genome may comprise two filler sequences, the first filler sequence may be located between the promoter region and payload region, and the second filler sequence may be located between the MCS region and 3' ITR. In one embodiment, a viral genome may comprise two filler sequences, the first filler sequence may be located between the promoter region and payload region, and the second filler sequence may be located between the exon region and 3' ITR In one embodiment, a viral genome may comprise two filler sequences, the first filler sequence may be located between the promoter region and intron region, and the second filler sequence may be located between the payload region and intron region. In one embodiment, a viral genome may comprise two filler sequences, the first filler sequence may be located between the promoter region and intron region, and the second filler sequence may be located between the payload region and enhancer region. In one embodiment, a viral genome may comprise two filler sequences, the first filler sequence may be located between the promoter region and intron region, and the second filler sequence may be located between the payload region and polyadenylation signal sequence region. In one embodiment, a viral genome may comprise two filler sequences, the first filler sequence may be located between the promoter region and intron region, and the second filler sequence may be located between the payload region and MCS region. In one embodiment, a viral genome may comprise two filler sequences, the first filler sequence may be located between the promoter region and intron region, and the second filler sequence may be located between the payload region and exon region. In one embodiment, a viral genome may comprise two filler sequences, the first filler sequence may be located between the promoter region and intron region, and the second filler sequence may be located between the payload region and 3' ITR In one embodiment, a viral genome may comprise two filler sequences, the first filler sequence may be located between the promoter region and intron region, and the second filler sequence may be located between the intron region and enhancer region. In one embodiment, a viral genome may comprise two filler sequences, the first filler sequence may be located between the promoter region and intron region, and the second filler sequence may be located between the intron region and polyadenylation signal sequence region. In one embodiment, a viral genome may comprise two filler sequences, the first filler sequence may be located between the promoter region and intron region, and the second filler sequence may be located between the intron region and MCS region. In one embodiment, a viral genome may comprise two filler sequences, the first filler sequence may be located between the promoter region and intron region, and the second filler sequence may be located between the intron region and exon region. In one embodiment, a viral genome may comprise two filler sequences, the first filler sequence may be located between the promoter region and intron region, and the second filler sequence may be located between the intron region and 3' ITR. In one embodiment, a viral genome may comprise two filler sequences, the first filler sequence may be located between the promoter region and intron region, and the second filler sequence may be located between the enhancer region and polyadenylation signal sequence region. In one embodiment, a viral genome may comprise two filler sequences, the first filler sequence may be located between the promoter region and intron region, and the second filler sequence may be located between the enhancer region and MCS region. In one embodiment, a viral genome may comprise two filler sequences, the first filler sequence may be located between the promoter region and intron region, and the second filler sequence may be located between the enhancer region and exon region. In one embodiment, a viral genome may comprise two filler sequences, the first filler sequence may be located between the promoter region and intron region, and the second filler sequence may be located between the enhancer region and 3' ITR. In one embodiment, a viral genome may comprise two filler sequences, the first filler sequence may be located between the promoter region and intron region, and the second filler sequence may be located between the polyadenylation signal sequence region and MCS region. In one embodiment, a viral genome may comprise two filler sequences, the first filler sequence may be located between the promoter region and intron region, and the second filler sequence may be located between the polyadenylation signal sequence region and exon region. In one embodiment, a viral genome may comprise two filler sequences, the first filler sequence may be located between the promoter region and intron region, and the second filler sequence may be located between the polyadenylation signal sequence region and 3 ITR. In one embodiment, a viral genome may comprise two filler sequences, the first filler sequence may be located between the promoter region and intron region, and the second filler sequence may be located between the MCS region and exon region. In one embodiment, a viral genome may comprise two filler sequences, the first filler sequence may be located between the promoter region and intron region, and the second filler sequence may be located between the MCS region and 3' ITR. In one embodiment, a viral genome may comprise two filler sequences, the first filler sequence may be located between the promoter region and intron region, and the second filler sequence may be located between the exon region and 3' ITR.

In one embodiment, a viral genome may comprise two filler sequences, the first filler sequence may be located between the promoter region and enhancer region, and the second filler sequence may be located between the payload region and intron region. In one embodiment, a viral genome may comprise two filler sequences, the first filler sequence may be located between the promoter region and enhancer region, and the second filler sequence may be located between the payload region and enhancer region. In one embodiment, a viral genome may comprise two filler sequences, the first filler sequence may be located between the promoter region and enhancer region, and the second filler sequence may be located between the payload region and polyadenylation signal sequence region. In one embodiment, a viral genome may comprise two filler sequences, the first filler sequence may be located between the promoter region and enhancer region, and the second filler sequence may be located between the payload region and MCS region. In one embodiment, a viral genome may comprise two filler sequences, the first filler sequence may be located between the promoter region and enhancer region, and the second filler sequence may be located between the payload region and exon region. In one embodiment, a viral genome may comprise two filler sequences, the first filler sequence may be located between the promoter region and enhancer region, and the second filler sequence may be located between the payload region and 3' ITR. In one embodiment, a viral genome may comprise two filler sequences, the first filler sequence may be located between the promoter region and enhancer region, and the second filler sequence may be located between the intron region and enhancer region. In one embodiment, a viral genome may comprise two filler sequences, the first filler sequence may be located between the promoter region and enhancer region, and the second filler sequence may be located between the intron region and polyadenylation signal sequence region. In one embodiment, a viral genome may comprise two filler sequences, the first filler sequence may be located between the promoter region and enhancer region, and the second filler sequence may be located between the intron region and MCS region. In one embodiment, a viral genome may comprise two filler sequences, the first filler sequence may be located between the promoter region and enhancer region, and the second filler sequence may be located between the intron region and exon region. In one embodiment, a viral genome may comprise two filler sequences, the first filler sequence may be located between the promoter region and enhancer region, and the second filler sequence may be located between the intron region and 3' ITR. In one embodiment, a viral genome may comprise two filler sequences, the first filler sequence may be located between the promoter region and enhancer region, and the second filler sequence may be located between the enhancer region and polyadenylation signal sequence region. In one embodiment, a viral genome may comprise two filler sequences, the first filler sequence may be located between the promoter region and enhancer region, and the second filler sequence may be located between the enhancer region and MCS region. In one embodiment, a viral genome may comprise two filler sequences, the first filler sequence may be located between the promoter region and enhancer region, and the second filler sequence may be located between the enhancer region and exon region. In one embodiment, a viral genome may comprise two filler sequences, the first filler sequence may be located between the promoter region and enhancer region, and the second filler sequence may be located between the enhancer region and 3' ITR. In one embodiment, a viral genome may comprise two filler sequences, the first filler sequence may be located between the promoter region and enhancer region, and the second filler sequence may be located between the polyadenylation signal sequence region and MCS region. In one embodiment, a viral genome may comprise two filler sequences, the first filler sequence may be located between the promoter region and enhancer region, and the second filler sequence may be located between the polyadenylation signal sequence region and exon region. In one embodiment, a viral genome may comprise two filler sequences, the first filler sequence may be located between the promoter region and enhancer region, and the second filler sequence may be located between the polyadenylation signal sequence region and 3' ITR. In one embodiment, a viral genome may comprise two filler sequences, the first filler sequence may be located between the promoter region and enhancer region, and the second filler sequence may be located between the MCS region and exon region. In one embodiment, a viral genome may comprise two filler sequences, the first filler sequence may be located between the promoter region and enhancer region, and the second filler sequence may be located between the MCS region and 3' ITR. In one embodiment, a viral genome may comprise two filler sequences, the first filler sequence may be located between the promoter region and enhancer region, and the second filler sequence may be located between the exon region and 3' ITR.

In one embodiment, a viral genome may comprise two filler sequences, the first filler sequence may be located between the promoter region and polyadenylation signal sequence region, and the second filler sequence may be located between the payload region and intron region. In one embodiment, a viral genome may comprise two filler sequences, the first filler sequence may be located between the promoter region and polyadenylation signal sequence region, and the second filler sequence may be located between the payload region and enhancer region. In one embodiment, a viral genome may comprise two filler sequences, the first filler sequence may be located between the promoter region and polyadenylation signal sequence region, and the second filler sequence may be located between the payload region and polyadenylation signal sequence region. In one embodiment, a viral genome may comprise two filler sequences, the first filler sequence may be located between the promoter region and polyadenylation signal sequence region, and the second filler sequence may be located between the payload region and MCS region. In one embodiment, a viral genome may comprise two filler sequences, the first filler sequence may be located between the promoter region and polyadenylation signal sequence region, and the second filler sequence may be located between the payload region and exon region. In one embodiment, a viral genome may comprise two filler sequences, the first filler sequence may be located between the promoter region and polyadenylation signal sequence region, and the second filler sequence may be located between the payload region and 3' ITR. In one embodiment, a viral genome may comprise two filler sequences, the first filler sequence may be located between the promoter region and polyadenylation signal sequence region, and the second filler sequence may be located between the intron region and enhancer region. In one embodiment, a viral genome may comprise two filler sequences, the first filler sequence may be located between the promoter region and polyadenylation signal sequence region, and the second filler sequence may be located between the intron region and polyadenylation signal sequence region. In one embodiment, a viral genome may comprise two filler sequences, the first filler sequence may be located between the promoter region and polyadenylation signal sequence region, and the second filler sequence may be located between the intron region and MCS region. In one embodiment, a viral genome may comprise two filler sequences, the first filler sequence may be located between the promoter region and polyadenylation signal sequence region, and the second filler sequence may be located between the intron region and exon region. In one embodiment, a viral genome may comprise two filler sequences, the first filler sequence may be located between the promoter region and polyadenylation signal sequence region, and the second filler sequence may be located between the intron region and 3' ITR. In one embodiment, a viral genome may comprise two filler sequences, the first filler sequence may be located between the promoter region and polyadenylation signal sequence region, and the second filler sequence may be located between the enhancer region and polyadenylation signal sequence region. In one embodiment, a viral genome may comprise two filler sequences, the first filler sequence may be located between the promoter region and polyadenylation signal sequence region, and the second filler sequence may be located between the enhancer region and MCS region. In one embodiment, a viral genome may comprise two filler sequences, the first filler sequence may be located between the promoter region and polyadenylation signal sequence region, and the second filler sequence may be located between the enhancer region and exon region. In one embodiment, a viral genome may comprise two filler sequences, the first filler sequence may be located between the promoter region and polyadenylation signal sequence region, and the second filler sequence may be located between the enhancer region and 3' ITR. In one embodiment, a viral genome may comprise two filler sequences, the first filler sequence may be located between the promoter region and polyadenylation signal sequence region, and the second filler sequence may be located between the polyadenylation signal sequence region and MCS region. In one embodiment, a viral genome may comprise two filler sequences, the first filler sequence may be located between the promoter region and polyadenylation signal sequence region, and the second filler sequence may be located between the polyadenylation signal sequence region and exon region. In one embodiment, a viral genome may comprise two filler sequences, the first filler sequence may be located between the promoter region and polyadenylation signal sequence region, and the second filler sequence may be located between the polyadenylation signal sequence region and 3' ITR. In one embodiment, a viral genome may comprise two filler sequences, the first filler sequence may be located between the promoter region and polyadenylation signal sequence region, and the second filler sequence may be located between the MCS region and exon region. In one embodiment, a viral genome may comprise two filler sequences, the first filler sequence may be located between the promoter region and polyadenylation signal sequence region, and the second filler sequence may be located between the MCS region and 3' ITR. In one embodiment, a viral genome may comprise two filler sequences, the first filler sequence may be located between the promoter region and polyadenylation signal sequence region, and the second filler sequence may be located between the exon region and 3' ITR.

In one embodiment, a viral genome may comprise two filler sequences, the first filler sequence may be located between the promoter region and exon region, and the second filler sequence may be located between the payload region and intron region. In one embodiment, a viral genome may comprise two filler sequences, the first filler sequence may be located between the promoter region and exon region, and the second filler sequence may be located between the payload region and enhancer region. In one embodiment, a viral genome may comprise two filler sequences, the first filler sequence may be located between the promoter region and exon region, and the second filler sequence may be located between the payload region and polyadenylation signal sequence region. In one embodiment, a viral genome may comprise two filler sequences, the first filler sequence may be located between the promoter region and exon region, and the second filler sequence may be located between the payload region and MCS region. In one embodiment, a viral genome may comprise two filler sequences, the first filler sequence may be located between the promoter region and exon region, and the second filler sequence may be located between the payload region and exon region. In one embodiment, a viral genome may comprise two filler sequences, the first filler sequence may be located between the promoter region and exon region, and the second filler sequence may be located between the payload region and 3' ITR. In one embodiment, a viral genome may comprise two filler sequences, the first filler sequence may be located between the promoter region and exon region, and the second filler sequence may be located between the intron region and enhancer region. In one embodiment, a viral genome may comprise two filler sequences, the first filler sequence may be located between the promoter region and exon region, and the second filler sequence may be located between the intron region and polyadenylation signal sequence region. In one embodiment, a viral genome may comprise two filler sequences, the first filler sequence may be located between the promoter region and exon region, and the second filler sequence may be located between the intron region and MCS region. In one embodiment, a viral genome may comprise two filler sequences, the first filler sequence may be located between the promoter region and exon region, and the second filler sequence may be located between the intron region and exon region. In one embodiment, a viral genome may comprise two filler sequences, the first filler sequence may be located between the promoter region and exon region, and the second filler sequence may be located between the intron region and 3' ITR. In one embodiment, a viral genome may comprise two filler sequences, the first filler sequence may be located between the promoter region and exon region, and the second filler sequence may be located between the enhancer region and polyadenylation signal sequence region. In one embodiment, a viral genome may comprise two filler sequences, the first filler sequence may be located between the promoter region and exon region, and the second filler sequence may be located between the enhancer region and MCS region. In one embodiment, a viral genome may comprise two filler sequences, the first filler sequence may be located between the promoter region and exon region, and the second filler sequence may be located between the enhancer region and exon region. In one embodiment, a viral genome may comprise two filler sequences, the first filler sequence may be located between the promoter region and exon region, and the second filler sequence may be located between the enhancer region and 3' ITR. In one embodiment, a viral genome may comprise two filler sequences, the first filler sequence may be located between the promoter region and exon region, and the second filler sequence may be located between the polyadenylation signal sequence region and MCS region. In one embodiment, a viral genome may comprise two filler sequences, the first filler sequence may be located between the promoter region and exon region, and the second filler sequence may be located between the polyadenylation signal sequence region and exon region. In one embodiment, a viral genome may comprise two filler sequences, the first filler sequence may be located between the promoter region and exon region, and the second filler sequence may be located between the polyadenylation signal sequence region and 3 ITR. In one embodiment, a viral genome may comprise two filler sequences, the first filler sequence may be located between the promoter region and exon region, and the second filler sequence may be located between the MCS region and exon region. In one embodiment, a viral genome may comprise two filler sequences, the first filler sequence may be located between the promoter region and exon region, and the second filler sequence may be located between the MCS region and 3 ITR. In one embodiment, a viral genome may comprise two filler sequences, the first filler sequence may be located between the promoter region and exon region, and the second filler sequence may be located between the exon region and 3' ITR.

In one embodiment, a viral genome may comprise two filler sequences, the first filler sequence may be located between the promoter region and MCS region, and the second filler sequence may be located between the payload region and intron region. In one embodiment, a viral genome may comprise two filler sequences, the first filler sequence may be located between the promoter region and MCS region, and the second filler sequence may be located between the payload region and enhancer region. In one embodiment, a viral genome may comprise two filler sequences, the first filler sequence may be located between the promoter region and MCS region, and the second filler sequence may be located between the payload region and polyadenylation signal sequence region. In one embodiment, a viral genome may comprise two filler sequences, the first filler sequence may be located between the promoter region and MCS region, and the second filler sequence may be located between the payload region and MCS region. In one embodiment, a viral genome may comprise two filler sequences, the first filler sequence may be located between the promoter region and MCS region, and the second filler sequence may be located between the payload region and exon region. In one embodiment, a viral genome may comprise two filler sequences, the first filler sequence may be located between the promoter region and MCS region, and the second filler sequence may be located between the payload region and 3' ITR. In one embodiment, a viral genome may comprise two filler sequences, the first filler sequence may be located between the promoter region and MCS region, and the second filler sequence may be located between the intron region and enhancer region. In one embodiment, a viral genome may comprise two filler sequences, the first filler sequence may be located between the promoter region and MCS region, and the second filler sequence may be located between the intron region and polyadenylation signal sequence region. In one embodiment, a viral genome may comprise two filler sequences, the first filler sequence may be located between the promoter region and MCS region, and the second filler sequence may be located between the intron region and MCS region. In one embodiment, a viral genome may comprise two filler sequences, the first filler sequence may be located between the promoter region and MCS region, and the second filler sequence may be located between the intron region and exon region. In one embodiment, a viral genome may comprise two filler sequences, the first filler sequence may be located between the promoter region and MCS region, and the second filler sequence may be located between the intron region and 3' ITR. In one embodiment, a viral genome may comprise two filler sequences, the first filler sequence may be located between the promoter region and MCS region, and the second filler sequence may be located between the enhancer region and polyadenylation signal sequence region. In one embodiment, a viral genome may comprise two filler sequences, the first filler sequence may be located between the promoter region and MCS region, and the second filler sequence may be located between the enhancer region and MCS region. In one embodiment, a viral genome may comprise two filler sequences, the first filler sequence may be located between the promoter region and MCS region, and the second filler sequence may be located between the enhancer region and exon region. In one embodiment, a viral genome may comprise two filler sequences, the first filler sequence may be located between the promoter region and MCS region, and the second filler sequence may be located between the enhancer region and 3' ITR. In one embodiment, a viral genome may comprise two filler sequences, the first filler sequence may be located between the promoter region and MCS region, and the second filler sequence may be located between the polyadenylation signal sequence region and MCS region. In one embodiment, a viral genome may comprise two filler sequences, the first filler sequence may be located between the promoter region and MCS region, and the second filler sequence may be located between the polyadenylation signal sequence region and exon region. In one embodiment, a viral genome may comprise two filler sequences, the first filler sequence may be located between the promoter region and MCS region, and the second filler sequence may be located between the polyadenylation signal sequence region and 3' ITR. In one embodiment, a viral genome may comprise two filler sequences, the first filler sequence may be located between the promoter region and MCS region, and the second filler sequence may be located between the MCS region and exon region. In one embodiment, a viral genome may comprise two filler sequences, the first filler sequence may be located between the promoter region and MCS region, and the second filler sequence may be located between the MCS region and 3' ITR. In one embodiment, a viral genome may comprise two filler sequences, the first filler sequence may be located between the promoter region and MCS region, and the second filler sequence may be located between the exon region and 3' ITR.

In one embodiment, a viral genome may comprise two filler sequences, the first filler sequence may be located between the promoter region and 3' ITR, and the second filler sequence may be located between the payload region and intron region. In one embodiment, a viral genome may comprise two filler sequences, the first filler sequence may be located between the promoter region and 3' ITR, and the second filler sequence may be located between the payload region and enhancer region. In one embodiment, a viral genome may comprise two filler sequences, the first filler sequence may be located between the promoter region and 3' ITR, and the second filler sequence may be located between the payload region and polyadenylation signal sequence region. In one embodiment, a viral genome may comprise two filler sequences, the first filler sequence may be located between the promoter region and 3' ITR, and the second filler sequence may be located between the payload region and MCS region. In one embodiment, a viral genome may comprise two filler sequences, the first filler sequence may be located between the promoter region and 3' ITR, and the second filler sequence may be located between the payload region and exon region. In one embodiment, a viral genome may comprise two filler sequences, the first filler sequence may be located between the promoter region and 3' ITR, and the second filler sequence may be located between the payload region and 3' ITR. In one embodiment, a viral genome may comprise two filler sequences, the first filler sequence may be located between the promoter region and 3' ITR, and the second filler sequence may be located between the intron region and enhancer region. In one embodiment, a viral genome may comprise two filler sequences, the first filler sequence may be located between the promoter region and 3' ITR, and the second filler sequence may be located between the intron region and polyadenylation signal sequence region. In one embodiment, a viral genome may comprise two filler sequences, the first filler sequence may be located between the promoter region and 3' ITR, and the second filler sequence may be located between the intron region and MCS region. In one embodiment, a viral genome may comprise two filler sequences, the first filler sequence may be located between the promoter region and 3' ITR, and the second filler sequence may be located between the intron region and exon region. In one embodiment, a viral genome may comprise two filler sequences, the first filler sequence may be located between the promoter region and 3' ITR, and the second filler sequence may be located between the intron region and 3' ITR. In one embodiment, a viral genome may comprise two filler sequences, the first filler sequence may be located between the promoter region and 3' ITR, and the second filler sequence may be located between the enhancer region and polyadenylation signal sequence region. In one embodiment, a viral genome may comprise two filler sequences, the first filler sequence may be located between the promoter region and 3' ITR, and the second filler sequence may be located between the enhancer region and MCS region. In one embodiment, a viral genome may comprise two filler sequences, the first filler sequence may be located between the promoter region and 3' ITR, and the second filler sequence may be located between the enhancer region and exon region. In one embodiment, a viral genome may comprise two filler sequences, the first filler sequence may be located between the promoter region and 3' ITR, and the second filler sequence may be located between the enhancer region and 3' ITR. In one embodiment, a viral genome may comprise two filler sequences, the first filler sequence may be located between the promoter region and 3' ITR and the second filler sequence may be located between the polyadenylation signal sequence region and MCS region. In one embodiment, a viral genome may comprise two filler sequences, the first filler sequence may be located between the promoter region and 3' ITR, and the second filler sequence may be located between the polyadenylation signal sequence region and exon region. In one embodiment, a viral genome may comprise two filler sequences, the first filler sequence may be located between the promoter region and 3' ITR, and the second filler sequence may be located between the polyadenylation signal sequence region and 3' ITR. In one embodiment, a viral genome may comprise two filler sequences, the first filler sequence may be located between the promoter region and 3' ITR, and the second filler sequence may be located between the MCS region and exon region. In one embodiment, a viral genome may comprise two filler sequences, the first filler sequence may be located between the promoter region and 3' ITR, and the second filler sequence may be located between the MCS region and 3' ITR. In one embodiment, a viral genome may comprise two filler sequences, the first filler sequence may be located between the promoter region and 3' ITR, and the second filler sequence may be located between the exon region and 3' ITR.

In one embodiment, a viral genome may comprise two filler sequences, the first filler sequence may be located between the payload region and intron region, and the second filler sequence may be located between the intron region and enhancer region. In one embodiment, a viral genome may comprise two filler sequences, the first filler sequence may be located between the payload region and intron region, and the second filler sequence may be located between the intron region and polyadenylation signal sequence region. In one embodiment, a viral genome may comprise two filler sequences, the first filler sequence may be located between the payload region and intron region, and the second filler sequence may be located between the intron region and MCS region. In one embodiment, a viral genome may comprise two filler sequences, the first filler sequence may be located between the payload region and intron region, and the second filler sequence may be located between the intron region and exon region. In one embodiment, a viral genome may comprise two filler sequences, the first filler sequence may be located between the payload region and intron region, and the second filler sequence may be located between the intron region and 3' ITR. In one embodiment, a viral genome may comprise two filler sequences, the first filler sequence may be located between the payload region and intron region, and the second filler sequence may be located between the enhancer region and polyadenylation signal sequence region. In one embodiment, a viral genome may comprise two filler sequences, the first filler sequence may be located between the payload region and intron region, and the second filler sequence may be located between the enhancer region and MCS region. In one embodiment, a viral genome may comprise two filler sequences, the first filler sequence may be located between the payload region and intron region, and the second filler sequence may be located between the enhancer region and exon region. In one embodiment, a viral genome may comprise two filler sequences, the first filler sequence may be located between the payload region and intron region, and the second filler sequence may be located between the enhancer region and 3' ITR. In one embodiment, a viral genome may comprise two filler sequences, the first filler sequence may be located between the payload region and intron region, and the second filler sequence may be located between the polyadenylation signal sequence region and MCS region. In one embodiment, a viral genome may comprise two filler sequences, the first filler sequence may be located between the payload region and intron region, and the second filler sequence may be located between the polyadenylation signal sequence region and exon region. In one embodiment, a viral genome may comprise two filler sequences, the first filler sequence may be located between the payload region and intron region, and the second filler sequence may be located between the polyadenylation signal sequence region and 3' ITR. In one embodiment, a viral genome may comprise two filler sequences, the first filler sequence may be located between the payload region and intron region, and the second filler sequence may be located between the MCS region and exon region. In one embodiment, a viral genome may comprise two filler sequences, the first filler sequence may be located between the payload region and intron region, and the second filler sequence may be located between the MCS region and 3' ITR. In one embodiment, a viral genome may comprise two filler sequences, the first filler sequence may be located between the payload region and intron region, and the second filler sequence may be located between the exon region and 3' ITR.

In one embodiment, a viral genome may comprise two filler sequences, the first filler sequence may be located between the payload region and enhancer region, and the second filler sequence may be located between the intron region and enhancer region. In one embodiment, a viral genome may comprise two filler sequences, the first filler sequence may be located between the payload region and enhancer region, and the second filler sequence may be located between the intron region and polyadenylation signal sequence region. In one embodiment, a viral genome may comprise two filler sequences, the first filler sequence may be located between the payload region and enhancer region, and the second filler sequence may be located between the intron region and MCS region. In one embodiment, a viral genome may comprise two filler sequences, the first filler sequence may be located between the payload region and enhancer region, and the second filler sequence may be located between the intron region and exon region. In one embodiment, a viral genome may comprise two filler sequences, the first filler sequence may be located between the payload region and enhancer region, and the second filler sequence may be located between the intron region and 3' ITR. In one embodiment, a viral genome may comprise two filler sequences, the first filler sequence may be located between the payload region and enhancer region, and the second filler sequence may be located between the enhancer region and polyadenylation signal sequence region. In one embodiment, a viral genome may comprise two filler sequences, the first filler sequence may be located between the payload region and enhancer region, and the second filler sequence may be located between the enhancer region and MCS region. In one embodiment, a viral genome may comprise two filler sequences, the first filler sequence may be located between the payload region and enhancer region, and the second filler sequence may be located between the enhancer region and exon region. In one embodiment, a viral genome may comprise two filler sequences, the first filler sequence may be located between the payload region and enhancer region, and the second filler sequence may be located between the enhancer region and 3' ITR. In one embodiment, a viral genome may comprise two filler sequences, the first filler sequence may be located between the payload region and enhancer region, and the second filler sequence may be located between the polyadenylation signal sequence region and MCS region. In one embodiment, a viral genome may comprise two filler sequences, the first filler sequence may be located between the payload region and enhancer region, and the second filler sequence may be located between the polyadenylation signal sequence region and exon region. In one embodiment, a viral genome may comprise two filler sequences, the first filler sequence may be located between the payload region and enhancer region, and the second filler sequence may be located between the polyadenylation signal sequence region and 3' ITR. In one embodiment, a viral genome may comprise two filler sequences, the first filler sequence may be located between the payload region and enhancer region, and the second filler sequence may be located between the MCS region and exon region. In one embodiment, a viral genome may comprise two filler sequences, the first filler sequence may be located between the payload region and enhancer region, and the second filler sequence may be located between the MCS region and 3' ITR. In one embodiment, a viral genome may comprise two filler sequences, the first filler sequence may be located between the payload region and enhancer region, and the second filler sequence may be located between the exon region and 3' ITR.

In one embodiment, a viral genome may comprise two filler sequences, the first filler sequence may be located between the payload region and polyadenylation signal sequence region, and the second filler sequence may be located between the intron region and enhancer region. In one embodiment, a viral genome may comprise two filler sequences, the first filler sequence may be located between the payload region and polyadenylation signal sequence region, and the second filler sequence may be located between the intron region and polyadenylation signal sequence region. In one embodiment, a viral genome may comprise two filler sequences, the first filler sequence may be located between the payload region and polyadenylation signal sequence region, and the second filler sequence may be located between the intron region and MCS region. In one embodiment, a viral genome may comprise two filler sequences, the first filler sequence may be located between the payload region and polyadenylation signal sequence region, and the second filler sequence may be located between the intron region and exon region. In one embodiment, a viral genome may comprise two filler sequences, the first filler sequence may be located between the payload region and polyadenylation signal sequence region, and the second filler sequence may be located between the intron region and 3' ITR. In one embodiment, a viral genome may comprise two filler sequences, the first filler sequence may be located between the payload region and polyadenylation signal sequence region, and the second filler sequence may be located between the enhancer region and polyadenylation signal sequence region. In one embodiment, a viral genome may comprise two filler sequences, the first filler sequence may be located between the payload region and polyadenylation signal sequence region, and the second filler sequence may be located between the enhancer region and MCS region. In one embodiment, a viral genome may comprise two filler sequences, the first filler sequence may be located between the payload region and polyadenylation signal sequence region, and the second filler sequence may be located between the enhancer region and exon region. In one embodiment, a viral genome may comprise two filler sequences, the first filler sequence may be located between the payload region and polyadenylation signal sequence region, and the second filler sequence may be located between the enhancer region and 3 ITR. In one embodiment, a viral genome may comprise two filler sequences, the first filler sequence may be located between the payload region and polyadenylation signal sequence region, and the second filler sequence may be located between the polyadenylation signal sequence region and MCS region. In one embodiment, a viral genome may comprise two filler sequences, the first filler sequence may be located between the payload region and polyadenylation signal sequence region, and the second filler sequence may be located between the polyadenylation signal sequence region and exon region. In one embodiment, a viral genome may comprise two filler sequences, the first filler sequence may be located between the payload region and polyadenylation signal sequence region, and the second filler sequence may be located between the polyadenylation signal sequence region and 3' ITR. In one embodiment, a viral genome may comprise two filler sequences, the first filler sequence may be located between the payload region and polyadenylation signal sequence region, and the second filler sequence may be located between the MCS region and exon region. In one embodiment, a viral genome may comprise two filler sequences, the first filler sequence may be located between the payload region and polyadenylation signal sequence region, and the second filler sequence may be located between the MCS region and 3 ITR. In one embodiment, a viral genome may comprise two filler sequences, the first filler sequence may be located between the payload region and polyadenylation signal sequence region, and the second filler sequence may be located between the exon region and 3' ITR.

In one embodiment, a viral genome may comprise two filler sequences, the first filler sequence may be located between the payload region and MCS region, and the second filler sequence may be located between the intron region and enhancer region. In one embodiment, a viral genome may comprise two filler sequences, the first filler sequence may be located between the payload region and MCS region, and the second filler sequence may be located between the intron region and polyadenylation signal sequence region. In one embodiment, a viral genome may comprise two filler sequences, the first filler sequence may be located between the payload region and MCS region, and the second filler sequence may be located between the intron region and MCS region. In one embodiment, a viral genome may comprise two filler sequences, the first filler sequence may be located between the payload region and MCS region, and the second filler sequence may be located between the intron region and exon region. In one embodiment, a viral genome may comprise two filler sequences, the first filler sequence may be located between the payload region and MCS region, and the second filler sequence may be located between the intron region and 3' ITR. In one embodiment, a viral genome may comprise two filler sequences, the first filler sequence may be located between the payload region and MCS region, and the second filler sequence may be located between the enhancer region and polyadenylation signal sequence region. In one embodiment, a viral genome may comprise two filler sequences, the first filler sequence may be located between the payload region and MCS region, and the second filler sequence may be located between the enhancer region and MCS region. In one embodiment, a viral genome may comprise two filler sequences, the first filler sequence may be located between the payload region and MCS region, and the second filler sequence may be located between the enhancer region and exon region. In one embodiment, a viral genome may comprise two filler sequences, the first filler sequence may be located between the payload region and MCS region, and the second filler sequence may be located between the enhancer region and 3 ITR. In one embodiment, a viral genome may comprise two filler sequences, the first filler sequence may be located between the payload region and MCS region, and the second filler sequence may be located between the polyadenylation signal sequence region and MCS region. In one embodiment, a viral genome may comprise two filler sequences, the first filler sequence may be located between the payload region and MCS region, and the second filler sequence may be located between the polyadenylation signal sequence region and exon region. In one embodiment, a viral genome may comprise two filler sequences, the first filler sequence may be located between the payload region and MCS region, and the second filler sequence may be located between the polyadenylation signal sequence region and 3' ITR. In one embodiment, a viral genome may comprise two filler sequences, the first filler sequence may be located between the payload region and MCS region, and the second filler sequence may be located between the MCS region and exon region. In one embodiment, a viral genome may comprise two filler sequences, the first filler sequence may be located between the payload region and MCS region, and the second filler sequence may be located between the MCS region and 3' ITR. In one embodiment, a viral genome may comprise two filler sequences, the first filler sequence may be located between the payload region and MCS region, and the second filler sequence may be located between the exon region and 3' ITR.

In one embodiment, a viral genome may comprise two filler sequences, the first filler sequence may be located between the payload region and exon region, and the second filler sequence may be located between the intron region and enhancer region. In one embodiment, a viral genome may comprise two filler sequences, the first filler sequence may be located between the payload region and exon region, and the second filler sequence may be located between the intron region and polyadenylation signal sequence region. In one embodiment, a viral genome may comprise two filler sequences, the first filler sequence may be located between the payload region and exon region, and the second filler sequence may be located between the intron region and MCS region. In one embodiment, a viral genome may comprise two filler sequences, the first filler sequence may be located between the payload region and exon region, and the second filler sequence may be located between the intron region and exon region. In one embodiment, a viral genome may comprise two filler sequences, the first filler sequence may be located between the payload region and exon region, and the second filler sequence may be located between the intron region and 3' ITR. In one embodiment, a viral genome may comprise two filler sequences, the first filler sequence may be located between the payload region and exon region, and the second filler sequence may be located between the enhancer region and polyadenylation signal sequence region. In one embodiment, a viral genome may comprise two filler sequences, the first filler sequence may be located between the payload region and exon region, and the second filler sequence may be located between the enhancer region and MCS region. In one embodiment, a viral genome may comprise two filler sequences, the first filler sequence may be located between the payload region and exon region, and the second filler sequence may be located between the enhancer region and exon region. In one embodiment, a viral genome may comprise two filler sequences, the first filler sequence may be located between the payload region and exon region, and the second filler sequence may be located between the enhancer region and 3 ITR. In one embodiment, a viral genome may comprise two filler sequences, the first filler sequence may be located between the payload region and exon region, and the second filler sequence may be located between the polyadenylation signal sequence region and MCS region. In one embodiment, a viral genome may comprise two filler sequences, the first filler sequence may be located between the payload region and exon region, and the second filler sequence may be located between the polyadenylation signal sequence region and exon region. In one embodiment, a viral genome may comprise two filler sequences, the first filler sequence may be located between the payload region and exon region, and the second filler sequence may be located between the polyadenylation signal sequence region and 3' ITR. In one embodiment, a viral genome may comprise two filler sequences, the first filler sequence may be located between the payload region and exon region, and the second filler sequence may be located between the MCS region and exon region. In one embodiment, a viral genome may comprise two filler sequences, the first filler sequence may be located between the payload region and exon region, and the second filler sequence may be located between the MCS region and 3' ITR. In one embodiment, a viral genome may comprise two filler sequences, the first filler sequence may be located between the payload region and exon region, and the second filler sequence may be located between the exon region and 3' ITR.

In one embodiment, a viral genome may comprise two filler sequences, the first filler sequence may be located between the payload region and 3' ITR region, and the second filler sequence may be located between the intron region and enhancer region. In one embodiment, a viral genome may comprise two filler sequences, the first filler sequence may be located between the payload region and 3' ITR region, and the second filler sequence may be located between the intron region and polyadenylation signal sequence region. In one embodiment, a viral genome may comprise two filler sequences, the first filler sequence may be located between the payload region and 3' ITR region, and the second filler sequence may be located between the intron region and MCS region. In one embodiment, a viral genome may comprise two filler sequences, the first filler sequence may be located between the payload region and 3' ITR region, and the second filler sequence may be located between the intron region and exon region. In one embodiment, a viral genome may comprise two filler sequences, the first filler sequence may be located between the payload region and 3' ITR region, and the second filler sequence may be located between the intron region and 3' ITR. In one embodiment, a viral genome may comprise two filler sequences, the first filler sequence may be located between the payload region and 3' ITR region, and the second filler sequence may be located between the enhancer region and polyadenylation signal sequence region. In one embodiment, a viral genome may comprise two filler sequences, the first filler sequence may be located between the payload region and 3' ITR region, and the second filler sequence may be located between the enhancer region and MCS region. In one embodiment, a viral genome may comprise two filler sequences, the first filler sequence may be located between the payload region and 3' ITR region, and the second filler sequence may be located between the enhancer region and exon region. In one embodiment, a viral genome may comprise two filler sequences, the first filler sequence may be located between the payload region and 3' ITR region, and the second filler sequence may be located between the enhancer region and 3' ITR. In one embodiment, a viral genome may comprise two filler sequences, the first filler sequence may be located between the payload region and 3' ITR region, and the second filler sequence may be located between the polyadenylation signal sequence region and MCS region. In one embodiment, a viral genome may comprise two filler sequences, the first filler sequence may be located between the payload region and 3' ITR region, and the second filler sequence may be located between the polyadenylation signal sequence region and exon region. In one embodiment, a viral genome may comprise two filler sequences, the first filler sequence may be located between the payload region and 3' ITR region, and the second filler sequence may be located between the polyadenylation signal sequence region and 3' ITR. In one embodiment, a viral genome may comprise two filler sequences, the first filler sequence may be located between the payload region and 3' ITR region, and the second filler sequence may be located between the MCS region and exon region. In one embodiment, a viral genome may comprise two filler sequences, the first filler sequence may be located between the payload region and 3' ITR region, and the second filler sequence may be located between the MCS region and 3' ITR. In one embodiment, a viral genome may comprise two filler sequences, the first filler sequence may be located between the payload region and 3' ITR region, and the second filler sequence may be located between the exon region and 3' ITR.

In one embodiment, a viral genome may comprise two filler sequences, the first filler sequence may be located between the intron region and enhancer region, and the second filler sequence may be located between the enhancer region and polyadenylation signal sequence region. In one embodiment, a viral genome may comprise two filler sequences, the first filler sequence may be located between the intron region and enhancer region, and the second filler sequence may be located between the enhancer region and MCS region. In one embodiment, a viral genome may comprise two filler sequences, the first filler sequence may be located between the intron region and enhancer region, and the second filler sequence may be located between the enhancer region and exon region. In one embodiment, a viral genome may comprise two filler sequences, the first filler sequence may be located between the intron region and enhancer region, and the second filler sequence may be located between the enhancer region and 3' ITR. In one embodiment, a viral genome may comprise two filler sequences, the first filler sequence may be located between the intron region and enhancer region, and the second filler sequence may be located between the polyadenylation signal sequence region and MCS region. In one embodiment, a viral genome may comprise two filler sequences, the first filler sequence may be located between the intron region and enhancer region, and the second filler sequence may be located between the polyadenylation signal sequence region and exon region. In one embodiment, a viral genome may comprise two filler sequences, the first filler sequence may be located between the intron region and enhancer region, and the second filler sequence may be located between the polyadenylation signal sequence region and 3' ITR. In one embodiment, a viral genome may comprise two filler sequences, the first filler sequence may be located between the intron region and enhancer region, and the second filler sequence may be located between the MCS region and exon region. In one embodiment, a viral genome may comprise two filler sequences, the first filler sequence may be located between the intron region and enhancer region, and the second filler sequence may be located between the MCS region and 3' ITR. In one embodiment, a viral genome may comprise two filler sequences, the first filler sequence may be located between the intron region and enhancer region, and the second filler sequence may be located between the exon region and 3' ITR.

In one embodiment, a viral genome may comprise two filler sequences, the first filler sequence may be located between the intron region and polyadenylation signal sequence region, and the second filler sequence may be located between the enhancer region and polyadenylation signal sequence region. In one embodiment, a viral genome may comprise two filler sequences, the first filler sequence may be located between the intron region and polyadenylation signal sequence region, and the second filler sequence may be located between the enhancer region and MCS region. In one embodiment, a viral genome may comprise two filler sequences, the first filler sequence may be located between the intron region and polyadenylation signal sequence region, and the second filler sequence may be located between the enhancer region and exon region. In one embodiment, a viral genome may comprise two filler sequences, the first filler sequence may be located between the intron region and polyadenylation signal sequence region, and the second filler sequence may be located between the enhancer region and 3' ITR. In one embodiment, a viral genome may comprise two filler sequences, the first filler sequence may be located between the intron region and polyadenylation signal sequence region, and the second filler sequence may be located between the polyadenylation signal sequence region and MCS region. In one embodiment, a viral genome may comprise two filler sequences, the first filler sequence may be located between the intron region and polyadenylation signal sequence region, and the second filler sequence may be located between the polyadenylation signal sequence region and exon region. In one embodiment, a viral genome may comprise two filler sequences, the first filler sequence may be located between the intron region and polyadenylation signal sequence region, and the second filler sequence may be located between the polyadenylation signal sequence region and 3' ITR. In one embodiment, a viral genome may comprise two filler sequences, the first filler sequence may be located between the intron region and polyadenylation signal sequence region, and the second filler sequence may be located between the MCS region and exon region. In one embodiment, a viral genome may comprise two filler sequences, the first filler sequence may be located between the intron region and polyadenylation signal sequence region, and the second filler sequence may be located between the MCS region and 3' ITR. In one embodiment, a viral genome may comprise two filler sequences, the first filler sequence may be located between the intron region and polyadenylation signal sequence region, and the second filler sequence may be located between the exon region and 3' ITR.

In one embodiment, a viral genome may comprise two filler sequences, the first filler sequence may be located between the intron region and MCS region, and the second filler sequence may be located between the enhancer region and polyadenylation signal sequence region. In one embodiment, a viral genome may comprise two filler sequences, the first filler sequence may be located between the intron region and MCS region, and the second filler sequence may be located between the enhancer region and MCS region. In one embodiment, a viral genome may comprise two filler sequences, the first filler sequence may be located between the intron region and MCS region, and the second filler sequence may be located between the enhancer region and exon region. In one embodiment, a viral genome may comprise two filler sequences, the first filler sequence may be located between the intron region and MCS region, and the second filler sequence may be located between the enhancer region and 3' ITR. In one embodiment, a viral genome may comprise two filler sequences, the first filler sequence may be located between the intron region and MCS region, and the second filler sequence may be located between the polyadenylation signal sequence region and MCS region. In one embodiment, a viral genome may comprise two filler sequences, the first filler sequence may be located between the intron region and MCS region, and the second filler sequence may be located between the polyadenylation signal sequence region and exon region. In one embodiment, a viral genome may comprise two filler sequences, the first filler sequence may be located between the intron region and MCS region, and the second filler sequence may be located between the polyadenylation signal sequence region and 3' ITR. In one embodiment, a viral genome may comprise two filler sequences, the first filler sequence may be located between the intron region and MCS region, and the second filler sequence may be located between the MCS region and exon region. In one embodiment, a viral genome may comprise two filler sequences, the first filler sequence may be located between the intron region and MCS region, and the second filler sequence may be located between the MCS region and 3' ITR. In one embodiment, a viral genome may comprise two filler sequences, the first filler sequence may be located between the intron region and MCS region, and the second filler sequence may be located between the exon region and 3' ITR.

In one embodiment, a viral genome may comprise two filler sequences, the first filler sequence may be located between the intron region and exon region, and the second filler sequence may be located between the enhancer region and polyadenylation signal sequence region. In one embodiment, a viral genome may comprise two filler sequences, the first filler sequence may be located between the intron region and exon region, and the second filler sequence may be located between the enhancer region and MCS region. In one embodiment, a viral genome may comprise two filler sequences, the first filler sequence may be located between the intron region and exon region, and the second filler sequence may be located between the enhancer region and exon region. In one embodiment, a viral genome may comprise two filler sequences, the first filler sequence may be located between the intron region and exon region, and the second filler sequence may be located between the enhancer region and 3' ITR. In one embodiment, a viral genome may comprise two filler sequences, the first filler sequence may be located between the intron region and exon region, and the second filler sequence may be located between the polyadenylation signal sequence region and MCS region. In one embodiment, a viral genome may comprise two filler sequences, the first filler sequence may be located between the intron region and exon region, and the second filler sequence may be located between the polyadenylation signal sequence region and exon region. In one embodiment, a viral genome may comprise two filler sequences, the first filler sequence may be located between the intron region and exon region, and the second filler sequence may be located between the polyadenylation signal sequence region and 3' ITR. In one embodiment, a viral genome may comprise two filler sequences, the first filler sequence may be located between the intron region and exon region, and the second filler sequence may be located between the MCS region and exon region. In one embodiment, a viral genome may comprise two filler sequences, the first filler sequence may be located between the intron region and exon region, and the second filler sequence may be located between the MCS region and 3' ITR. In one embodiment, a viral genome may comprise two filler sequences, the first filler sequence may be located between the intron region and exon region, and the second filler sequence may be located between the exon region and 3' ITR.

In one embodiment, a viral genome may comprise two filler sequences, the first filler sequence may be located between the intron region and 3' ITR, and the second filler sequence may be located between the enhancer region and polyadenylation signal sequence region. In one embodiment, a viral genome may comprise two filler sequences, the first filler sequence may be located between the intron region and 3' ITR, and the second filler sequence may be located between the enhancer region and MCS region. In one embodiment, a viral genome may comprise two filler sequences, the first filler sequence may be located between the intron region and 3' ITR, and the second filler sequence may be located between the enhancer region and exon region. In one embodiment, a viral genome may comprise two filler sequences, the first filler sequence may be located between the intron region and 3' ITR, and the second filler sequence may be located between the enhancer region and 3' ITR. In one embodiment, a viral genome may comprise two filler sequences, the first filler sequence may be located between the intron region and 3' ITR, and the second filler sequence may be located between the polyadenylation signal sequence region and MCS region. In one embodiment, a viral genome may comprise two filler sequences, the first filler sequence may be located between the intron region and 3' ITR, and the second filler sequence may be located between the polyadenylation signal sequence region and exon region. In one embodiment, a viral genome may comprise two filler sequences, the first filler sequence may be located between the intron region and 3' ITR, and the second filler sequence may be located between the polyadenylation signal sequence region and 3' ITR. In one embodiment, a viral genome may comprise two filler sequences, the first filler sequence may be located between the intron region and 3' ITR, and the second filler sequence may be located between the MCS region and exon region. In one embodiment, a viral genome may comprise two filler sequences, the first filler sequence may be located between the intron region and 3' ITR, and the second filler sequence may be located between the MCS region and 3' ITR. In one embodiment, a viral genome may comprise two filler sequences, the first filler sequence may be located between the intron region and 3' ITR, and the second filler sequence may be located between the exon region and 3' ITR.

In one embodiment, a viral genome may comprise two filler sequences, the first filler sequence may be located between the enhancer region and polyadenylation signal sequence region, and the second filler sequence may be located between the polyadenylation signal sequence region and MCS region. In one embodiment, a viral genome may comprise two filler sequences, the first filler sequence may be located between the enhancer region and polyadenylation signal sequence region, and the second filler sequence may be located between the polyadenylation signal sequence region and exon region. In one embodiment, a viral genome may comprise two filler sequences, the first filler sequence may be located between the enhancer region and polyadenylation signal sequence region, and the second filler sequence may be located between the polyadenylation signal sequence region and 3' ITR. In one embodiment, a viral genome may comprise two filler sequences, the first filler sequence may be located between the enhancer region and polyadenylation signal sequence region, and the second filler sequence may be located between the MCS region and exon region. In one embodiment, a viral genome may comprise two filler sequences, the first filler sequence may be located between the enhancer region and polyadenylation signal sequence region, and the second filler sequence may be located between the MCS region and 3' ITR. In one embodiment, a viral genome may comprise two filler sequences, the first filler sequence may be located between the enhancer region and polyadenylation signal sequence region, and the second filler sequence may be located between the exon region and 3' ITR.

In one embodiment, a viral genome may comprise two filler sequences, the first filler sequence may be located between the enhancer region and MCS region, and the second filler sequence may be located between the polyadenylation signal sequence region and MCS region. In one embodiment, a viral genome may comprise two filler sequences, the first filler sequence may be located between the enhancer region and MCS region, and the second filler sequence may be located between the polyadenylation signal sequence region and exon region. In one embodiment, a viral genome may comprise two filler sequences, the first filler sequence may be located between the enhancer region and MCS region, and the second filler sequence may be located between the polyadenylation signal sequence region and 3' ITR. In one embodiment, a viral genome may comprise two filler sequences, the first filler sequence may be located between the enhancer region and MCS region, and the second filler sequence may be located between the MCS region and exon region. In one embodiment, a viral genome may comprise two filler sequences, the first filler sequence may be located between the enhancer region and MCS region, and the second filler sequence may be located between the MCS region and 3' ITR. In one embodiment, a viral genome may comprise two filler sequences, the first filler sequence may be located between the enhancer region and MCS region, and the second filler sequence may be located between the exon region and 3' ITR.

In one embodiment, a viral genome may comprise two filler sequences, the first filler sequence may be located between the enhancer region and exon region, and the second filler sequence may be located between the polyadenylation signal sequence region and MCS region. In one embodiment, a viral genome may comprise two filler sequences, the first filler sequence may be located between the enhancer region and exon region, and the second filler sequence may be located between the polyadenylation signal sequence region and exon region. In one embodiment, a viral genome may comprise two filler sequences, the first filler sequence may be located between the enhancer region and exon region, and the second filler sequence may be located between the polyadenylation signal sequence region and 3' ITR. In one embodiment, a viral genome may comprise two filler sequences, the first filler sequence may be located between the enhancer region and exon region, and the second filler sequence may be located between the MCS region and exon region. In one embodiment, a viral genome may comprise two filler sequences, the first filler sequence may be located between the enhancer region and exon region, and the second filler sequence may be located between the MCS region and 3' ITR. In one embodiment, a viral genome may comprise two filler sequences, the first filler sequence may be located between the enhancer region and exon region, and the second filler sequence may be located between the exon region and 3' ITR.

In one embodiment, a viral genome may comprise two filler sequences, the first filler sequence may be located between the enhancer region and 3' ITR, and the second filler sequence may be located between the polyadenylation signal sequence region and MCS region. In one embodiment, a viral genome may comprise two filler sequences, the first filler sequence may be located between the enhancer region and 3' ITR, and the second filler sequence may be located between the polyadenylation signal sequence region and exon region. In one embodiment, a viral genome may comprise two filler sequences, the first filler sequence may be located between the enhancer region and 3' ITR, and the second filler sequence may be located between the polyadenylation signal sequence region and 3' ITR. In one embodiment, a viral genome may comprise two filler sequences, the first filler sequence may be located between the enhancer region and 3' ITR, and the second filler sequence may be located between the MCS region and exon region. In one embodiment, a viral genome may comprise two filler sequences, the first filler sequence may be located between the enhancer region and 3' ITR, and the second filler sequence may be located between the MCS region and 3' ITR. In one embodiment, a viral genome may comprise two filler sequences, the first filler sequence may be located between the enhancer region and 3' ITR, and the second filler sequence may be located between the exon region and 3' ITR.

In one embodiment, a viral genome may comprise two filler sequences, the first filler sequence may be located between the polyadenylation signal sequence region and MCS region, and the second filler sequence may be located between the MCS region and exon region. In one embodiment, a viral genome may comprise two filler sequences, the first filler sequence may be located between the polyadenylation signal sequence region and MCS region, and the second filler sequence may be located between the MCS region and 3' ITR. In one embodiment, a viral genome may comprise two filler sequences, the first filler sequence may be located between the polyadenylation signal sequence region and MCS region, and the second filler sequence may be located between the exon region and 3' ITR.

In one embodiment, a viral genome may comprise two filler sequences, the first filler sequence may be located between the polyadenylation signal sequence region and exon region, and the second filler sequence may be located between the MCS region and exon region. In one embodiment, a viral genome may comprise two filler sequences, the first filler sequence may be located between the polyadenylation signal sequence region and exon region, and the second filler sequence may be located between the MCS region and 3' ITR. In one embodiment, a viral genome may comprise two filler sequences, the first filler sequence may be located between the polyadenylation signal sequence region and exon region, and the second filler sequence may be located between the exon region and 3' ITR.

In one embodiment, a viral genome may comprise two filler sequences, the first filler sequence may be located between the polyadenylation signal sequence region and 3' ITR, and the second filler sequence may be located between the MCS region and exon region. In one embodiment, a viral genome may comprise two filler sequences, the first filler sequence may be located between the polyadenylation signal sequence region and 3' ITR, and the second filler sequence may be located between the MCS region and 3' ITR In one embodiment, a viral genome may comprise two filler sequences, the first filler sequence may be located between the polyadenylation signal sequence region and 3' ITR, and the second filler sequence may be located between the exon region and 3' ITR.

In one embodiment, a viral genome may comprise two filler sequences, the first filler sequence may be located between the MCS region and exon region, and the second filler sequence may be located between the exon region and 3' ITR.

Genome Size

In one embodiment, the AAV particle which comprises a payload described herein may be single stranded or double stranded vector genome. The size of the vector genome may be small, medium, large or the maximum size. Additionally, the vector genome may comprise a promoter and a polyA tail.

In one embodiment, the vector genome which comprises a payload described herein may be a small single stranded vector genome. A small single stranded vector genome may be 2.7 to 3.5 kb in size such as about 2.7, 2.8, 2.9, 3.0, 3.1, 3.2, 3.3, 3.4, and 3.5 kb in size. As a non-limiting example, the small single stranded vector genome may be 3.2 kb in size. Additionally, the vector genome may comprise a promoter and a polyA tail.

In one embodiment, the vector genome which comprises a payload described herein may be a small double stranded vector genome. A small double stranded vector genome may be 1.3 to 1.7 kb in size such as about 1.3, 1.4, 1.5, 1.6, and 1.7 kb in size. As a non-limiting example, the small double stranded vector genome may be 1.6 kb in size. Additionally, the vector genome may comprise a promoter and a polyA tail.

In one embodiment, the vector genome which comprises a payload described herein may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. As a non-limiting example, the medium single stranded vector genome may be 4.0 kb in size. Additionally, the vector genome may comprise a promoter and a polyA tail.

In one embodiment, the vector genome which comprises a payload described herein may be a medium double stranded vector genome. A medium double stranded vector genome may be 1.8 to 2.1 kb in size such as about 1.8, 1.9, 2.0, and 2.1 kb in size. As a non-limiting example, the medium double stranded vector genome may be 2.0 kb in size. Additionally, the vector genome may comprise a promoter and a polyA tail.

In one embodiment, the vector genome which comprises a payload described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size. Additionally, the vector genome may comprise a promoter and a polyA tail.

In one embodiment, the vector genome which comprises a payload described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size. Additionally, the vector genome may comprise a promoter and a polyA tail.

Payloads

The AAV particles of the present disclosure comprise at least one payload region. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid. Payloads of the present disclosure typically encode polypeptides or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In one embodiment, the AAV particle comprises a viral genome with a payload region comprising nucleic acid sequences encoding more than one polypeptide of interest. In such an embodiment, a viral genome encoding more than one polypeptide may be replicated and packaged into a viral particle. A target cell transduced with a viral particle comprising more than one polypeptide may express each of the polypeptides in a single cell.

In one embodiment, the payload region may comprise the following components: a payload region located within the viral genome; at least one inverted terminal repeat (ITR) at the 5' and/or the 3' end of the payload region; and a promoter region, an intron region and a coding region within the payload region.

Where the AAV particle payload region encodes a polypeptide, the polypeptide may be a peptide or protein. The viral genomes encoding polypeptides described herein may be useful in the fields of human disease, viruses, infections veterinary applications and a variety of in vivo and in vitro settings.

In some embodiments, the AAV particles are useful in the field of medicine for the treatment, prophylaxis, palliation or amelioration of neurological diseases and/or disorders.

In some embodiments, the AAV particles are useful in the field of medicine for the treatment, prophylaxis, palliation or amelioration of Parkinson's Disease.

In some embodiments, the AAV particles are useful in the field of medicine for the treatment, prophylaxis, palliation or amelioration of diseases of the central nervous system.

The Nature of the Polypeptides and Variants

Amino acid sequences encoded by payload regions of the viral genomes of the disclosure may be translated as a whole polypeptide, a plurality of polypeptides or fragments of polypeptides, which independently may be encoded by one or more nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multimolecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably at least about 90% homologous to a native sequence. "Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

Sequence tags or amino acids, such as one or more lysines, can be added to the peptide sequences of the disclosure (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present disclosure.

Other post-translational modifications include hydroxylation of proline and lysine, phosphorylation of hydroxyl groups of seryl or threonyl residues, methylation of the alpha-amino groups of lysine, arginine, and histidine side chains, glycosylation/glycation, and the introduction of disulfide bonds (such as disulfide bonds between cysteine residues) (T. E. Creighton, Proteins: Structure and Molecular Properties, W.H. Freeman & Co., San Francisco, pp. 79-86 (1983)).

"Features" when referring to proteins are defined as distinct amino acid sequence-based components of a molecule. Features of the proteins of the present disclosure include surface manifestations, local conformational shape, folds, loops, half-loops, domains, half-domains, sites, termini or any combination thereof.

As used herein when referring to proteins the term "surface manifestation" refers to a polypeptide-based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol Biol 266 (4): 814-830; 1997).

As used herein when referring to proteins the term "half-loop" refers to a portion of an identified loop having at least half the number of amino acid residues as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions).

As used herein when referring to proteins the term "half-domain" means portion of an identified domain having at least half the number of amino acid residues as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present disclosure.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present disclosure may be characterized as having both an N-terminus (terminated by an amino acid with a free amino group (NH2)) and a C-terminus (terminated by an amino acid with a free carboxyl group (COOH)). Proteins of the disclosure are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide-based moiety such as an organic conjugate.

Once any of the features have been identified or defined as a component of a molecule of the disclosure, any of several manipulations and/or modifications of these features may be performed by moving, swapping, inverting, deleting, randomizing or duplicating. Furthermore, it is understood that manipulation of features may result in the same outcome as a modification to the molecules of the disclosure. For example, a manipulation which involves deleting a domain would result in the alteration of the length of a molecule just as modification of a nucleic acid to encode less than a full-length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Payload: AADC Polynucleotide Constructs

According to the present disclosure, aromatic L-amino acid decarboxylase (AADC; also known as dopa decarboxylase and DDC) polynucleotides are provided which function alone or in combination with additional nucleic acid sequence(s) to encode the AADC protein. As used herein an "AADC polynucleotide" is any nucleic acid polymer which encodes an AADC protein and when present in a vector, plasmid or translatable construct, expresses such AADC protein in a cell, tissue, organ or organism.

AADC polynucleotides include precursor molecules which are processed inside the cell. AADC polynucleotides or the processed forms thereof may be encoded in a plasmid, vector, genome or other nucleic acid expression vector for delivery to a cell.

In some embodiments AADC polynucleotides are designed as components of AAV viral genomes and packaged in AAV particles which are processed within the cell to produce the wild type AADC protein.

In some embodiments, the AADC polynucleotide may be the payload of the AAV particle.

As used herein, the wild type AADC protein may be any of the naturally occurring isoforms or variants from the DDC gene. Multiple alternatively spliced transcript variants encoding different isoforms of AADC have been identified. Specifically, the DDC gene produces seven transcript variants that encode six distinct isoforms. DDC transcript variants 1 and 2 both encode AADC isoform 1. In some embodiments, the AADC polynucleotides encode DDC transcript variant 2, thereby encoding a native AADC isoform 1 (NCBI Reference Sequence: NP_000781.1). This sequence is given here:

```
                                          (SEQ ID NO: 1)
MNASEFRRRGKEMVDYVANYMEGIEGRQVYPDVEPGYLRPLIPAAAPQE

PDTFEDIINDVEKIIMPGVTHWHSPYFFAYFPTASSYPAMLADMLCGAI

GCIGFSWAASPACTELETVMMDWLGKMLELPKAFLNEKAGEGGGVIQGS

ASEATLVALLAARTKVIHRLQAASPELTQAAIMEKLVAYSSDQAHSSVE

RAGLIGGVKLKAIPSDGNFAMRASALQEALERDKAAGLIPFFMVATLGT

TTCCSFDNLLEVGPICNKEDIWLHVDAAYAGSAFICPEFRHLLNGVEFA

DSFNFNPHKWLLVNFDCSAMWVKKRTDLTGAFRLDPTYLKHSHQDSGLI

TDYRHWQIPLGRRFRSLKMWFVFRMYGVKGLQAYIRKHVQLSHEFESLV

RQDPRFEICVEVILGLVCFRLKGSNKVNEALLQRINSAKKIHLVPCHLR

DKFVLRFAICSRTVESAHVQRAWEHIKELAADVLRAERE
```

The AADC polynucleotides of the disclosure, may be engineered to contain modular elements and/or sequence motifs assembled to create AADC polynucleotide constructs.

According to the present disclosure, AADC polynucleotides are provided. Such polynucleotides comprise nucleic acid polymers which comprise a region of linked nucleosides encoding one or more isoforms or variants of the AADC protein.

In some embodiments, the AADC polynucleotide comprises a codon optimized transcript encoding an AADC protein.

In some embodiments, the AADC polynucleotide comprises a sequence region encoding one or more wild type isoforms or variants of an AADC protein. Such polynucleotides may also comprise a sequence region encoding any one or more of the following: a 5' ITR, a cytomegalovirus (CMV) Enhancer, a CMV Promoter, an ie1 exon 1, an ie1 intron1, an hbBglobin intron2, an hBglobin exon 3, a 5' UTR, a 3' UTR, an hGH poly(A) signal, and/or a 3' ITR. Such sequence regions are taught herein or may be any of those known in the art.

In some embodiments, the AADC polynucleotide comprises a SEQ ID NO: 2 or a fragment or variant thereof.

Component regions of an AADC polynucleotide comprising SEQ ID NO: 2 are presented in Table 1.

TABLE 1

Component regions of AADC polynucleotides

AADC Polynucleotide (SEQ ID NO: 2)

| Region | Start | Stop | Length of Region | SEQ ID NO of region |
|---|---|---|---|---|
| 5' ITR | 1 | 141 | 141 | 3 |
| MCS | 189 | 206 | 18 | 4 |
| CMV enhancer | 213 | 515 | 303 | 5 |
| CMV promoter | 516 | 719 | 204 | 6 |
| Ie1 exon 1 | 734 | 867 | 134 | 7 |
| Ie1 intron partial | 868 | 899 | 32 | 8 |
| hBglobin intron 2 | 900 | 1246 | 347 | 9 |
| hBglobin exon 3 | 1247 | 1299 | 53 | 10 |
| AADC | 1338 | 2777 | 1440 | 11 |
| MCS | 2820 | 2837 | 18 | 12 |
| Poly(A) | 2838 | 3314 | 477 | 13 |
| 3' ITR | 3386 | 3526 | 141 | 14 |

In one embodiment, the AADC polynucleotide comprises a sequence which has a percent identity to any of SEQ ID NO: 2 or a fragment or variant thereof. The AADC polynucleotide may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NO: 2 or a fragment or variant thereof. The AADC polynucleotide may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NO: 2 or a fragment or variant thereof. As a non-limiting example, the AADC polynucleotide comprises a sequence which as 80% identity to any of SEQ ID NO: 2 or a fragment or variant thereof. As another non-limiting example, the AADC polynucleotide comprises a sequence which as 85% identity to any of SEQ ID NO: 2 or a fragment or variant thereof. As another non-limiting example, the AADC polynucleotide comprises a sequence which as 90% identity to any of SEQ ID NO: 2 or a fragment or variant thereof. As another non-limiting example, the AADC polynucleotide comprises a sequence which as 95% identity to any of SEQ ID NO: 2 or a fragment or variant thereof. As another non-limiting example, the AADC polynucleotide comprises a sequence which as 99% identity to any of SEQ ID NO: 2 or a fragment or variant thereof.

In some embodiments, the coding region of the AADC polynucleotide is 1440 nucleotides in length. Such an AADC polynucleotide may be codon optimized over all or a portion of the polynucleotide.

In some embodiments, the AADC polynucleotide comprises any of SEQ ID NO: 2 or a fragment or variant thereof but lacking the 5' and/or 3' ITRs. Such a polynucleotide may be incorporated into a plasmid or vector and utilized to express the encoded AADC protein.

In one embodiment, the AADC polynucleotides may be produced in insect cells (e.g., Sf9 cells).

In one embodiment, the AADC polynucleotides may be produced using triple transfection.

In one embodiment, the AADC polynucleotide may comprise a codon optimized open reading frame of an AADC mRNA, at least one 5' ITR and at least one 3'UTR where the one or more of the 5' ITRs may be located at the 5' end of the promoter region and one or more 3' ITRs may be located at the 3' end of the poly(A) signal. The AADC mRNA may comprise a promoter region, a 5' untranslated region (UTR), a 3'UTR and a poly(A) signal. The promoter region may include, but is not limited to, enhancer element, a promoter element, a first exon region, a first intron region, a second intron region and a second exon region. As a non-limiting example, the enhancer element and the promoter element are derived from CMV. As another non-limiting example, the first exon region is ie1 exon 1 or fragments thereof, the first intron region is ie1 intron 1 or fragments thereof, the second intron region is hbBglobin intron 2 or fragments thereof and the second exon region is hbBglobin exon 3 or fragments thereof. As yet another non-limiting example, the poly(A) signal is derived from human growth hormone.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as promoters.

In one embodiment, the AADC polynucleotide is encoded in a plasmid or vector, which may be derived from an adeno-associated virus (AAV). The AAV may comprise a capsid serotype such as, but not limited to, PHP.B, PHP.A, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11. AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5. AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV1 14.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60. AAV161.6/hu.61, AAV33.12/hu.17, AAV33.4/hu.15, AAV33.8/hu.16, AAV52/hu.19. AAV52.l/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3. AAVpi.2. AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3. AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58. AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17. AAVrb.18, AAVrh.19, AAVrh.20, AAVrh.21, AAVrh.22, AAVrb.23. AAVrh.24, AAVrh.25, AAVrh.31, AAVrh.32, AAVrh.33, AAVrh.34, AAVrh.35, AAVrh.36, AAVrh.37. AAVrh.37R2, AAVrh.38. AAVrh.39, AAVrh.40, AAVrh.46, AAVrh.48, AAVrh.48.1, AAVrh.48.1.2, AAVrh.48.2, AAVrh.49, AAVrh.51. AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R. AAVrh8R A586R mutant, AAVrh8R R533A mutant, AAAV, BAAV, caprine AAV, bovine AAV, AAVhE1.1. AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13. AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b. AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53. AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10. AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5. AAV CHt-6.6, AAV CHt-6.7, AAV CHt-6.8, AAV CHt-P1, AAV CHt-P2. AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3. AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7. AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6. AAVF7/HSC7, AAVF8/HSC8, AAVF9/HSC9, PHP.B (AAV-PHP.B), PHP.A (AAV.PHP.A), G2B-26, G2B-13, TH1.1-32, TH1.1-35, AAVPHP.B2, AAVPHP.B3, AAVPHP.N/PHP.B-DGT, AAVPHP.B-EST, AAVPHP.B-GGT, AAVPHP.B-ATP, AAVPHP.B-ATF-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, and/or AAVG2B5, and variants thereof.

II. Production and Analysis

In certain embodiments, the recombinant adeno-associated virus, serotype 2 (AAV2) carrying the complementary deoxyribonucleic acid (cDNA) of the human aromatic L-amino acid decarboxylase (hAADC) gene are under the control of the cytomegalovirus (CMV) immediate early promoter.

Production of the vector involves infection of Sf9 cells with two BV infected insect cells (BIICs) to generate recombinant adeno-associated virus (rAAV2)-hAADC vector. In certain embodiments, the BIICs is selected from BIIC-rep2/cap2, BIIC-hAADC, or BIIC:BIIC:VCD.

The vector is composed of four molecular species: the three viral proteins (VP1, VP2 and VP3) that form the vector capsid and the therapeutic deoxyribonucleic acid (DNA) packaged into the capsid consisting of the transgene expression cassette flanked by the AAV2 inverted terminal repeat elements (ITRs). Alternatively, the vectors are produced using a HEK293/triple-transfected (TTx) system.

Alternatively, HT1080 cells are transduced with AAV2 for production of AADC. AAV2 is hypothesized to enter through heparin sulfate-mediated binding, which is thought to be similar between neuronal cell lines and the HT1080 cell line (Plochmann et al. JVI 2012). Further, HT1080 cells have undetectable levels of endogenous AADC similar to post-synaptic neurons, which results in a large and accurate assay window with transgenically expressed hAADC. In certain embodiments, a TT/HEK293 system was used for producing AADC.

In some embodiments, cells are transduced with a viral vector encoding a protein of interest. In some embodiments, the viral vector is a parvovirus vector. In some embodiments, the parvovirus vector is an AAV vector. In some embodiments the protein of interest is AADC, for example, human AADC. The amino acid sequence of AADC, for example, human AADC is well known. For example, the amino acid sequence of UniProtKB/Swiss-Prot P20711.2 is a representative amino acid sequence of human AADC. In some embodiments, the viral vector is an AAV2 AADC vector, or AAV2.AADC vector. In some embodiments, the AADC viral vector is transduced into the cells at a concentration of about 1 vg/cell to about $1\times10^8$ vg/cell. In some embodiments, the AADC viral vector is transduced into the cells at a concentration of about 10 vg/cell to about $1\times10^5$ vg/cell. In some embodiments, the AADC viral vector is transduced into the cells at a concentration of about 1 vg/cell to about $1\times10^7$ vg/cell. In some embodiments, the AADC viral vector is transduced into the cells at a concentration of about 11 vg/cell to about $1\times10^6$ vg/cell. In some embodiments, the AADC viral vector is transduced into the cells at a concentration of about 1 vg/cell to about $1\times10^5$ vg/cell. In some embodiments, the AADC viral vector is transduced into the cells at a concentration of about 100 vg/cell to about $1\times10^6$ vg/cell. In some embodiments, the AADC viral vector is transduced into the cells at a concentration of about 100 vg/cell to about $1\times10^5$ vg/cell. In some embodiments, the AADC viral vector is transduced into the cells at a concentration of about 10 vg/cell to about $1\times10^6$ vg/cell. In some embodiments, the AADC viral vector is transduced into the cells at a concentration of about 10 vg/cell to about $1\times10^3$ vg/cell. In some embodiments, the AADC viral vector is transduced into the cells at a concentration of about 10 vg/cell to about $1\times10^2$ vg/cell. In some embodiments, the AADC viral vector is transduced into the cells at a concentration of about 100 vg/cell to about $1\times10^4$ vg/cell. In some embodiments, the AADC viral vector is transduced into the cells at a concentration of about 100 vg/cell to about $1\times10^3$ vg/cell. In some embodiments, the AADC viral vector is transduced into the cells at a concentration of about 1 vg/cell, about 10 vg/cell, about 100 vg/cell, about $1\times10^3$ vg/cell, about $1\times10^4$ vg/cell about $1\times10^5$ vg/cell, about $1\times10^6$ vg/cell about $1\times10^7$ vg/cell, or about $1\times10^8$ vg/

In some embodiments, HT1080 cells are plated at a density of about $3\times10^2$ cells/cm$^2$ to about $3\times10^8$ cells/cm$^2$, about $3\times10^2$ cells/cm$^2$ to about $3\times10^7$ cells/cm$^2$, about $3\times10^2$ cells/cm$^2$ to about $3\times10^6$ cells/cm$^2$, about $3\times10^2$ cells/cm$^2$ to about $3\times10^5$ cells/cm$^2$, about $3\times10^2$ cells/cm$^2$ to about $3\times10^4$ cells/cm$^2$, about $3\times10^2$ cells/cm$^2$ to about $3\times10^3$ cells/cm$^2$, about $3\times10^3$ cells/cm$^2$ to about $3\times10^4$ cells/cm$^2$, about $3\times10^3$ cells/cm$^2$ to about $3\times10^5$ cells/cm$^2$, about $3\times10^3$ cells/cm$^2$ to about $3\times10^6$ cells/cm$^2$, about $3\times10^4$ cells/cm$^2$ to about $3\times10^6$ cells/cm$^2$, or about $3\times10^5$ cells/cm$^2$ to about $3\times10^7$ cells/cm$^2$. In some embodiments, the HT1080 cells are plated at a density of about $3\times10^4$ cells/cm$^2$.

In some embodiments, cells are plated at a density of about $1\times10^2$ cells/well to about $1\times10^8$ cells/well, about $1\times10^2$ cells/well to about $1\times10^7$ cells/well, about $1\times10^2$ cells/well to about $1\times10^6$ cells/well, about $1\times10^2$ cells/well to about $1\times10^5$ cells/well, about $1\times10^2$ cells/well to about $1\times10^4$ cells/well, about $1\times10^2$ cells/well to about $1\times10^3$ cells/well, about $1\times10^3$ cells/well to about $1\times10^4$ cells/well, about $1\times10^2$ cells/well to about $1\times10^5$ cells/well, about $1\times10^3$ cells/well to about $1\times10^6$ cells/well, about $1\times10^4$ cells/well to about $1\times10^6$ cells/well, or about $1\times10^5$ cells/ well to about 1×10⁷ cells/well. In some embodiments, the HT1080 cells are plated at a density of about 1×10⁴ cells/well.

In some embodiments, HT1080 cells are plated at a density of about 1×10² cells/well to about 1×10⁸ cells/well, about 1×10² cells/well to about 1×10⁷ cells/well, about 1×10² cells/well to about 1×10⁶ cells/well, about 1×10² cells/well to about 1×10⁵ cells/well, about 1×10² cells/well to about 1×10⁴ cells/well, about 1×10² cells/well to about 1×10³ cells/well, about 1×10³ cells/well to about 1×10⁴ cells/well, about 1×10³ cells/well to about 1×10⁵ cells/well, about 1×10³ cells/well to about 1×10⁶ cells/well, about 1×10⁴ cells/well to about 1×10⁶ cells/well, or about 1×10⁵ cells/well to about 1×10⁷ cells/well. In some embodiments, the HT1080 cells are plated at a density of about 1×10⁴ cells/well. In some embodiments, HT1080 cells were plated at a density of 5×10³ cells/well. In some embodiments, the cells are incubated at 37±2° C. for 24+2 hours.

In some embodiments, cells are transduced with a viral vector, for example, AAV vector, encoding a protein of interest, lysed, and cell lysate is collected. In some embodiments, cells are transduced with a viral vector, for example, AAV vector, encoding a protein of interest and harvested after about 18 to about 72 hours post transduction. In some embodiments, the cells are harvested after 24 hours post transduction. In some embodiments, the cells are harvested after about 24 to about 44 hours post transduction. In some embodiments, the cells are harvested after about 44 to about 52 hours post transduction. In some embodiments, the cells are harvested after about 52 to about 72 hours post transduction.

In some embodiments, the cells are lysed using chemical and/or mechanical lysis. In some embodiments, the chemical lysis comprises a lysis buffer comprising a protease inhibitor, phosphate buffered saline and Triton X100. In some embodiments, the cells can be frozen after the addition of the lysis buffer at −80'C for about 30 minutes to about 72 hours. Alternatively, the cell lysate may be stored in a range of 2 to 8° C. or at room temperature. In some embodiments, the cells are centrifuged and cell lysates are collected. In some embodiments, this is performed by spinning the cells in a centrifuge at 3,750 RPM for 10 minutes at room temperature.

In some embodiments, the present application provides a method for measuring AADC potency, comprising adding L-DOPA to a cell lysate produced from cells transduced with a viral vector comprising a polynucleotide encoding AADC and measuring the amount of dopamine produced in the cell lysate after the AADC reaction with L-DOPA.

In some embodiments, the cell lysates comprise AADC produced from the cells transduced with the AAV2.AADC vector. In some embodiments, L-DOPA and/or an AADC reaction buffer are added to the cell lysates. In some embodiments L-DOPA is converted to dopamine via an AADC reaction with L-DOPA.

In some embodiments, the AADC reaction buffer comprises a phosphate buffer, such as sodium phosphate buffer, e.g., 50 mM sodium phosphate buffer. In some embodiments, the AADC reaction buffer comprises 50 mM sodium phosphate buffer, ascorbic acid, pyridoxal-5'-phosphate DL-dithiothreitol, EDTA, and pargyline. In some embodiments, the AADC reaction buffer comprises 50 mM sodium phosphate buffer, pH 7.2; 0.1 mM ascorbic acid, 0.1 mM pyridoxal-5'-phosphate, 1 mM DL-dithiothreitol, 0.1 mM EDTA, and 0.1 mM pargyline. In some embodiments, the AADC reaction buffer comprises octanesulfonic acid sodium salt, sodium phosphate monobasic, and acetonitrile. In some embodiments, the AADC reaction buffer comprises 3.0 mM octanesulfonic acid sodium salt, pH 3.0, 72.5 mM sodium phosphate monobasic (NaH2PO4), and 10% acetonitrile. In some embodiments, the AADC reaction buffer comprises 3.2 mM octanesulfonic acid sodium salt, pH 3.0, 72.5 mM sodium phosphate monobasic (NaH2P04), and 10% acetonitrile. In some embodiments, L-DOPA is added to the cell lysate at a concentration of about 0.01 mM to about 1 mM. In some embodiments, L-DOPA is added to the cell lysate at a concentration of about 0.03 mM.

In some embodiments, the AADC reaction with L-DOPA is carried out at 37° C. In some embodiments, the AADC reaction with L-DOPA is carried out for 10-120 minutes. In some embodiments, the AADC reaction with L-DOPA is carried out for 30 minutes. In some embodiments, the AADC reaction with L-DOPA is carried out for 30 minutes and the cell lysates are transferred to 2-8° C., to reduce the rate of conversion and minimize the variation between samples. In some embodiments, the AADC reaction with L-DOPA is carried out at room temperature.

In some embodiments, the AADC reaction with L-DOPA is quenched by adding ice-cold perchloric acid. In some embodiments, the ice-cold perchloric acid is added at a concentration of 0.1 M to 1 M. In some embodiments, the ice-cold perchloric acid is added at a concentration of 0.5 M.

In some embodiments, the amount of dopamine produced is measured using Ultra High-Performance Liquid Chromatography with an Electrochemical Detector ("UHPLC-ECD"). In some embodiments, the amount of dopamine produced is measured using UHPLC-ECD by comparing the amount of dopamine to a dopamine standard curve.

The present application also provides a method for measuring AADC viral vector potency comprising adding L-DOPA to a cell lysate produced from cells transduced with a first viral vector comprising a polynucleotide encoding AADC, measuring the amount of dopamine produced in the cell lysate after an AADC reaction with L-DOPA, and comparing the amount of dopamine produced to that produced when a viral vector reference standard is utilized, such that the potency of the first viral vector is measured.

In some embodiments, the viral vector reference standard provides an appropriate range for the viral vector's potency method described above. In some embodiments, cells are transduced with a range of vector genomes per cell or vg/µl, the cells are lysed as described above, and activity of the molecule of interest is determined. In some embodiments, a dose response is plotted (dopamine v. vector genomes per cell or vg/µl). In some embodiments, the range of the vector genomes per cell are between about 10 to about 10,000 vector genomes per cell. In some embodiments, the range of the vector genomes per cell comprises doses evenly spaced by performing 2-fold serial dilutions of the highest dose.

In some embodiments, the present disclosure refers to methods of selecting viral vectors having a desired potency. In some embodiments, the amount of dopamine produced in the cell lysate after the AADC reaction with L-DOPA is higher than the amount of dopamine produced when a viral reference standard is utilized, indicating that the first viral vector is more potent than the viral vector reference. In some embodiments, the amount of dopamine produced in the cell lysate after the AADC reaction with L-DOPA is lower than the amount of dopamine produced when a viral reference standard is utilized, indicating that the first viral vector is less potent than the viral vector reference. In some embodiments, the amount of dopamine produced in the cell lysate after the AADC reaction with L-DOPA is about equal to the amount of dopamine produced when a viral reference standard is utilized, indicating that the first viral vector is about equally potent than the viral vector reference.

In certain embodiments, the methods described herein can further comprise use of a positive control comprising a viral vector lot monitored for values within a defined acceptable range. If an assay run results in the values from the positive control that are outside the acceptable range, the assay run can be declared invalid. Such a positive control can provide benefit as a validity or acceptance criterion.

The methods described herein can be performed by utilizing any of a wide range cell assay formats, including, but not limited to cell plates, e.g., 24-well plates, 48-well plates, 96-well plates, or 384-well plates, individual cell culture plates, or flasks, for example T-flasks or shaker flasks.

In some embodiments, data is analyzed using four parameter logistic regression analysis according to the following equation:

$$\text{Absorbance} = D + \frac{A - D}{1 + \left(\frac{\text{Concentration}}{C}\right)^B};$$

where A is the upper asymptote ("Top"); B is the slope of dynamic range ("Hillslope"); C is the $EC_{50}$; and D is the lower asymptote ("Bottom"). In some embodiments, a dose response curve is fit to a four-parameter curve analysis. In some embodiments, the relative potency of different samples can be expressed as a value or a shift in the half-maximal effective concentration (EC50) according to four-parameter curve analysis. The linearity of the method allows for accurate comparison of batch to batch potency, ensuring consistency.

In some embodiments, data is analyzed for relative potency, which can be expressed as a shift in $EC_{50}$ from the reference standard. AADC Relative Potency can be expressed as the ratio of the $EC_{50}$ values of the Reference Standard to the Test Sample using the following equation:

$$\text{Relative Potency} = \left(\frac{EC50_{REFERENCE}}{EC50_{TEST\ SAMPLE}}\right) \times 100\%$$

In some embodiments, an AADC vector has an AADC Relative Potency of 1-5%, 5-10%, 10-15%, 15-20%, 20-25%, 25-30%, 30-35%, 3540%, 4045%, 45-50%, 50-55%, 55-60%, 60-65%, 65-70%, 70-75%, 75-80%, 80-85%, 85-90%, 90-95%, 95-100%, 100-105%, 105-110%, 110-115%, 115-120%, 120-125%, 125-130%, 130-135%0, 135-140%, 140-145%, 145-150%, 150-155%, 155-160%, 160-165%, 165-170%, 170-175%, 175-180%, 180-185%, 185-190%, 190-195%, 195-200%.

In some embodiments, the AADC Relative Potency of an AADC vector is compared to a threshold AADC Relative Potency value. In some embodiments, an AADC vector is discarded or abandoned if it falls below a threshold AADC Relative Potency value. In some embodiments, an AADC viral vector is included in an AAV formulation, and the AAV formulation is not aliquoted into a formulation container if the AADC Relative Potency of the AADC viral vector falls below the threshold AADC Relative Potency value. In certain embodiments, the threshold AADC Relative Potency value is 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200%.

In some embodiments, assays of the present disclosure can be used to measure and/or compare the enzymatic activity of AADC vectors produced by different methods. In some embodiments, assays of the present disclosure can be used to measure and/or compare the enzymatic activity of AADC vectors produced in different volumes. In some embodiments, assays of the present disclosure can be used to measure the enzymatic activity of AADC vectors produced at a scale between about 10 L and about 5000 L, between about 50 L and about 4000 L, between about 100 L and about 3000 L, or between about 20 L and about 2000 L scale. In some embodiments, assays of the present disclosure can be used to measure the enzymatic activity of AADC vectors produced at a scale of about 10 L, about 25 L, about 50 L, about 75 L, about 100 L, about 150 L, about 200 L, about 250 L, about 500 L, about 750 L, about 1000 L, about 1500 L, about 2000 L, about 3000 L, about 4000 L, and about 5000 L.

While not wishing to be bound by theory, the potency assay described herein provides a method by which to evaluate transgene (e.g., AADC) expression in a biologically relevant context.

The assay is envisioned as utilizing the in vitro transduction of an immortalized cell line (HT1080 cells) with a dose range of vector expressing AADC. The lysates would then be used to enzymatically convert L-DOPA to dopamine. The production of dopamine can be monitored by UHPLC (or HPLC) followed by electrochemical detection ("UHPLC-ECD") of the oxidation of the dihydroxyaromatic ring in L-DOPA and dopamine. Alternatively, the production of dopamine can be monitored by the range of doses will then be fit to a non-linear curve. The samples will be tested relative to a reference using the fit parameters. Alternatively, UHPLC-UV is used to measure the production of dopamine. In certain embodiments, the doses range from 32 µM to 320 µM.

The conversion of L-DOPA to dopamine using AADC has been previously demonstrated in the literature (Ciesielska et al. 2015). Harvested tissue lysates expressing AADC were used to convert L-DOPA to dopamine, including the reagents/cofactors and reaction conditions needed for the conversion. Measurement of this conversion using HPLC-ECD.

Accuracy of the potency assay described herein may be influenced by initial measurements of viral vector titer. Accurate, precise and reproducible titers ensure more accurate, precise and reproducible potency readouts and can further be used to ensure confidence in experimental or clinical dosing. Titer and potency data, when combined, may serve to further inform one of skill in the art to viral vector characteristics and proper dosing parameters for enhanced efficacy and safety. Multiple measurements of titer and potency may further increase accuracy and precision in lot to lot comparisons and long-term stability studies.

Methods of making AAV particles are well known in the art and are described in e.g., United States Patent Nos. U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597: Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir,* 63:3822-8 (1989); Kajigaya et al., *Proc. Nat'l. Acad. Sci. USA* 88: 4646-50 (1991); Ruffing et al., *J. Vir,* 66:6922-30 (1992); Kimbauer et al., *Vir.,* 219:37-44 (1996); Zhao et al., *Vir,* 272:382-93 (2000); the contents of each of which are herein incorporated by reference in their entirety. In one embodiment, the AAV particles are made using the methods described in WO2015191508, the contents of which are herein incorporated by reference in their entirety.

Viral replication cells commonly used for production of recombinant AAV particles include but are not limited to 293 cells, COS cells, HeLa cells, KB cells, and other mammalian cell lines as described in U.S. Pat. Nos. U.S. Pat. Nos. 6,156,303, 5,387,484, 5,741,683, 5,691,176, and 5,688,676; U.S. patent publication No. 2002/0081721, and International Patent Publication Nos. WO 00/47757, WO 00/24916, and WO 96/17947, the contents of each of which are herein incorporated by reference in their entireties.

In certain embodiments, the present disclosure provides an assay which utilizes the in vitro transduction of an immortalized cell line (HT-1080; human fibrosarcoma cells) with a MOI dose range of AAV2-AADC. The lysates are then used to enzymatically convert L-DOPA to dopamine. The production of dopamine can be monitored by UHPLC (or HPLC) followed by ultraviolet (UV) detection or electrochemical detection (ECD) of the aromatic ring present in L-DOPA and dopamine. The range of MOI doses and their corresponding dopamine values can be fit to a non-linear four parameter curve. The test samples can be assessed relative to a vector reference using the four parameter fit data to determine relative potency.

In some embodiments, the present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, and 5) harvesting and purifying the AAV particle comprising a viral genome.

In some embodiments, the present disclosure provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

In some embodiments, the present disclosure includes a method of producing a gene therapy product, which can include the following steps: (a) providing an AAV formulation comprising an AAV vector, (b) measuring viral vector potency of the AAV formulation using methods or systems of the present disclosure; and (c) suitably aliquoting the AAV formulation into a formulation container after the viral vector potency has been measured. In some embodiments, the AAV viral vector includes a viral genome. In some embodiments, the AAV vector includes an AADC polynucleotide encoding aromatic L-amino acid decarboxylase (AADC). In some embodiments, the viral vector potency of the AAV formulation being measured is AADC viral vector potency.

In some embodiments, the present disclosure includes a method of producing a gene therapy product, which can include the following steps: (a) suitably aliquoting an AAV formulation into a formulation container, wherein the AAV formulation comprises an AAV vector, and wherein the viral vector potency of the formulation has been measured using methods or systems of the present disclosure prior to the AAV formulation being aliquoted into the formulation container. In some embodiments, the AAV vector includes a viral genome. In some embodiments, the AAV vector includes an AADC polynucleotide encoding aromatic L-amino acid decarboxylase (AADC). In some embodiments, the viral vector potency of the AAV formulation being measured is AADC viral vector potency.

In some embodiments, the viral genome of the AAV particle of the disclosure optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes as described in International application No. WO 96/23810: Heim et al., Current Biology 2:178-182 (1996): Heim et al., Proc. Natl. Acad. Sci. USA (1995); or Heim et al., Science 373:663-664 (1995): WO 96/30540, the contents of each of which are incorporated herein by reference in their entireties).

III. Formulations and Compositions

Pharmaceutical Compositions

According to the present disclosure the AAV particles may be prepared as pharmaceutical compositions. It will be understood that such compositions necessarily comprise one or more active ingredients and, most often, a pharmaceutically acceptable excipient.

Relative amounts of the active ingredient (e.g. AAV particle), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.0001% and 99% (w/w) of the active ingredient. By way of example, the composition may comprise between 0.0001% and 100%, e.g., between 0.5 and 50%, between 1-30%, between 5-80%, at least 80% (w/w) active ingredient.

In some embodiments, the AAV particle pharmaceutical compositions described herein may comprise at least one payload. As a non-limiting example, the pharmaceutical compositions may contain an AAV particle with 1, 2, 3, 4 or 5 payloads.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients or subjects.

Formulations

Formulations of the present disclosure can include, without limitation, saline, liposomes, lipid nanoparticles, polymers, peptides, proteins, cells transfected with AAV particles (e.g., for transfer or transplantation into a subject) and combinations thereof.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general, such preparatory methods include the step of associating the active ingredient with an excipient and/or one or more other accessory ingredients. As used herein, the phrase "active ingredient" generally refers either to an AAV particle carrying a payload region encoding the polypeptides of the disclosure or to the end product encoded by a viral genome of by an AAV particle as described herein.

Formulations of the AAV particles and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In one embodiment, the AAV particles of the disclosure may be formulated in PBS, in combination with an ethylene oxide/propylene oxide copolymer (also known as pluronic or poloxamer).

In one embodiment, the AAV particles of the disclosure may be formulated in PBS with 0.001% pluronic acid (F-68) (poloxamer 188) at a pH of about 7.0.

In one embodiment, the AAV particles of the disclosure may be formulated in PBS with 0.001% pluronic acid (F-68) (poloxamer 188) at a pH of about 7.3.

In one embodiment, the AAV particles of the disclosure may be formulated in PBS with 0.001% pluronic acid (F-68) (poloxamer 188) at a pH of about 7.4.

In one embodiment, the AAV particles of the disclosure may be formulated in a solution comprising sodium chloride, sodium phosphate and an ethylene oxide/propylene oxide copolymer.

In one embodiment, the AAV particles of the disclosure may be formulated in a solution comprising sodium chloride, sodium phosphate dibasic, sodium phosphate monobasic and poloxamer 188/pluronic acid (F-68).

In one embodiment, the AAV particles of the disclosure may be formulated in a solution comprising about 180 mM sodium chloride, about 10 mM sodium phosphate and about 0.001% poloxamer 188, at a pH of about 7.3. The concentration of sodium chloride in the final solution may be 150 mM-200 mM. As non-limiting examples, the concentration of sodium chloride in the final solution may be 150 mM, 160 mM, 170 mM, 180 mM, 190 mM or 200 mM. The concentration of sodium phosphate in the final solution may be 1 mM-50 mM. As non-limiting examples, the concentration of sodium phosphate in the final solution may be 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, or 50 mM. The concentration of poloxamer 188 (pluronic acid (F-68)) may be 0.0001%-1%. As non-limiting examples, the concentration of poloxamer 188 (pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In one embodiment, the AAV particles of the disclosure may be formulated in a solution comprising about 1.05% sodium chloride, about 0.212% sodium phosphate dibasic, heptahydrate, about 0.025% sodium phosphate monobasic, monohydrate, and 0.001% poloxamer 188, at a pH of about 7.4. As a non-limiting example, the concentration of AAV particle in this formulated solution may be about 0.001%. The concentration of sodium chloride in the final solution may be 0.1-2.0%, with non-limiting examples of 0.1%, 0.25%, 0.5%, 0.75%, 0.95%, 0.96%, 0.97%, 0.98%, 0.99%, 1.00%, 1.01%, 1.02%, 1.03%, 1.04%, 1.05%, 1.06%, 1.07%, 1.08%, 1.09%, 1.10%, 1.25%, 1.5%, 1.75%, or 2%. The concentration of sodium phosphate dibasic in the final solution may be 0.100-0.300% with non-limiting examples including 0.100%, 0.125%, 0.150%, 0.175%, 0.200%, 0.210, 0.211%, 0.212%, 0.213%, 0.214%, 0.215%, 0.225%, 0.250%, 0.275%, 0.300%. The concentration of sodium phosphate monobasic in the final solution may be 0.010-0.050%, with non-limiting examples of 0.010%, 0.015%, 0.020%, 0.021%, 0.022%, 0.023%, 0.024%, 0.025%, 0.026%, 0.027%, 0.028%, 0.029%, 0.030%, 0.035%, 0.040%, 0.045%, or 0.050%. The concentration of poloxamer 188 (pluronic acid (F-68)) may be 0.0001%-1%. As non-limiting examples, the concentration poloxamer 188 (pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In one embodiment, the formulation comprises components with the following CAS (Chemical Abstracts Services) Registry Numbers, 7647-14-15 (sodium chloride), 7782-85-6 (sodium phosphate dibasic, heptahydrate), 10049-21-5 (sodium phosphate monobasic, monohydrate), 9003-11-6 (poloxamer 188) and 2226647-27-2 (recombinant adeno-associated virus 2 vector VY-AADC02 human aromatic amino acid decarboxylase-specifying).

In some embodiments, the AAV formulations described herein may contain sufficient AAV particles for expression of at least one expressed functional payload. As a non-limiting example, the AAV particles may contain viral genomes encoding 1, 2, 3, 4 or 5 functional payloads.

According to the present disclosure AAV particles may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.*, 2009, 19, 137-140: the content of which is incorporated herein by reference in its entirety).

In some embodiments, formulations of the present disclosure may be packaged either in aqueous media or in lyophilized form. The container for the formulation will generally include at least one vial, test tube, flask, bottle, syringe or other container means, into which the formulation may be placed, and preferably, suitably aliquoted. Where there is more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present disclosure may also typically include means for containing compounds and/or compositions of the present disclosure, e.g., proteins, nucleic acids, and any other reagent containers in close confinement for commercial sale. Such containers may include injection or blow-molded plastic containers into which desired vials are retained.

Excipients and Diluents

The AAV particles of the disclosure can be formulated using one or more excipients or diluents to (1) increase stability; (2) increase cell transfection or transduction; (3) permit the sustained or delayed release of the payload; (4) alter the biodistribution (e.g., target the viral particle to specific tissues or cell types); (5) increase the translation of encoded protein; (6) alter the release profile of encoded protein and/or (7) allow for regulatable expression of the payload of the disclosure.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, M D, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In one embodiment, the AAV particles may be formulated in a hydrogel prior to administration. Hydrogels have a degree of flexibility which is similar to natural tissue as a result of their significant water content.

In another embodiment, a hydrogel may be administered to a subject prior to the administration of an AAV particle formulation. As a non-limiting example, the site of administration of the hydrogel may be within 3 inches (e.g., within 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less than 0.1 inches) of the site of administration of the AAV particle formulation.

Inactive Ingredients

In some embodiments, AAV particle formulations may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present disclosure may be approved by the US Food and Drug Administration (FDA).

In one embodiment, the AAV particle pharmaceutical compositions comprise at least one inactive ingredient such as, but not limited to, 1,2,6-Hexanetriol; 1,2-Dimyristoyl-Sn-Glycero-3-(Phospho-S-(1-Glycerol)); 1,2-Dimyristoyl-Sn-Glycero-3-Phosphocholine; 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-O-Tolylbiguanide; 2-Ethyl-1,6-Hexanediol; Acetic Acid; Acetic Acid, Glacial; Acetic Anhydride; Acetone; Acetone Sodium Bisulfite; Acetylated Lanolin Alcohols; Acetylated Monoglycerides; Acetylcysteine; Acetyltryptophan, DL-; Acrylates Copolymer; Acrylic Acid-Isooctyl Acrylate Copolymer; Acrylic Adhesive 788; Activated Charcoal; Adcote 72A103; Adhesive Tape; Adipic Acid; Aerotex Resin 3730; Alanine; Albumin Aggregated; Albumin Colloidal; Albumin Human: Alcohol; Alcohol, Dehydrated; Alcohol, Denatured; Alcohol, Diluted; Alfadex; Alginic Acid; Alkyl Ammonium Sulfonic Acid Betaine; Alkyl Aryl Sodium Sulfonate; Allantoin; Allyl .Alpha.-Ionone; Almond Oil; Alpha-Terpineol; Alpha-Tocopherol; Alpha-Tocopherol Acetate, Dl-; Alpha-Tocopherol, Dl-; Aluminum Acetate; Aluminum Chlorohydroxy Allantoinate; Aluminum Hydroxide; Aluminum Hydroxide—Sucrose, Hydrated; Aluminum Hydroxide Gel; Aluminum Hydroxide Gel F 500; Aluminum Hydroxide Gel F 5000; Aluminum Monostearate; Aluminum Oxide; Aluminum Polyester; Aluminum Silicate; Aluminum Starch Octenylsuccinate; Aluminum Stearate; Aluminum Subacetate; Aluminum Sulfate Anhydrous; Amerchol C: Amerchol-Cab; Aminomethylpropanol; Ammonia; Ammonia Solution; Ammonia Solution, Strong; Ammonium Acetate; Ammonium Hydroxide; Ammonium Lauryl Sulfate; Ammonium Nonoxynol-4 Sulfate; Ammonium Salt Of C-12-C-15 Linear Primary Alcohol Ethoxylate; Ammonium Sulfate; Ammonyx; Amphoteric-2;

Amphoteric-9; Anethole; Anhydrous Citric Acid; Anhydrous Dextrose; Anhydrous Lactose; Anhydrous Trisodium Citrate; Aniseed Oil: Anoxid Sbn; Antifoam; Antipyrine: Apaflurane; Apricot Kernel Oil Peg-6 Esters: Aquaphor: Arginine; Arlacel: Ascorbic Acid; Ascorbyl Palmitate; Aspartic Acid; Balsam Peru; Barium Sulfate: Beeswax; Beeswax, Synthetic; Beheneth-10; Bentonite; Benzalkonium Chloride; Benzenesulfonic Acid: Benzethonium Chloride; Benzododecinium Bromide; Benzoic Acid; Benzyl Alcohol; Benzyl Benzoate; Benzyl Chloride; Betadex; Bibapcitide; Bismuth Subgallate; Boric Acid; Brocrinat; Butane; Butyl Alcohol; Butyl Ester Of Vinyl Methyl Ether/ Maleic Anhydride Copolymer (125000 Mw); Butyl Stearate: Butylated Hydroxyanisole; Butylated Hydroxytoluene: Butylene Glycol; Butylparaben; Butyric Acid; C20-40 Pareth-24; Caffeine: Calcium; Calcium Carbonate; Calcium Chloride; Calcium Gluceptate; Calcium Hydroxide; Calcium Lactate; Calcobutrol; Caldiamide Sodium; Caloxetate Trisodium: Calteridol Calcium; Canada Balsam; Caprylic/ Capric Triglyceride; Caprylic/Capric/Stearic Triglyceride; Captan: Captisol; Caramel; Carbomer 1342; Carbomer 1382; Carbomer 934; Carbomer 934p: Carbomer 940: Carbomer 941: Carbomer 980; Carbomer 981; Carbomer Homopolymer Type B (Allyl Pentaerythritol Crosslinked); Carbomer Homopolymer Type C (Allyl Pentaerythritol Crosslinked); Carbon Dioxide; Carboxy Vinyl Copolymer; Carboxymethylcellulose; Carboxymethylcellulose Sodium; Carboxypolymethylene; Carrageenan; Carrageenan Salt; Castor Oil; Cedar Leaf Oil; Cellulose; Cellulose, Microcrystalline; Cerasynt-Se; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chlorobutanol; Chlorobutanol Hemihydrate; Chlorobutanol, Anhydrous: Chlorocresol; Chloroxylenol; Cholesterol: Choleth; Choleth-24: Citrate; Citric Acid; Citric Acid Monohydrate; Citric Acid, Hydrous; Cocamide Ether Sulfate; Cocamine Oxide: Coco Betaine; Coco Diethanolamide: Coco Monoethanolamide: Cocoa Butter; Coco-Glycerides; Coconut Oil; Coconut Oil, Hydrogenated: Coconut Oil/Palm Kernel Oil Glycerides, Hydrogenated; Cocoyl Caprylocaprate; Cola Nitida Seed Extract; Collagen; Coloring Suspension; Corn Oil; Cottonseed Oil: Cream Base; Creatine: Creatinine: Cresol; Croscarmellose Sodium: Crospovidone; Cupric Sulfate; Cupric Sulfate Anhydrous; Cyclomethicone; Cyclomethicone/Dimethicone Copolyol: Cysteine: Cysteine Hydrochloride; Cysteine Hydrochloride Anhydrous; Cysteine, Dl-; D&C Red No. 28; D&C Red No. 33: D&C Red No. 36: D&C Red No. 39: D&C Yellow No. 10; Dalfampridine: Daubert 1-5 Pestr (Matte) 164z; Decyl Methyl Sulfoxide; Dehydag Wax Sx; Dehydroacetic Acid; Dehymuls E; Denatonium Benzoate; Deoxycholic Acid; Dextran; Dextran 40; Dextrin; Dextrose; Dextrose Monohydrate; Dextrose Solution; Diatrizoic Acid; Diazolidinyl Urea; Dichlorobenzyl Alcohol; Dichlorodifluoromethane; Dichlorotetrafluoroethane; Diethanolamine; Diethyl Pyrocarbonate; Diethyl Sebacate; Diethylene Glycol Monoethyl Ether. Diethylhexyl Phthalate; Dihydroxyaluminum Aminoacetate; Diisopropanolamine; Diisopropyl Adipate; Diisopropyl Dilinoleate; Dimethicone 350; Dimethicone Copolyol; Dimethicone Mdx4-4210; Dimethicone Medical Fluid 360; Dimethyl Isosorbide; Dimethyl Sulfoxide; Dimethylaminoethyl Methacrylate Butyl Methacrylate—Methyl Methacrylate Copolymer; Dimethyldioctadecylammonium Bentonite: Dimethylsiloxane/Methylvinylsiloxane Copolymer: Dinoseb Ammonium Salt; Dipalmitoylphosphatidylglycerol, Dl-; Dipropylene Glycol; Disodium Cocoamphodiacetate; Disodium Laureth Sulfosuccinate; Disodium Lauryl Sulfosuccinate; Disodium Sulfosalicylate; Disofenin; Divinylbenzene Styrene Copolymer; Dmdm Hydantoin; Docosanol; Docusate Sodium: Duro-Tak 280-2516: Duro-Tak 387-2516: Duro-Tak 80-1196: Duro-Tak 87-2070; Duro-Tak 87-2194; Duro-Tak 87-2287; Duro-Tak 87-2296; Duro-Tak 87-2888; Duro-Tak 87-2979; Edetate Calcium Disodium; Edetate Disodium; Edetate Disodium Anhydrous; Edetate Sodium; Edetic Acid: Egg Phospholipids; Entsufon; Entsufon Sodium; Epilactose; Epitetracycline Hydrochloride: Essence Bouquet 9200: Ethanolamine Hydrochloride; Ethyl Acetate; Ethyl Oleate: Ethylcelluloses; Ethylene Glycol; Ethylene Vinyl Acetate Copolymer; Ethylenediamine; Ethylenediamine Dihydrochloride; Ethylene-Propylene Copolymer; Ethylene-Vinyl Acetate Copolymer (28% Vinyl Acetate); Ethylene-Vinyl Acetate Copolymer (9% Vinylacetate); Ethylhexyl Hydroxystearate; Ethylparaben; Eucalyptol; Exametazime; Fat, Edible; Fat, Hard; Fatty Acid Esters; Fatty Acid Pentaerythritol Ester; Fatty Acids; Fatty Alcohol Citrate; Fatty Alcohols; Fd&C Blue No. 1; Fd&C Green No. 3; Fd&C Red No. 4; Fd&C Red No. 40; Fd&C Yellow No. 10 (Delisted); Fd&C Yellow No. 5; Fd&C Yellow No. 6: Ferric Chloride; Ferric Oxide; Flavor 89-186; Flavor 89-259; Flavor Df-119: Flavor Df-1530; Flavor Enhancer; Flavor Fig. 827118; Flavor Raspberry Pfc-8407; Flavor Rhodia Pharmaceutical No. Rf 451; Fluorochlorohydrocarbons; Formaldehyde; Formaldehyde Solution; Fractionated Coconut Oil; Fragrance 3949-5; Fragrance 520a; Fragrance 6.007; Fragrance 91-122; Fragrance 9128-Y; Fragrance 93498 g; Fragrance Balsam Pine No. 5124; Fragrance Bouquet 10328; Fragrance Chemoderm 6401-B; Fragrance Chemoderm 6411; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O Fl-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Gadolinium Oxide; Galactose; Gamma Cyclodextrin; Gelatin; Gelatin, Crosslinked; Gelfoam Sponge; Gellan Gum (Low Acyl); Gelva 737; Gentisic Acid; Gentisic Acid Ethanolamide; Gluceptate Sodium; Gluceptate Sodium Dihydrate; Gluconolactone; Glucuronic Acid; Glutamic Acid, Dl-; Glutathione; Glycerin; Glycerol Ester Of Hydrogenated Rosin; Glyceryl Citrate; Glyceryl Isostearate; Glyceryl Laurate: Glyceryl Monostearate: Glyceryl Oleate; Glyceryl Oleate/Propylene Glycol; Glyceryl Palmitate; Glyceryl Ricinoleate: Glyceryl Stearate; Glyceryl Stearate—Laureth-23; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; Glycine: Glycine Hydrochloride; Glycol Distearate; Glycol Stearate: Guanidine Hydrochloride; Guar Gum: Hair Conditioner (18n195-1m); Heptane; Hetastarch: Hexylene Glycol; High Density Polyethylene: Histidine: Human Albumin Microspheres; Hyaluronate Sodium: Hydrocarbon; Hydrocarbon Gel, Plasticized: Hydrochloric Acid; Hydrochloric Acid, Diluted; Hydrocortisone; Hydrogel Polymer; Hydrogen Peroxide; Hydrogenated Castor Oil; Hydrogenated Palm Oil; Hydrogenated Palm/Palm Kernel Oil Peg-6 Esters; Hydrogenated Polybutene 635-690; Hydroxide Ion; Hydroxyethyl Cellulose; Hydroxyethylpiperazine Ethane Sulfonic Acid; Hydroxymethyl Cellulose; Hydroxyoctacosanyl Hydroxystearate; Hydroxypropyl Cellulose: Hydroxypropyl Methylcellulose 2906; Hydroxypropyl- Beta-cyclodextrin; Hypromellose 2208 (15000 Mpa·S): Hypromellose 2910 (15000 Mpa·S); Hypromelloses; Imidurea; Iodine: Iodoxamic Acid: Iofetamine Hydrochloride; Irish Moss Extract; Isobutane; Isoceteth-20; Isoleucine: Isooctyl Acrylate; Isopropyl Alcohol; Isopropyl Isostearate; Isopropyl Myristate; Isopropyl Myristate—Myristyl Alcohol; Isopropyl Palmitate; Isopropyl Stearate; Isostearic Acid; Isostearyl Alcohol; Isotonic Sodium Chloride Solution; Jelene; Kaolin; Kathon Cg; Kathon Cg II; Lactate; Lactic Acid; Lactic Acid, Dl-; Lactic Acid, L-; Lactobionic Acid; Lactose; Lactose Monohydrate; Lactose, Hydrous; Laneth; Lanolin; Lanolin Alcohol—Mineral Oil; Lanolin Alcohols; Lanolin Anhydrous; Lanolin Cholesterols; Lanolin Nonionic Derivatives; Lanolin. Ethoxylated; Lanolin, Hydrogenated; Lauralkonium Chloride: Lauramine Oxide; Laurdimonium Hydrolyzed Animal Collagen; Laureth Sulfate; Laureth-2: Laureth-23; Laureth-4: Lauric Diethanolamide: Lauric Myristic Diethanolamide; Lauroyl Sarcosine; Lauryl Lactate: Lauryl Sulfate; *Lavandula angustifolia* Flowering Top; Lecithin; Lecithin Unbleached; Lecithin, Egg, Lecithin, Hydrogenated; Lecithin, Hydrogenated Soy; Lecithin, Soybean; Lemon Oil; Leucine; Levulinic Acid: Lidofenin; Light Mineral Oil; Light Mineral Oil (85 Ssu); Limonene, (+/−)-; Lipocol Sc-15; Lysine; Lysine Acetate; Lysine Monohydrate; Magnesium Aluminum Silicate; Magnesium Aluminum Silicate Hydrate; Magnesium Chloride; Magnesium Nitrate; Magnesium Stearate; Maleic Acid; Mannitol; Maprofix; Mebrofenin; Medical Adhesive Modified S-15; Medical Antiform A-F Emulsion: Medronate Disodium; Medronic Acid; Meglumine; Menthol: Metacresol; Metaphosphoric Acid; Methanesulfonic Acid; Methionine; Methyl Alcohol: Methyl Gluceth-10; Methyl Gluceth-20; Methyl Gluceth-20 Sesquistearate: Methyl Glucose Sesquistearate: Methyl Laurate: Methyl Pyrrolidone: Methyl Salicylate; Methyl Stearate; Methylboronic Acid; Methylcellulose (4000 Mpa·S); Methylcelluloses; Methylchloroisothiazolinone; Methylene Blue; Methylisothiazolinone; Methylparaben; Microcrystalline Wax; Mineral Oil. Mono And Diglyceride; Monostearyl Citrate: Monothioglycerol; Multisterol Extract; Myristyl Alcohol; Myristyl Lactate: Myristyl-.Gamma.-Picolinium Chloride: N-(Carbamoyl-Methoxy Peg-40)-1,2-Distearoyl-Cephalin Sodium; N,N-Dimethylacetamide; Niacinamide; Nioxime; Nitric Acid; Nitrogen: Nonoxynol Iodine: Nonoxynol-15; Nonoxynol-9; Norflurane; Oatmeal; Octadecene-1/Maleic Acid Copolymer; Octanoic Acid: Octisalate; Octoxynol-1; Octoxynol-40; Octoxynol-9; Octyldodecanol; Octylphenol Polymethylene; Oleic Acid; Oleth-10/Oleth-5; Oleth-2; Oleth-20; Oleyl Alcohol; Oleyl Oleate; Olive Oil; Oxidronate Disodium: Oxyquinoline; Palm Kemel Oil; Palmitamine Oxide; Parabens; Paraffin; Paraffin, White Soft; Parfum Creme 45/3; Peanut Oil; Peanut Oil, Refined; Pectin; Peg 6-32 Stearate/Glycol Stearate; Peg Vegetable Oil; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Sorbitan Isostearate; Peg-22 Methyl Ether/Dodecyl Glycol Copolymer; Peg-25 Propylene Glycol Stearate; Peg-4 Dilaurate; Peg-4 Laurate; Peg-40 Castor Oil; Peg-40 Sorbitan Diisostearate; Peg-45/Dodecyl Glycol Copolymer; Peg-5 Oleate; Peg-50 Stearate; Peg-54 Hydrogenated Castor Oil; Peg-6 Isostearate; Peg-60 Castor Oil; Peg-60 Hydrogenated Castor Oil; Peg-7 Methyl Ether; Peg-75 Lanolin; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume Bouquet; Perfume E-1991; Perfume Gd 5604; Perfume Tana 90/42 Scba; Perfume W-1952-1; Petrolatum; Petrolatum, White; Petroleum Distillates; Phenol; Phenol, Liquefied; Phenonip; Phenoxyethanol; Phenylalanine; Phenylethyl Alcohol; Phenylmercuric Acetate; Phenylmercuric Nitrate; Phosphatidyl Glycerol. Egg; Phospholipid; Phospholipid, Egg; Phospholipon 90 g; Phosphoric Acid; Pine Needle Oil (*Pinus Sylvestris*); Piperazine Hexahydrate: Plastibase-50 w; Polacrilin; Polidronium Chloride; Poloxamer 124; Poloxamer 181; Poloxamer 182; Poloxamer 188; Poloxamer 237; Poloxamer 407; Poly(Bis(P-Carboxyphenoxy)Propane Anhydride):Sebacic Acid; Poly(Dimethylsiloxane/Methylvinylsiloxane/Methylhydrogensiloxane) Dimethylvinyl Or Dimethylhydroxy Or Trimethyl Endblocked; Poly(Dl-Lactic-Co-Glycolic Acid). (50:50; Poly (Dl-Lactic-Co-Glycolic Acid), Ethyl Ester Terminated, (50: 50; Polyacrylic Acid (250000 Mw); Polybutene (1400 Mw); Polycarbophil; Polyester; Polyester Polyamine Copolymer; Polyester Rayon; Polyethylene Glycol 1000; Polyethylene Glycol 1450; Polyethylene Glycol 1500; Polyethylene Glycol 1540; Polyethylene Glycol 200; Polyethylene Glycol 300; Polyethylene Glycol 300-1600; Polyethylene Glycol 3350; Polyethylene Glycol 400; Polyethylene Glycol 4000; Polyethylene Glycol 540; Polyethylene Glycol 600; Polyethylene Glycol 6000; Polyethylene Glycol 8000; Polyethylene Glycol 900; Polyethylene High Density Containing Ferric Oxide Black (<1%); Polyethylene Low Density Containing Barium Sulfate (20-24%); Polyethylene T; Polyethylene Terephthalates; Polyglactin; Polyglyceryl-3 Oleate; Polyglyceryl-4 Oleate; Polyhydroxyethyl Methacrylate; Polyisobutylene; Polyisobutylene (1100000 Mw); Polyisobutylene (35000 Mw); Polyisobutylene 178-236; Polyisobutylene 241-294; Polyisobutylene 35-39; Polyisobutylene Low Molecular Weight; Polyisobutylene Medium Molecular Weight; Polyisobutylene/Polybutene Adhesive; Polylactide; Polyols; Polyoxyethylene Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 35 Castor Oil; Polyoxyl 40 Hydrogenated Castor Oil; Polyoxyl 40 Stearate; Polyoxyl 400 Stearate; Polyoxyl 6 And Polyoxyl 32 Palmitostearate: Polyoxyl Distearate; Polyoxyl Glyceryl Stearate; Polyoxyl Lanolin; Polyoxyl Palmitate; Polyoxyl Stearate; Polypropylene: Polypropylene Glycol; Polyquaternium-10; Polyquaternium-7 (70/30 Acrylamide/Dadmac; Polysiloxane; Polysorbate 20; Polysorbate 40; Polysorbate 60; Polysorbate 65; Polysorbate 80; Polyurethane; Polyvinyl Acetate; Polyvinyl Alcohol; Polyvinyl Chloride; Polyvinyl Chloride-Polyvinyl Acetate Copolymer; Polyvinylpyridine; Poppy Seed Oil; Potash; Potassium Acetate; Potassium Alum, Potassium Bicarbonate; Potassium Bisulfite; Potassium Chloride; Potassium Citrate; Potassium Hydroxide; Potassium Metabisulfite; Potassium Phosphate, Dibasic; Potassium Phosphate, Monobasic; Potassium Soap; Potassium Sorbate; Povidone Acrylate Copolymer; Povidone Hydrogel; Povidone K17; Povidone K25; Povidone K29/32; Povidone K30; Povidone K90; Povidone K90f; Povidone/Eicosene Copolymer; Povidones; Ppg-12/Smdi Copolymer; Ppg-15 Stearyl Ether; Ppg-20 Methyl Glucose Ether Distearate; Ppg-26 Oleate; Product Wat; Proline; Promulgen D; Promulgen G; Propane; Propellant A-46; Propyl Gallate; Propylene Carbonate; Propylene Glycol; Propylene Glycol Diacetate; Propylene Glycol Dicaprylate: Propylene Glycol Monolaurate. Propylene Glycol Monopalmitostearate; Propylene Glycol Palmitostearate; Propylene Glycol Ricinoleate; Propylene Glycol/Diazolidinyl Urea/Methylparaben/Propylparben: Propylparaben; Protamine Sulfate; Protein Hydrolysate; Pvm/Ma Copolymer; Quaternium-15; Quaternium-15 Cis- Form; Quaternium-52; Ra-2397; Ra-3011; Saccharin; Saccharin Sodium; Saccharin Sodium Anhydrous; Safflower Oil; Sd Alcohol 3a; Sd Alcohol 40; Sd Alcohol 40-2; Sd Alcohol 40b; Sepineo P 600; Serine; Sesame Oil; Shea Butter; Silastic Brand Medical Grade Tubing; Silastic Medical Adhesive, Silicone Type A; Silica, Dental: Silicon; Silicon Dioxide; Silicon Dioxide, Colloidal; Silicone; Silicone Adhesive 4102; Silicone Adhesive 4502; Silicone Adhesive Bio-Psa Q7-4201; Silicone Adhesive Bio-Psa Q7-4301; Silicone Emulsion; Silicone/Polyester Film Strip: Simethicone; Simethicone Emulsion; Sipon Ls 20np; Soda Ash; Sodium Acetate; Sodium Acetate Anhydrous; Sodium Alkyl Sulfate; Sodium Ascorbate; Sodium Benzoate; Sodium Bicarbonate: Sodium Bisulfate; Sodium Bisulfite; Sodium Borate; Sodium Borate Decahydrate: Sodium Carbonate; Sodium Carbonate Decahydrate; Sodium Carbonate Monohydrate; Sodium Cetostearyl Sulfate; Sodium Chlorate; Sodium Chloride: Sodium Chloride Injection; Sodium Chloride Injection, Bacteriostatic; Sodium Cholesteryl Sulfate; Sodium Citrate; Sodium Cocoyl Sarcosinate; Sodium Desoxycholate; Sodium Dithionite; Sodium Dodecylbenzenesulfonate: Sodium Formaldehyde Sulfoxylate; Sodium Gluconate: Sodium Hydroxide; Sodium Hypochlorite: Sodium Iodide; Sodium Lactate; Sodium Lactate, L-; Sodium Laureth-2 Sulfate: Sodium Laureth-3 Sulfate: Sodium Laureth-5 Sulfate; Sodium Lauroyl Sarcosinate: Sodium Lauryl Sulfate; Sodium Lauryl Sulfoacetate; Sodium Metabisulfite; Sodium Nitrate; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Dodecahydrate; Sodium Phosphate, Dibasic, Heptahydrate: Sodium Phosphate, Monobasic: Sodium Phosphate, Monobasic, Anhydrous; Sodium Phosphate. Monobasic, Dihydrate: Sodium Phosphate, Monobasic, Monohydrate; Sodium Polyacrylate (2500000 Mw); Sodium Pyrophosphate; Sodium Pyrrolidone Carboxylate; Sodium Starch Glycolate; Sodium Succinate Hexahydrate; Sodium Sulfate; Sodium Sulfate Anhydrous; Sodium Sulfate Decahydrate: Sodium Sulfite; Sodium Sulfosuccinated Undecylenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Xylenesulfonate; Somay 44; Sorbic Acid; Sorbitan: Sorbitan Isostearate; Sorbitan Monolaurate; Sorbitan Monooleate; Sorbitan Monopalmitate: Sorbitan Monostearate: Sorbitan Sesquioleate; Sorbitan Trioleate; Sorbitan Tristearate; Sorbitol; Sorbitol Solution; Soybean Flour; Soybean Oil; Spearmint Oil; Spermaceti; Squalane; Stabilized Oxychloro Complex; Stannous 2-Ethylhexanoate; Stannous Chloride; Stannous Chloride Anhydrous; Stannous Fluoride; Stannous Tartrate; Starch: Starch 1500, Pregelatinized: Starch, Corn; Stearalkonium Chloride; Stearalkonium Hectorite/Propylene Carbonate; Stearamidoethyl Diethylamine; Steareth-10; Steareth-100; Steareth-2; Steareth-20; Steareth-21; Steareth-40; Stearic Acid; Stearic Diethanolamide; Stearoxytrimethylsilane; Steartrimonium Hydrolyzed Animal Collagen; Stearyl Alcohol; Sterile Water For Inhalation; Styrene/Isoprene/Styrene Block Copolymer; Succimer; Succinic Acid: Sucralose; Sucrose; Sucrose Distearate: Sucrose Polyesters: Sulfacetamide Sodium; Sulfobutylether .Beta.-Cyclodextrin; Sulfur Dioxide; Sulfuric Acid; Sulfurous Acid; Surfactol Qs: Tagatose, D-; Talc: Tall Oil: Tallow Glycerides: Tartaric Acid: Tartaric Acid, Dl-; Tenox: Tenox-2; Tert-Butyl Alcohol; Tert-Butyl Hydroperoxide; Tert-Butylhydroquinone; Tetrakis(2-Methoxyisobutylisocyanide)Copper(I) Tetrafluoroborate; Tetrapropyl Orthosilicate; Tetrofosmin; Theophylline: Thimerosal; Threonine; Thymol; Tin; Titanium Dioxide; Tocopherol: Tocophersolan: Total parenteral nutrition, lipid emulsion; Triacetin; Tricaprylin; Trichloromonofluormethane; Trideceth-10; Triethanolamine Lauryl Sulfate; Trifluoroacetic Acid; Triglycerides, Medium Chain; Trihydroxystearin; Trilaneth-4 Phosphate; Trilaureth-4 Phosphate; Trisodium Citrate Dihydrate; Trisodium Hedta Triton 720; Triton X-200: Trolamine; Tromantadine; Tromethamine (TRIS); Tryptophan; Tylaxapol: Tyrosine: Undecylenic Acid; Union 76 Amsco-Res 6038; Urea; Valine: Vegetable Oil: Vegetable Oil Glyceride, Hydrogenated; Vegetable Oil, Hydrogenated; Versetamide; Viscarin, Viscose/Cotton; Vitamin E; Wax, Emulsifying: Wecobec Fs: White Ceresin Wax: White Wax; Xanthan Gum; Zinc; Zinc Acetate; Zinc Carbonate; Zinc Chloride; and Zinc Oxide.

Pharmaceutical composition formulations of AAV particles disclosed herein may include cations or anions. In one embodiment, the formulations include metal cations such as, but not limited to, Zn2+, Ca2+, Cu2+, Mn2+, Mg+ and combinations thereof. As a non-limiting example, formulations may include polymers and complexes with a metal cation (See e.g., U.S. Pat. Nos. 6,265,389 and 6,555,525, each of which is herein incorporated by reference in its entirety).

Formulations of the disclosure may also include one or more pharmaceutically acceptable salts. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use. P. H. Stahl and C. G. Wermuth (eds.), Wiley-VCH, 2008, and Berge et al., Journal of Pharmaceutical Science, 66, 1-19 (1977); the content of each of which is incorporated herein by reference in their entirety.

The term "pharmaceutically acceptable solvate," as used herein, means a compound of the disclosure wherein molecules of a suitable solvent are incorporated in the crystal lattice. A suitable solvent is physiologically tolerable at the dosage administered. Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

IV. Definitions

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein: (4) folding of a polypeptide or protein; and (5) post-translational modification of a polypeptide or protein.

As used herein, a "viral particle" is a virus comprised of at least two components, a protein capsid and a polynucleotide sequence enclosed within the capsid.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

As used herein, a "formulation" includes at least one polynucleotide and/or compound and/or composition of the present disclosure (e.g., a vector, AAV particle, etc.) and a delivery agent.

A "fragment," as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody subjected to enzymatic digestion or synthesized as such.

As used herein, "payload" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid.

As used herein. "payload construct" is one or more polynucleotide regions encoding or comprising a payload that is flanked on one or both sides by an inverted terminal repeat (ITR) sequence. The payload construct is a template that is replicated in a viral production cell to produce a viral genome.

As used herein, "payload construct vector" is a vector encoding or comprising a payload construct, and regulatory regions for replication and expression in bacterial cells.

As used herein, a "payload construct expression vector" is a vector encoding or comprising a payload construct and which further comprises one or more polynucleotide regions encoding or comprising components for viral expression in a viral replication cell.

As used herein, "peptide" is less than or equal to 50 amino acids long, e.g., about 5, 10, 15, 20, 25, 30, 35, 40, 45, or 50 amino acids long.

As used herein, a "viral genome" is a polynucleotide encoding at least one inverted terminal repeat (ITR), at least one regulatory sequence, and at least one payload. The viral genome is derived by replication of a payload construct from the payload construct expression vector. A viral genome encodes at least one copy of the payload construct.

As used herein, the term "transfection" refers to methods to introduce exogenous nucleic acids into a cell. Methods of transfection include, but are not limited to, chemical methods, physical treatments and cationic lipids or mixtures.

As used herein, the term "assay" refers to the sequence of activities associated with a reported result, which can include, but is not limited to: cell seeding, preparation of the test material, infection, lysis, analysis, and calculation of results.

As used herein, the term "molecule of interest" refers to a protein provided herein and fragments, mutants, variants, and alterations thereof.

As used herein, the term "AADC reaction" refers to the reaction of L-DOPA with AADC to form dopamine.

As used herein, the term "potency" refers to a measure of biological activity, for example a measure of the biological activity of a protein, such as an enzyme, e.g., AADC. In certain embodiments, the biological activity of AADC can be measured as an absolute amount by measuring the conversion of L-DOPA to dopamine over a period of time. In certain embodiments, potency can be assessed by comparing the biological activity of a protein to that of a reference standard. Potency can be assessed by measuring the biological activity of a protein produced by a viral vector, e.g., an AAV vector. Potency can be assessed by comparing the biological activity of a protein produced by a viral vector, e.g., an AAV vector, to the biological activity of a protein produced by a reference viral vector, e.g., a reference AAV vector. For example, potency can be assessed by comparing the biological activity of AADC to that of a reference AADC standard. Potency can be assessed by measuring the biological activity of AADC produced by a viral vector, e.g., an AAV vector. Potency can be assessed by comparing the biological activity of AADC produced by a viral vector, e.g., an AAV vector, to the biological activity of AADC produced by a reference AADC viral vector, e.g., a reference AADC AAV vector.

As used herein, the term "vector" refers to any molecule or moiety which transports, transduces or otherwise acts as a carrier of a heterologous molecule such as polynucleotides. A "viral vector" is a vector which comprises one or more polynucleotide regions encoding or comprising a molecule of interest. In the context of the present disclosure, the viral vectors and vector particles can be produced recombinantly and can be based on adeno-associated virus (AAV) parent or reference sequences. AAVs have emerged as one of the most widely studied and utilized viral vectors for gene transfer to mammalian cells and methods for the production of a viral vector are well known in the art. See, e.g., Tratschin et al., *Mol. Cell Biol.*, 1985, 5(11):3251-3260; Grimm et al., Hum. Gene Ther., 1999, 10(15):2445-2450; Chiorini et al., *J. Vir,* 1997, 71: 6823-33; Srivastava et al., *J. Vir.* 1983, 45:555-564; Chiorini et al., *J. Vir.* 1999, 73: 1309-1319; Rutledge et al., *J. Vir.* 1998, 72:309-319; and Wu et al., *J. Vir.* 2000, 74: 8635-47, the contents of each of which are herein incorporated by reference in their entirety.

As used herein, the term "multiplicity of infection" or "MOI" is the ratio of agents, such as phage or more generally virus, to infection targets, such as cells, i.e., the average number of virus particles infecting each cell. For example, when referring to a group of cells inoculated with virus particles, the multiplicity of infection or MOI is the ratio of the number of virus particles to the number of target cells present in a defined space. As used herein, a "particle" in the context of a virus, e.g., a parvovirus, is a virus that includes at least two components, a protein capsid component and a polynucleotide sequence, e.g., genome enclosed within the capsid component.

The terms "cell" or "cell line" used herein mean any cell that allows for replication of a virus, e.g., a parvovirus or dependoparvovirus, for example, an adenovirus or AAV, e.g., AAV2, and which can be maintained in culture and infected with a viral vector in accordance with the present disclosure and standard techniques. In certain embodiments, the cells are mammalian cells, for example, human cells. In specific embodiment, the cells are sarcoma cells, for example, fibrosarcoma cells. Primary cells or primary cell cultures can be utilized, as can cell lines. Non-limiting examples of cell lines include HT1080 (for example, ATCC® CCL-121™) human fibrosarcoma cell lines. CHO, HeLa, Vero, HEK293, or HEK293K cell lines, or variants of such cell lines.

As used herein, "cell lysis" refers to the breaking of the cell wall to release the intracellular contents. Cell lysis methods can be selected based on the cell culture format of cells to be lysed. In some embodiments, chemical lysis can be used to lyse cells.

As used herein, the term "lysis agent" refers to any agent that can aid in the disruption of a cell. In some cases, lysis agents are introduced in solutions, termed lysis solutions or lysis buffers.

As used herein, the term "lysis solution" refers to a solution (typically aqueous) including one or more lysis agents. In addition to lysis agents, lysis solutions can include one or more buffering agents, solubilizing agents, surfactants, preservatives, cryoprotectants, enzymes, enzyme inhibitors and/or chelators. Lysis buffers are lysis solutions including one or more buffering agents. Additional components of lysis solutions can include one or more solubilizing agents.

As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity. In some cases, lysis agents can be selected from lysis salts, amphoteric agents, cationic agents, ionic detergents and non-ionic detergents. Lysis salts can include, but are not limited to sodium chloride (NaCl) and potassium chloride (KCl).

In some embodiments, mechanical cell lysis is carried out. Mechanical cell lysis methods can include the use of one or more lysis conditions and/or one or more lysis forces. As used herein, the term lysis condition refers to a state or circumstance that promotes cellular disruption, for example, certain temperatures, pressures, osmotic purity, salinity and the like. Cell lysis carried out according to such embodiments can include freeze-thaw lysis. As used herein, the term freeze-thaw lysis refers to cellular lysis in which a cell solution is subjected to one or more freeze-thaw cycles. According to freeze-thaw lysis methods, cells in solution are frozen to induce a mechanical disruption of cellular membranes caused by the formation and expansion of ice crystals. Cell solutions used according to freeze-thaw lysis methods, can further include one or more lysis agents, solubilizing agents, buffering agents, cryoprotectants, surfactants, preservatives, enzymes, enzyme inhibitors and/or chelators. In some embodiments, freeze-thaw lysis can be carried out according to any of the methods described in U.S. Pat. No. 7,704,721, the contents of which are herein incorporated by reference in their entirety. In some embodiments, mechanical cell lysis can include a physical activity used to disrupt a cell ("lysis force"). Lysis forces can include, but are not limited to mechanical forces, sonic forces, gravitational forces, optical forces, electrical forces and the like. Mechanical forces that can be used according to lysis force can include high shear fluid forces and/or physical disruption of cells by scraping.

Non-limiting examples of chemical lysis include the use of detergent solutions or salt solutions. Non-limiting examples of physical/mechanical lysis of cells include sonication, freeze/thawing, blending, or grinding.

The term "parvovirus" as used herein refers to DNA animal viruses that contain a linear, single-stranded DNA genome and encompasses the family Parvoviridae, including autonomously-replicating parvoviruses and dependoparvovirus. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline, panleukopenia virus, feline parvovirus, goose parvovirus, and B19 virus. Other autonomous parvoviruses are known to those skilled in the art.

As used herein, the term "aromatic L-amino acid decarboxylase" or "AADC," refers to an enzyme involved in the decarboxylation of L-DOPA to generate dopamine.

As used herein, the term "HT-1080 cells" refers to a human immortalized cell line originating from a fibrosarcoma; this cell line is sourced from ATCC® (CCL-121). These cells are permissive to AAV2 and express the AADC enzyme when transduced with the AAV2.AADC vector described herein.

As used herein, the term "UHPLC-ECD" refers to ultra high-performance liquid chromatography with an electrochemical detector.

As used herein, the term "UHPLC-UV" refers to ultra high-performance liquid chromatography with an ultraviolet detector.

As used herein, the term "sample" refers to a single test article for analysis.

V. EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

EXAMPLES

Example 1. Qualification of UHPLC-UV

The method for the quantitation of dopamine in AAV2.AADC-transduced HT1080 cells lysates by reverse phase UHPLC with UV detection at 280 nm is described in this Example. All assessed parameters (e.g., specificity, precision, accuracy, and linearity) were found to be within the expected limits.

Peak areas for dopamine standards and dopamine produced by AAV2.AADC-transduced HT1080 cells were integrated and used to calculate calibration curves and to asses qualification parameters. HT-1080 cells were cultured in flasks and seeded in platses with DMEMc media (10% FBS in DMEM+GLUTAMAX). AAV2.AADC was also diluted in DMEMc media to transduce HT-1080 cells. After transduction incubation, cells were lysed with Lysis Buffer (1×PBS+Triton X-100). The cell lysate is then reacted with L-DOPA in the Reaction Buffer taught in Example 3, resulting in the decarboxylation of L-dopa to Dopamine by the AADC enzyme.

Stage 1

The calibration curves used for quantitation, spanning three logs of concentration from 320 to 0.3 µM, were prepared according to two different protocols. One protocol covered the whole range by simple two-fold dilutions, and another protocol provided an evenly spaced concentration range to avoid systemic bias of the calibration curve. A second low concentration range was added to the latter protocol to better identify limit of detection (LOD) and quantitation (LOQ).

Samples were injected according to the following schedule: Calibration Standard Set 1, Transfected Lysates in triplicates, Calibration Standard Set 2, Spiked Transfected Lysates in triplicates, Calibration Standard Set 3; totaling 64 injections. A column cleaning protocol with 50% acetonitrile was performed in between each Standard Set and Transfected Lysate set. The 64 injections were repeated five consecutive times. Results are shown for the first execution of the 64 injections, and data for the other four were observed to be equivalent.

Chromatograms were observed to show an overlay of the whole range of the dopamine calibration standards. A fitted linear regression model showed a $R^2$ of 0.999. These results show an acceptable level of linearity for the data.

The criteria for specificity was that 1) spiked cell lysates must produce a single peak; 2) difference between elution times of spiked and non-spiked cell lysates, and dopamine standard alone, must be ±0.1 min; and 3) no interfering peaks coming from the blank controls. In the present Example, the peak in the transfected cell lysates was observed to co-elute with the peak observed for the dopamine standard. Chromatograms showed an overlay of the 20 µM dopamine standards and cell lysates transduced at MOI 1563 spiked with dopamine corresponding to 16 µM. A single peak was observed in the spiked transduced lysates, co-eluting with the dopamine standard. The lowest dopamine concentration (0.3 µM) was overlaid on mock-transduced whole cell lysates, and no interfering peaks were observed in the mock-transduced lysates.

Table 2 exemplifies the calculations performed on the triplicates of a single set of 64 injections. The shifts in elution times, reported in the bottom three rows, calculated when comparing the average times for standards, transduced lysates, and spiked transduced lysates, are +0.1 minutes. All criteria specified in the protocol for specificity were satisfied.

Acceptance criteria were set for Accuracy as a recovery of ±20%, with recovery standard deviation (RSD) less than or equal to 10% between replicates. All the samples in Table 2 met these criteria.

Precision was defined as integrated peak areas for triplicates with a RSD of less than or equal to 10%. Table 2 shows that to be true for all transduced and spiked cell lysate samples, as well as for calibration standards with the exceptions of the. The criteria were met, except for the highest (300 µM) and lowest (0.3 µM) dopamine concentrations.

Repeatability was evaluated by repeating the set of 64 injections five times, and then by comparing the results across the repeats. The same calculations were averaged across the 5 consecutive repeats. Statistics showed that the conclusion derived for the first run held true through the complete set of five measurements.

Limit of detection (LOD) was defined as 3.3 σ/Slope, and limit of quantification (LOQ) was defined as 10 σ/Slope. "σ" is the standard deviation of the response at the 5 lowest dilutions, calculated as the standard deviation of the y-intercepts of the calibration lines, and "slope" is the slope of the calibration curve. The average LOQ was 0.233 µM, and the average LOD was 0.070 µM.

Stage 2

In Stage 2, samples were injected according to the following schedule: Calibration Standard Set 1, Transfected Lysates in triplicates, Calibration Standard Set 2, Spiked Transfected Lysates in triplicates, and Calibration Standard Set 3 totaling 72 injections. A column cleaning protocol with 50% acetonitrile was performed in between each Standard Set and Transfected Lysate set. The 72 injections were repeated five consecutive times.

The calibration curve with evenly-spaced dilutions in the range from 320 to 32 µM and the low concentration range from 2.88 to 0.32 µM is shown in Table 3. The low range, from 0.32 to 2.88 was used to calculate LOD and LOQ. The $R^2$ was 0.9996 in the low range.

TABLE 2

Specificity

| | Peak area | | | Elution Time | | | Concentration | | | Accuracy |
|---|---|---|---|---|---|---|---|---|---|---|
| | Average | SD | % CV | Average | SD | % CV | Average | SD | % CV | % recovery |
| S1 | 7.26 | | 10.42 | 2.00 | 0.00 | 0.08 | | | | |
| S2 | 3.41 | 0.24 | 7.01 | 2.01 | 0.00 | 0.03 | | | | |
| S3 | 1.67 | 0.11 | 6.38 | 2.01 | 0.00 | 0.03 | | | | |
| S4 | 0.82 | 0.03 | 3.57 | 2.01 | 0.00 | 0.00 | | | | |
| S5 | 0.42 | 0.02 | 5.73 | 2.01 | 0.00 | 0.03 | | | | |
| S6 | 0.21 | 0.01 | 6.61 | 2.01 | 0.00 | 0.03 | | | | |
| S7 | 0.11 | 0.01 | 8.31 | 2.01 | 0.00 | 0.05 | | | | |
| S8 | 0.05 | 0.00 | 7.81 | 2.01 | 0.00 | 0.03 | | | | |
| S9 | 0.03 | 0.00 | 6.42 | 2.01 | 0.00 | 0.08 | | | | |
| S10 | 0.01 | 0.00 | 7.87 | 2.01 | 0.00 | 0.15 | | | | |
| S11 | 0.01 | 0.00 | 28.57 | 2.01 | 0.00 | 0.10 | | | | |
| MOI 100000 | 4.30 | 0.03 | 0.79 | 2.01 | 0.00 | 0.06 | 192.85 | 1.51 | 0.79 | |
| MOI 1563 | 1.47 | 0.02 | 1.28 | 2.01 | 0.00 | 0.03 | 66.92 | 0.82 | 1.23 | |
| MOI 24 | 0.02 | 0.00 | 0.00 | 2.01 | 0.00 | 0.13 | 2.53 | 0.01 | 0.44 | |
| MOI 0 | NA | NA | NA | NA | NA | NA | NA | NA | NA | NA |
| MOI 100000 Spiked* | 4.49 | 0.02 | 0.53 | 2.01 | 0.00 | 0.09 | 201.32 | 1.08 | 0.53 | 96.39 |
| MOI 1563 Spiked* | 1.79 | 0.01 | 0.66 | 2.01 | 0.00 | 0.03 | 81.01 | 0.52 | 0.64 | 97.70 |
| MOI 24 Spiked * | 0.38 | 0.02 | 5.85 | 2.01 | 0.00 | 0.00 | 18.34 | 0.98 | 5.36 | 98.97 |
| MOI 0 Spiked* | 0.35 | 0.01 | 3.44 | 2.01 | 0.00 | 0.00 | 16.94 | 0.52 | 3.09 | 105.9 |
| Standards vs MOI shift (min) | | | | 0.001 | | | | | | |
| Standard vs MOI spiked shift (min) | | | | 0.002 | | | | | | |
| MOI vs MOI spiked shift (min) | | | | 0.000 | | | | | | |

TABLE 3

Values from the calibration curve

| Dopamine concentration [µM] | Integrated peak area |
|---|---|
| 0.32 | 0.01 |
| 0.96 | 0.02 |

TABLE 3-continued

Values from the calibration curve

| Dopamine concentration [µM] | Integrated peak area |
|---|---|
| 1.60 | 0.03 |
| 2.24 | 0.05 |
| 2.88 | 0.06 |
| 32 | 0.61 |
| 64 | 1.26 |
| 96 | 1.89 |
| 128 | 2.52 |
| 160 | 3.18 |
| 192 | 3.79 |
| 224 | 4.44 |
| 256 | 5.09 |
| 288 | 5.69 |
| 320 | 6.24 |

All chromatograms, which support specificity, were comparable to those in Experiment 1. Average LOQ was observed to be 0.723 µM, and average LOD was observed to be 0.217 µM.

Stage 3

In Stage 3 (performed on a different instrument with a different column), samples were injected according to the following schedule: Calibration Standard Set 1, Transfected Lysates in triplicates, Calibration Standard Set 2, Spiked Transfected Lysates in triplicates, Calibration Standard Set 3; totaling 72 injections. A column cleaning protocol with 50% acetonitrile was performed in between each Standard Set and Transfected Lysate set. The 72 injections were repeated five consecutive times. The same samples were used that had been used for Experiment 2.

$R^2$ for the linear fit of the calibration curves was 0.999 for each of the repeats. Representative chromatograms were comparable to those in previous experiments described herein. For Experiment 3, criteria described herein were met for Specificity, Accuracy, and Precision. Average limit of quantitation and limit of detection were 0.625 µM and 0.188 µM respectively.

Intermediate precision was evaluated from a comparison of the calculated dopamine concentrations for transduced cell lysates, both in spiked and non-spiked samples. Acceptance criteria (% RSD must be ≤20%) from the qualification protocol are met. In the case of the lowest MOI, though, % RSD approaches 20. One possible reason is that for MOI 24, the average concentration (0.9 µM) is very close to the limit of quantitation, which was determined to be between 0.625 and 0.723 µM.

To assess the robustness of the mobile phase preparation in response to random variations in its components, three stock solutions each of sodium phosphate and octanesulfonic acid were prepared, and nine mobile phases were prepared by their combinations. Analyte mobility with the nine mobile phases will be assessed and compared using dopamine in reaction buffer. An overlay was done of the nine chromatograms showing the performance of the nine individual mobile phases prepared by mixing the three different sodium phosphate stock solutions with the three sodium octanesulfonate stock solutions. Elution times are shown in Table 4.

TABLE 4

Elution times for different combinations of mobile phases

| Mobile phase | Elution time (min) |
|---|---|
| P1:01 | 2.047 |
| P1:02 | 2.026 |
| P1:03 | 2.035 |
| P2:01 | 2.034 |
| P2:02 | 1.972 |
| P2:03 | 1.967 |
| P3:01 | 1.957 |
| P3:02 | 1.972 |
| P3:03 | 2.000 |
| Min | 1.957 |
| Max | 2.047 |
| Average | 2.001 |
| SD | 0.035 |
| % CV | 1.746 |

Dopamine mobility was observed to be affected by the composition of the mobile phase. The variation was a % CV equal to 1.75, and no discernible trend was observed. Efficient base-line separation of dopamine from the closest component (DTT) was observed throughout the experiment.

Based on the results of Experiment 2 and Experiment 3, acceptance criteria for theoretical plate count and peak tailing factor were determined for dopamine peaks in the calibration standard (level S8, 96 µM) and for cell lysates transduced with cell lysate reference standard at MOI 1563. The peak Asymmetry helps evaluating the column quality, and the theoretical Plates count is a measure for the separating capability of the column. Statistics are reported below in Table 5.

TABLE 5

Theoretical plate counts

| | Experiment 2 | | Experiment 3 | | | Experiment 2 | | Experiment 3 | |
|---|---|---|---|---|---|---|---|---|---|
| | Asymmetry | Plates | Asymmetry | Plates | | Asymmetry | Plates | Asymmetry | Plates |
| MOI 1563 | 1.14 | 5962 | 1.09 | 6275 | S8 | 1.14 | 6058 | 1.13 | 6298 |
| MOI 1563 | 1.14 | 6083 | 1.09 | 6313 | S8 | 1.13 | 6012 | 1.09 | 6517 |
| MOI 1563 | 1.13 | 6054 | 1.08 | 6390 | S8 | 1.12 | 5964 | 1.09 | 6615 |
| MOI 1563 | 1.14 | 5904 | 1.07 | 6540 | S8 | 1.14 | 5994 | 1.1 | 6529 |
| MOI 1563 | 1.14 | 5986 | 1.07 | 6619 | S8 | 1.16 | 5929 | 1.08 | 6617 |
| MOI 1563 | 1.13 | 5937 | 1.12 | 6607 | S8 | 1.12 | 5917 | 1.07 | 6677 |
| MOI 1563 | 1.13 | 5924 | 1.06 | 6561 | S8 | 1.13 | 5956 | 1.08 | 6577 |
| MOI 1563 | 1.12 | 5989 | 1.07 | 6595 | S8 | 1.16 | 5961 | 1.08 | 6632 |

TABLE 5-continued

Theoretical plate counts

| | Experiment 2 | | Experiment 3 | | | Experiment 2 | | Experiment 3 | |
|---|---|---|---|---|---|---|---|---|---|
| | Asymmetry | Plates | Asymmetry | Plates | | Asymmetry | Plates | Asymmetry | Plates |
| MOI 1563 | 1.12 | 5956 | 1.06 | 6606 | S8 | 1.16 | 5942 | 1.03 | 6562 |
| MOI 1563 | 1.16 | 5932 | 1.08 | 6439 | S8 | 1.12 | 5948 | 1.04 | 6521 |
| MOI 1563 | 1.14 | 5949 | 1.03 | 6447 | S8 | 1.12 | 5983 | 1.05 | 6499 |
| MOI 1563 | 1.14 | 5917 | 1.03 | 6452 | 88 | 1.14 | 5978 | 1.07 | 6428 |
| MOI 1563 | 1.14 | 5944 | 1.02 | 6408 | S8 | 1.15 | 5968 | 1.03 | 6443 |
| MOI 1563 | 1.12 | 5958 | 1.03 | 6443 | S8 | 1.11 | 6003 | 1.05 | 6457 |
| MOI 1563 | 1.12 | 5929 | 1.03 | 6438 | S8 | 1.14 | 5986 | 1.04 | 6409 |
| Average | 1.1 | 6219 | | | | 1.1 | 6246 | | |
| SD | 0.042 | 274 | | | | 0.041 | 287 | | |
| Acceptable | ≤1.23 | ≥5396 | | | | ≤1.23 | ≥5385 | | |

Acceptable values according to this qualification protocol are less than or equal to 1.23 for Asymmetry for both reference and calibration standards, and ≥5396 or ≥5385 for Plates for reference standard or calibration standard respectively. Given the relatively low number of measurements, and the limited number of tested columns, these numbers may be subject to review in the future.

The activities detailed in this Example demonstrate quantitation of dopamine in AAV2.AADC-transduced HT1080 cells lysates by reverse phase UHPLC with UV detection at 280 nm attains acceptable levels of specificity, linearity, precision, and. Limit of Detection (LOD) and Limit of Quantitation (LOQ) and acceptance criteria for peak shape for the reference and calibration standard were established, and the robustness of the preparation of the mobile phase used for the chromatographic separation was demonstrated.

Example 2. Production of AAV Vectors with a Baculovirus

AAV2.AADC was produced in a Sf9/baculovirus system. A cell bank was thawed to initiate Sf9 cell culture expansion in EFS AF™ Insect Cell Culture Medium (Expression Systems, LLC). The number of viable Sf9 cells was expanded using a shake flask and WAVE Bioreactor (GE Life Sciences) to enable rolling inoculation into the 200 L single use bioreactor. In the single use bioreactor, Sf9 cells were further expanded at 26-27° C. The AAV vector particles were then produced by infecting the Sf9 cells with baculoviruses (BIIC) which included BIIC-rep2/cap2 and BIIC-hAADC at 26° C. Chemical lysis of the Sf9 cells was performed at 18-25° C. to release the AAV vector particles from the cell nucleus. The material was clarified by removal of cell debris using immunoaffinity chromatography and anion exchange chromatography. The AAV vector particles were formulated in phosphate buffered saline (PBS) at a target concentration using ultrafiltration (UF) and diafiltration (DF), and the resulting formulation was cleared by nanofiltration and 0.2 µM filtration immediately prior to the final fill. 0.001% pluronic acid (F-68) was be added for a final fill resulting in the drug product.

Example 3. AADC Potency/Expression Assay: UHPLC-UV

Preparation of Reagents

Complete Media (DMEMc)—A 50 mL aliquot of Fetal Bovine Serum was thawed overnight at 4° C., and then pipetted into a new bottle of Dulbecco's Modified Eagle Medium (DMEM)+GLUTAMAX™ (within a biosafety cabinet). Following addition of FBS to the DMEM the resulting medium was filter sterilized using a 0.22 µM bottle top filter into a clean sterile 500 mL storage bottle, labeled as DMEMc and with the date of preparation and a 1 month expiration date from the date of preparation.

1×PBS+0.2% Triton X-100-495 mL of 1×PBS was combined with 5 mL of Triton X-100 (20% stock solution) in a buffer bottle and swirled to mix the solution. The resulting mixture was filtered though a 500 mL 0.2 µm bottle top filter into a 500 mL storage bottle and stored at room temperature.

Ascorbic acid—10 mM Ascorbic acid solution was prepared using HPLC water and aliquoted into 1.5 mL microcentrifuge tubes (450 µL each) and stored at −20° C.

Pargyline (10 mM)—10 mM pargyline solution was prepared using HPLC water and aliquoted into 1.5 mL microcentrifuge tubes (450 µL each) and stored at −20° C.

Dithiothreitol (100 mM)—100 mM dithiothreitol solution was prepared using HPLC water and aliquoted into 1.5 mL microcentrifuge tubes (450 µL each) and stored at −20° C.

Pyridoxal-5'-phosphate (2 mM)—2 mM pyridoxal-5'-phosphate solution was prepared using HPLC water and aliquoted into 4 mL amber glass vials (2.25 mL each) and stored at −20° C.

0.1 M Hydrochloric Acid (HC)—In a fume hood, 49.5 mL of HPLC water was added to a 50 mL conical tube (Eppendorf). 500 µL of 10N HCl was slowly added to the water in the 50 mL conical tube (Eppendorf). The tube was capped and mixed by vortex. The solution was stored in an acid storage cabinet at room temperature.

L-DOPA (20 mM)—20 mM L-DOPA solution was prepared using HPLC water and 0.1 M HCL. The resulting solution was sterile filtered using a 150 mL bottle-top filter (Corning, Inc.; catalog number 431161) affixed to a foil-wrapped 150 mL storage bottle and then aliquoted into 1.5 mL microcentrifuge tubes (1.25 mL each) and stored at −20° C. The L-DOPA stock concentration was measured using a NANODROP™, with the UV-V (pedestal, 1 mm pathlength) absorbance at 280 nm being measured in triplicate and averaged. Water was used to blank the instrument. The L-DOPA concentration was calculated using the following equation [[L-DOPA Solution Concentration (mM)=((Absorbance (280 nm))/((2.63 $cm^{-1}$ $mM^{-1}$)×0.1 cm))×10]]. The resulting concentration of the L-DOPA solution was 20±5 mM.

Dopamine (4 mM)—4 mM Dopamine solution was prepared using HPLC water. The resulting solution was sterile filtered using a 50 mL tube-top filter affixed to a foil-wrapped 50 mL conical tube and then aliquoted into 1.5 mL microcentrifuge tubes (500 µL each) and stored at −20° C.

The Dopamine concentration was measured using NANODROP™, with the average absorbance at 280 nm being measured (in triplicate) using the UV-V (pedestal, 1 mm pathlength). Water was used to blank the instrument. The Dopamine concentration was calculated using the following equation [[Dopamine Stock Concentration (mM)=((Absorbance (280 nm))/((2.07 cm−1 mM$^{-1}$×0.1 cm)×10)]]. The resulting concentration of the Dopamine solution was 4±0.1 mM.

0.5 M Perchloric Acid (PCA)—In a fume hood, 5.4 mL of 60% perchloric acid (9.2 M) was slowly added to 94.6 mL of HPLC water in a bottle, the bottle was capped and the swirled gently to mix. The solution was stored at room temperature.

0.724 M Sodium Phosphate monobasic solution (10× stock solution). pH 3.0—Using an analytical balance, 86.9 g of NaH$_2$PO$_4$ was measured. The 86.9 g of NaH$_2$PO$_4$ was dissolved in 900 mL HPLC water in a beaker, while stirring on a magnetic stir plate. The pH of the solution was checked using a pH probe. The pH of the solution to was adjusted to 3.0 by dropwise addition of phosphoric acid. The solution was transferred to a 1 L volumetric cylinder (removing the magnetic stir bar), and the volume was brought up to 1000 mL with HPLC water. The solution was filtered through a 500 mL bottle top filter attached to a 1 L storage bottle and stored at room temperature.

100 mM Octanesulfonic Acid—Using an analytical balance, 10.8 g sodium octanesulfonic acid was measured. The 10.8 g of octanesulfonic acid was dissolved in 400 mL HPLC water in a graduated cylinder, while stirring on a magnetic stir plate. The magnetic stir bar was removed, and the volume was brought up to 500 mL with HPLC water. The solution was filtered through a 500 mL bottle top filter attached to a 500 mL storage bottle. The solution was stored at room temperature.

AADC Mobile Phase (Buffer A)—HPLC water (700 mL), 100 mL of acetonitrile, 100 mL of 0.724 M NaH$_2$PO$_4$ (10× stock), and 32 mL of 100 mM octanesulfonic acid were combined in a 1000 mL graduated cylinder, and the volume was brought up to 1000 mL with HPLC water. The solution was transferred to a 1 L glass bottle and mixed well. The pH of the solution was checked using a pH probe. If necessary, the pH of the solution was adjusted to 3.0 using phosphoric acid. The buffer was degassed by sonication for 10 minutes.

50% Acetonitrile (Buffer B)—HPLC water (500 mL) and 500 mL of acetonitrile were combined in a 1000 mL graduated cylinder. The solution was transferred to a 1 L glass bottle and mixed well. The buffer was degassed by sonication for 10 minutes Seeding HT-1080 Cells The gene therapy vectors described herein are capable of transduction of cells in the putamen to express AADC enzyme in post-synaptic neurons. An AADC potency/expression assay is described herein that assesses potency of vector-delivered AADC gene therapy based on an EC$_{50}$ evaluation of the biological activity. This is an advance over available AADC ELISA kits that measure post-transduction protein concentration, which is not a direct measurement of biological activity. The potency assay in this Example analyzes cells that have been transduced with AADC-coding gene therapy vectors, AADC-mediated conversion of L-DOPA to dopamine in lysates produced from the cells, and measurement of the dopamine generated.

Specifically, HT1080 cells (ATCC® CCL-121) were seeded in DMEM+10% FBS using a P300 multichannel pipette (to avoid shearing) at a density of 5×10$^3$ cells/well in Corning cellbind 96-well plates and incubated at 37±2° C. for 24±2 hours. One 96-well plate was used for the testing two AADC vector samples (where each MOI is tested in triplicate). One extra plate was used for AAV2.AADC vector reference standard and positive control. Plates were sealed with porous adhesive film to reduce evaporation and maintain uniformity of gas exchange across the plate area. A lid was placed on top of each plate.

Alternatively, 100 μL of HT-1080 cells were seeded in complete media (DMEMc) at a density of 1×10$^4$ cells/well in a 96-well plate and incubated at 37±2° C. for 21±3 hours. One plate was used for the AAV2.AADC reference standard and a positive control.

Vector Calculations and Dilutions

In a biosafety cabinet, 10 mL of DMEM+10% FBS (per plate of cells) was warmed in a 50 mL conical tube (Eppendorf) in a water bath at 37° C. for approximately 5 to 30 minutes. The volume of vector and DMEM+10% FBS to add to the HT1080 cells was calculated for each vector, positive control, and reference standard. Vector dilutions were performed in triplicate and tested in adjoining wells of cells. To reduce error, the amount of vector added to the DMEM+10% FBS was greater than 20 μL but less than 200 μL. If the calculated volume of vector was out of this range, the vector was diluted in 1×PBS (ex. 1:5, 1:10, 1:20). The amount of vector needed to achieve an MOI of 200,000 was calculated using the ddPCR titer of the vector(s). If a dilution of vector stock was required, the dilution factor was included in the calculations below, and if no dilution of vector stock was necessary, the dilution factor was 1.

$$\text{Volume of Vector}(\mu L) = \frac{200{,}000 \text{ MOI} \times 1x10^4 \frac{\text{cells}}{\text{well}} \times \text{dilution factor} \times 10}{ddPCR \text{ titer}\left(\frac{vg}{mL}\right) \times \frac{1 \text{ mL}}{1000 \mu L}}$$

The volume of the vector required was subtracted from a total volume of 200 μL to determine the amount of DMEM+10% FBS required.

Volume of DMEM+10% FBS(μL)=200 μL−Volume of Vector(μL)

The vector dilutions were prepared in 1×PBS in a 1.5 mL Safe-Lock Microcentrifuge tubes (Eppendorf, Cat #022363212 or equivalent). In a separate plate, 100 μL of DMEMc was added to all wells but the top row. The AAV2.AADC vector (diluted to a starting concentration of 2×10$^8$ vg/μL in IX PBS) was then diluted 1:8 in DMEMc, and then 200 μL was added to the top row of a plate. The solution in the top row was then serially diluted down the plate. Two-fold serial dilutions were performed by adding 100 μL to each successive well using a multichannel pipette. Each dilution was mixed prior to moving to the next dilution, and pipette tips were changed between dilutions. An example of a dilution scheme for the vector is shown in Table 6.

TABLE 6

Vector dilution scheme

| Dilution Number | MOI | Warmed DMEM + 10% FBS | Vector |
|---|---|---|---|
| Dilution D1 | 200,000 | 130.06 μL | 69.94 μL of 1:10 dil of stock |
| Dilution D2 | 100,000 | 100 μL | 100 μL of D1 |
| Dilution D3 | 50,000 | 100 μL | 100 μL of D2 |

TABLE 6-continued

Vector dilution scheme

| Dilution Number | MOI | Warmed DMEM + 10% FBS | Vector |
|---|---|---|---|
| Dilution D4 | 25,000 | 100 µL | 100 µL of D3 |
| Dilution D5 | 12,500 | 100 µL | 100 µL of D4 |
| Dilution D6 | 6,250 | 100 µL | 100 µL of D5 |
| Dilution D7 | 3,125 | 100 µL | 100 µL of D6 |
| Dilution D8 | 1,563 | 100 µL | 100 µL of D7 |
| Dilution D9 | 781 | 100 µL | 100 µL of D8 |
| Dilution D10 | 391 | 100 µL | 100 µL of D9 |
| Dilution D11 | 195 | 100 µL | 100 µL of D10 |
| Dilution D12 | 98 | 100 µL | 100 µL of D11 |
| Dilution D13 | 49 | 100 µL | 100 µL of D12 |
| NEG | 0 | 100 µL | — |

Cell Transduction

The 96-well cell culture plate(s) were removed from the incubator, and the cells were confirmed to appear healthy and be approximately 60-80% confluent using an inverted phase contrast microscope. The plate(s) were placed in the biosafety cabinet (BSC).

Using a P20 multichannel pipette, the vector dilutions (20 µL) were added to the cells one row at a time at the liquid surface on the side of the well to avoid disruption of the cell monolayer. Plates were sealed with porous adhesive film to reduce evaporation and maintain uniformity of gas exchange across the plate area, and a lid was placed on top of the plate. Then, the cells were gently rocked in a figure-eight manner 5-10 times to evenly distribute the vector and returned to the incubator at 37±2° C. for 48±4 hours (usually 44-52 hours)

After transduction, media was aspirated one well at a time using an unfiltered P200 pipette tip affixed to a serological pipette in a vacuum line. Then, the cells were washed with 100 µL 1×PBS applied to the side of each well with a P200 multichannel pipette. The pipette tip was placed at the liquid surface on the side of the well to avoid disruption of the cells. Cells were washed by adding 100 µL 1×PBS to the side of the wells using a P200 multichannel pipette while taking care to avoid disturbing the cells. The plate was gently rocked side to side. The 1×PBS was aspirated from the wells using an unfiltered P200 pipette tip affixed to a serological pipette in a vacuum line.

Cell Lysis

For two 96-well plates, a 10 mL solution of Lysis Buffer was prepared by adding 100 µL of 100× Halt Protease Inhibitor Cocktail to 9.9 mL of 1×PBS+0.2% Triton X-100. The solution was prepared in multiples of 5 mL depending on the number of plates being run. The Lysis Buffer was prepared on the day of use, and any solution that was not used in the lysis of the cells was discarded.

Cells were harvested 48±4 hours post-transduction. Using a P50 multichannel pipette, the cells were lysed with 50 µL of Lysis Buffer (50 µL of 1× Halt Protease Inhibitor Cocktail+1×PBS+0.2% Triton X100) in each well. The plates were sealed around the edges with parafilm. The plates were frozen at −80° C. for 30 minutes or up to 72 hours, thawed at room temperature until all the ice melted. Using a P50 multichannel pipette, each row of cell lysates was mixed by pipetting the lysates up and down several times. The lysates were transferred into a 96-well PCR plate and covered with sealing film. The 96-well PCR plate was centrifuged at 35004000 RPM, for example 3750 RPM, for 10 minutes to pellet the cellular debris. The supernatants ("clarified cell lysates") were transferred to a new plate (lysates can also be stored at −80° C. for up to 72 hours) using a P50 multi-channel pipette, while taking care to avoid disrupting the cell pellet at the bottom of the well, prior to running the AADC reaction. The plate was covered with sealing film.

Dopamine Standard Curve

An 11-point dopamine standard curve was prepared by diluting the 4 mM dopamine stock in 1×PBS+0.2% Triton X-100 in 1.5 mL Safe-Lock Microcentrifuge tubes (Eppendorf, Cat #022363212 or equivalent). The dilutions are shown in Table 7. The calculations for standards S1, S2, and S3 were adjusted if the dopamine stock was not exactly at 4 mM.

TABLE 7

Dopamine standard curve dilutions

| Dopamine Standard | 1 × PBS + 0.2% Triton (µL) | Dopamine (µL) | Target Conc. (µM) | Final Conc. (µM) |
|---|---|---|---|---|
| S1 | 12.50 | 187.50 of stock | 3750 | 300 |
| S2 | 43.75 | 156.25 of stock | 3125 | 250 |
| S3 | 75 | 125 of stock | 2500 | 200 |
| S4 | 100.00 | 100 of S1 | 1875 | 150 |
| S5 | 100.00 | 100 of S3 | 1250 | 100 |
| S6 | 100.00 | 100 of S5 | 625 | 50 |
| S7 | 100.00 | 100 of S6 | 312.5 | 25 |
| S8 | 160.00 | 40 of S6 | 125 | 10 |
| S9 | 100.00 | 100 of S8 | 62.5 | 5 |
| S10 | 180.00 | 20 of S9 | 6.25 | 0.5 |
| SNEG | 100 | — | 0 | 0 |

In a 96-well PCR plate, AADC Reaction Buffer (180 µL was combined with 20 µL of corresponding dopamine standard in eleven consecutive wells (for example, A 1-A11) using a P200 multichannel pipette. 20 µL of the corresponding dopamine standard was added to each of the eleven wells to simulate the addition of the AADC cell lysate to the AADC reaction. 10 µL of HPLC water was added to each well to serve as the "mock L-DOPA addition" 0.40 µL of cold 0.5 M perchloric acid was added to each well using a P200 multichannel pipette to "mock quench" the reaction. Each well was pipetted to mix. The plate was sealed with heat sealing film using the Bio-Rad PX1™ PCR plate sealer, and the plate was placed in the UHPLC autosampler or kept at 4° C. until ready to use.

AADC Reactions

AADC reactions were prepared by the following protocol. If frozen, the cell lysates (stored in 96-well plates) were thawed on the benchtop. One tube of Positive Control Cell Lysate was also thawed on the benchtop and placed on ice or at 4° C. once thawed.

Tubes of 20 mM L-DOPA required for the experiment were thawed on the benchtop. Once thawed, they were placed on ice or at 4° C. and used the same day or discarded. L-DOPA (10 µL of 20 mM) was added to each well, and the plates were incubated at 37° C. for 30 minutes. Then, the plates were transferred to an ice bath (2-8° C.). The reaction was quenched by adding pre-chilled 0.5 M perchloric acid (PCA) (40 µL).

Using either a P200 multichannel pipette or repeat pipetter, 180 µL of AADC Reaction Buffer was added to each well to be used in a 96-well PCR plate. In addition, 180 µL of AADC Reaction Buffer was added to different wells as positive control AADC Reactions. 20 µL of AADC Cell Lysate Positive Control was added and pipetted to mix.

To the remaining wells containing Reaction Buffer, 20 µL of AADC cell lysate was added using a P20 multichannel pipette and mixed with the pipette.

The plate was covered with sealing film and spun for 15 seconds in a 96-well plate centrifuge to collect the contents at the bottom of the wells. The plate was placed in a 37° C. incubator for 5±1 minutes.

The plate was removed from the incubator and the sealing film was discarded. The contents of L-DOPA tubes were transferred to the reagent reservoir. 10 µL of 20 mM L-DOPA solution was added to each well using a P20 multichannel pipette, and then mixed by pipetting. Once L-DOPA is added to the plate, the reaction will proceed rapidly; therefore, these steps are highly time sensitive.

The plate was covered with sealing film and placed in an incubator set at 37° C. for 30±1 minutes. A large ice pan was filled with ice. A 15 mL conical tube (Eppendorf) containing 12 mL of 0.5 M perchloric acid and a plastic 96-well plate holder was chilled by placing on the ice. After the 30±1 minutes incubation, the plate was transferred to an ice bath for 5±1 minutes to cool to 2-8° C. After the 5±1 minutes, the plate immediately was transferred to the chilled plate holder, and the sealing film was removed.

The prechilled (2-8° C.) 0.5 M perchloric acid (PCA) was transferred to a reagent reservoir. 40 µL of prechilled 0.5 M PCA was added to quench the reaction using a P200 electronic multichannel pipette. The plate was sealed with heat sealing film using the Bio-Rad PX1™ Plate Sealer.

UHPLC-UV Analysis

UHPLC-UV was used for detection of dopamine in the samples. The following protocol was used to conduct UHPLC-UV. Dopamine standards and samples were placed in the prechilled UHPLC autosampler set to 4° C. A new guard cartridge was inserted into the guard column (BDS Hypersil guard column, 3×10 mm, 3 µm, cat #28105-013001 (ThermoScientific) and affixed to the 50 mm C18 column. The lines for Buffer A1 and Buffer B1 were flushed, and 10 mL of 50% Acetonitrile (Buffer B) and, separately, 10 mL of AADC Mobile Phase (Buffer A) were run through the column. Prior to the running of dopamine standards or samples, a series of ten test injections was performed to ensure that the column and the UHPLC system were functioning properly. Typically, ten injections of Dopamine Standard S1 were sufficient. The samples were run on a 50 mm C18 column at 280 nm for 3 minutes with the following UHPLC run parameters: 1) Pump: 0.5 mL/min AADC Mobile Phase (Buffer A); 2) Injection: 5 µL of sample; and 3) Column Temp: 35° C.

After approximately every 12 samples, a UV Cleaning Step was performed to clean the column and equilibrate the UV detector. 0.5 mL/min 50% Acetonitrile (Buffer B) for 3 minutes was followed by 0.5 mL/min AADC Mobile Phase (Buffer A) for 7 minutes. Following the UV Cleaning Step, an injection of Dopamine Standard SNEG was used to equilibrate the column. The column was flushed with 10 mL of 50% Acetonitrile (Buffer B) to clean it prior to storage. The dopamine peaks were integrated using the auto integrate function in the CHROMELEON™ Chromatography Data System software (Thermo Scientific).

The dopamine peak areas were correlated to the dopamine standard curve using the CHROMELEON™ Chromatography Data System software (Thermo Scientific) (dopamine standard points: 300, 250, 200, 150, 100, 50, 25, 10, 5, 0.5 µM). The dopamine concentration from all replicates for each MOI was plotted in GraphPad software (Prism) or an equivalent data analysis package. The data was fit to a four-parameter logistic curve ([Agonist] vs. response-Variable slope (four parameters)):

$$\text{Absorbance} = D + \frac{A - D}{1 + \left(\frac{\text{Concentration}}{C}\right)^B},$$

where A=Upper asymptote ("Top"); B=Slope of dynamic range ("Hillslope"); C=EC$_{50}$ (EC$_{50}$); and D=Lower asymptote ("Bottom").

Relative potency was expressed as a shift in EC$_{50}$ from the reference standard. AADC Relative Potency was expressed as the ratio of the EC$_{50}$ values of the Reference Standard to the Test Sample using the following equation:

$$\text{Relative Potency} = \left(\frac{EC50_{REFERENCE}}{EC50_{TEST\ SAMPLE}}\right) \times 100\%$$

Optimization of L-DOPA Concentration

Eight different L-DOPA stock concentrations were prepared at the following L-DOPA concentrations: 0.3 mM, 0.5 mM, 1 mM, 5 mM, 10 mM, 20 mM, 50 mM, 97 mM. Over a series of three experiments. AADC Reactions were performed using previously prepared AADC cell lysates and the various concentrations of L-DOPA stock, as in Example 3. The resulting dopamine dose response curves indicated that peak dopamine production is generated with 20 mM L-DOPA.

AADC Reaction Incubation Time Robustness

A potential source of variability observed in the upper asymptote of a dose response curve involves the timing of the AADC Reaction. If the enzymatic reaction is prematurely stopped or allowed to proceed for additional time, it will likely have an impact on the amount of dopamine product generated. Three portions of the reaction that were investigated for their robustness: (1) the Reaction Buffer and cell lysate incubation at 37° C. for 5 minutes, (2) the addition of L-DOPA to initiate the AADC Reaction that proceeds at 37° C. for 30 minutes, and (3) the 5 minute hold on ice to slow the reaction prior to quenching with perchloric acid (PCA).

AADC Reactions were set up with previously made AADC cell lysate and Reaction Buffer (as in Example 3), and were incubated at 37° C. for either 2, 5, or 10 minutes prior to the addition of L-DOPA, and the rest of the reaction proceeded normally. In another test, the AADC Reaction time was varied from 28, 30, or 32 minutes prior to moving the plate to ice. And finally, the upfront incubation step and AADC Reaction steps were allowed to proceed normally, but the final step on ice was varied from 3, 5, or 7 minutes prior to quenching. Resulting data indicate that there are slight difference in dopamine production based on changes in incubation time for Step 1, Step 2 and Step 3, with favorable conditions as follows: Step 1: 37° C. for 5±2 minutes, Step 2: 37° C. for 30±2 minutes, Step 3: on ice for 5±2 minutes.

Intra- and Inter-Assay Variability

A single experiment performed by one operator, four plates containing both a positive control and a reference standard used to run the AADC Activity Assay. Triplicate data points were averaged for each MOI per plate run, and the results for each of the four plates were fit to a fourparameter curve. To obtain a more meaningful comparison, the bottom asymptote (D) values were all forced to zero prior to performing the four-parameter fit, as this value seemed to contribute a great source of variability within the four parameters, with little overall impact to the curve fitting.

Following the four-parameter fit, the largest source of variability observed within the four variables originates from the EC50 value for both data sets. Within a single assay run containing four plates, the average EC50 value for the positive control is 12,779.75 with a 10.95% CV, while for the reference standard it was 8964.75 with a CV of 17.87%. Although the % CV values are slightly high for a standard assay, these numbers are considered within acceptable range for a cell-based potency assay for which 10-30% CV is typically set for both assay and sample acceptance criteria.

Example 4. AADC Potency/Expression Assay: UHPLC-ECD

Preparation of Reagents

Complete Media (DMEMc)—A 55 mL aliquot of Fetal Bovine Serum was added into a new bottle of Dulbecco's Modified Eagle Medium (DMEM)+GLUTAMAX™ (within a biosafety cabinet). 5.5 mL of Penicillin/Streptomycin was added to the bottle, which was then swirled to mix the solution. The resulting mixture was filtered and stored at room 2-8° C.

1×PBS+0.2% Triton X-100-990 mL of 1×PBS was combined with 5 mL of Triton X-100 (20% stock solution) in a buffer bottle and swirled to mix the solution. The resulting mixture was filtered and stored at room temperature.

Ascorbic acid (10 mM)—10 mM Ascorbic acid solution was prepared using 10 mL of HPLC water and 0.0176 g of ascorbic acid, adjusted to target concentration. The mixture is aliquoted into tubes and stored at 2-8° C.

Pargyline (10 mM)—10 mM pargyline solution was prepared using 10 mL of HPLC water and 0.0196 g of pargyline, adjusted to target concentration. The mixture is aliquoted into tubes and stored at 2-8° C.

Dithiothreitol (100 mM)—100 mM dithiothreitol solution was prepared using 10 mL of HPLC water and 0.1543 g of dithiothreitol, adjusted to target concentration. The mixture is aliquoted into tubes and stored at 2-8° C.

Pyridoxal-5'-phosphate (2 mM)—2 mM pyridoxal-5'-phosphate solution was prepared using 35 mL of HPLC water and 0.0173 g of pyridoxal-5'-phosphate, adjusted to target concentration. The mixture is aliquoted into tubes and stored at 2-8° C.

0.1 M Hydrochloric Acid (HCl)—In a fume hood, 49.5 mL of HPLC water was added to a 50 mL conical tube. 500 µL of 10N HCl was slowly added to the water in the 50 mL conical tube. The tube was capped and vortexed to mix. The solution was stored in an acids cabinet at room temperature.

L-DOPA (0.3 mM)—0.3 mM L-DOPA solution was prepared using 10 mL of HPLC water and 0.00986 g of —DOPA, adjusted to target concentration. The mixture is filtered into a foil-wrapped 150 mL storage bottle and then aliquoted into 1.5 mL microcentrifuge tubes (1.25 mL each) and stored at −20° C. The L-DOPA stock concentration was measured using NANODROP™, with the average absorbance at 280 nm being measured (in triplicate) using the UV-V (pedestal, 1 mm pathlength). Water was used to blank the instrument. The L-DOPA concentration was calculated using the following equation [[L-DOPA Solution Concentration (mM)=((Absorbance (280 nm))/((2.63 cm$^{-1}$ mM$^{-1}$)×0.1 cm))×10]]. The resulting concentration of the L-DOPA solution was 0.3 mM.

Dopamine (1 mM)—1 mM Dopamine solution was prepared without exposure to light using 10 mL of 0.1 M HCl and 0.00948 g of dopamine, adjusted to target concentration. The mixture is filtered into a foil-wrapped 50 mL storage tubes and then aliquoted into 1.5 mL microcentrifuge tubes (0.5 mL each) and stored at −20° C. The Dopamine concentration was measured using NANODROP™, with the average absorbance at 280 nm being measured (in triplicate) using the UV-V (pedestal, 1 mm pathlength). Water was used to blank the instrument. The Dopamine concentration was calculated using the following equation [[Dopamine Stock Concentration (mM)=((Absorbance (280 nm))/((2.07 cm−1 mM$^{-1}$×0.1 cm)×10)]]. The resulting concentration of the Dopamine solution 1 mM.

0.5 M Perchloric Acid (PCA)—In a fume hood, 5.4 mL of 60% perchloric acid (9.2 M) was slowly added to 94.6 mL of HPLC water in a bottle, the bottle was capped and the swirled gently to mix. The solution was stored at room temperature.

Reaction Buffer—300 mL of nuclease-free water was added to a 1 L bottle wrapped with aluminum foil. The following was added to the bottle: 50 mL of sodium phosphate pH 7.2 (500 mM); 5 mL of ascorbic acid (10 mM); 5 mL of pargyline (10 mM); 5 ml of dithiothreitol (100 mM): 25 mL pyridoxal-5'-phosphate (2 mM); 100 µL EDTA (500 mM). The solution is mixed and stored at −20° C.

Seeding HT-1080 Cells, Dilutions and Transduction

HT1080 cells (ATCC® V CCL-121) were seeded in complete media (DMEMc) at a density of 1×10$^4$ cells/well in 24 or 96-well plates and incubated at 37±2° C. for 18-24 hours. In a separate plate, 100 µL of DMEMc was added to all wells but the top row. The AAV2.AADC vector (diluted to a starting concentration of 2×10$^8$ vg/µL in 1×PBS) was then diluted 1:8 in DMEMc and then added (200 µL) to the top row of plate. The solution in the top row was then serially diluted down the plate as shown in Table 8. Vector dilution (20 µL) were added to the cells and then the cells were returned to the incubator for a desired transduction time (usually 44-52 hours).

TABLE 8

Vector dilution scheme

| Dilution Number | MOI | Warmed DMEMc | Vector |
|---|---|---|---|
| Dilution D1 | 25,000 | — | 200 µL |
| Dilution D2 | 12,500 | 100 µL | 100 µL of D1 |
| Dilution D3 | 6,250 | 100 µL | 100 µL of D2 |
| Dilution D4 | 3,125 | 100 µL | 100 µL of D3 |
| Dilution D5 | 1,563 | 100 µL | 100 µL of D4 |
| Dilution D6 | 781 | 100 µL | 100 µL of D5 |
| Dilution D7 | 391 | 100 µL | 100 µL of D6 |
| Dilution D8 | 195 | 100 µL | 100 µL of D7 |
| Dilution D9 | 98 | 100 µL | 100 µL of D8 |
| Dilution D10 | 49 | 100 µL | 100 µL of D9 |
| NEG | 0 | 100 µL | — |

Cell Lysis and AADC Reaction

After transduction, media was aspirated, then the cells were washed in PBS and lysed with 50 µL of Lysis Buffer (50 µL of 1× Halt Protease Inhibitor Cocktail+1×PBS+0.2% Triton X100). The plates were frozen at −80° C. for 30 minutes up to 72 hours, thawed and then centrifuged (3750 RPM for 10 minutes). The supernatants ("cell lysates") were transferred to a new plate (lysates can also be stored at −80° C. for up to 72 hours) prior to running the AADC reaction.

Reaction Buffer (180 µL) was combined with 20 µL of cell lysate, and incubated at 37° C. incubator for 5 minutes. L-DOPA (10 µL of 0.3 mM) was added to each well, the plates were incubated at 37° C. for 30 minutes, and then transferred to an ice bath (2-8° C.). The reaction was quenched by adding prechilled 0.5 M perchloric acid (PCA)

(40 µL). Samples were then analyzed using Ultra High-Pressure Liquid Chromatography coupled to an electrochemical detector (UHPLC-ECD).

UHPLC-ECD Analysis

UHPLC-ECD was used for detection of dopamine in the samples. Samples were analyzed using Ultra High-Performance Liquid Chromatography coupled to an electrochemical detector (UHPLC-ECD) on a 50 mm C18 column (BDS Hypersil C18 reverse phase column, 3×50 mm, 5 µm, cat #28105-053030 (ThermoScientific)) with the following run parameters: Pump; 0.5 ml/min Test Mobile Phase of ThermoFisher #70-3829 (organic mixture of acetonitrile, phosphate buffer, and an ion paring agent); Injection: 5 µL of sample; Run Time: 2.5 minutes; ECDRS1: 250 mV, ECDRS2: 400 mV; data collection rate: 10 Hz; Column Temp: 35° C. Dopamine peaks were analyzed using Chromeleon software.

Figure 5A:
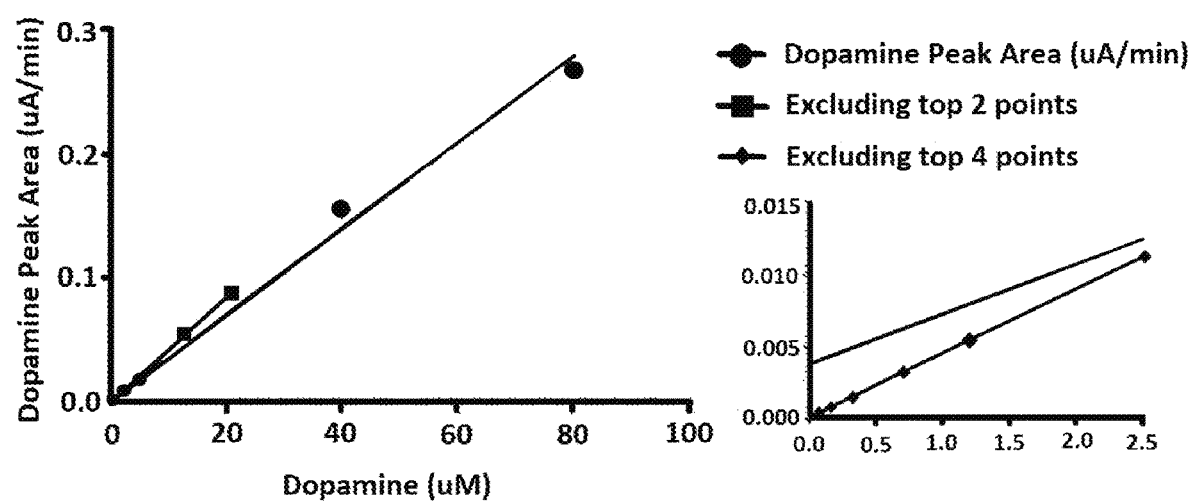
FIG. 5A-5B show the standard curves and chromatograms for a dopamine standard curve.
Figure 5B:
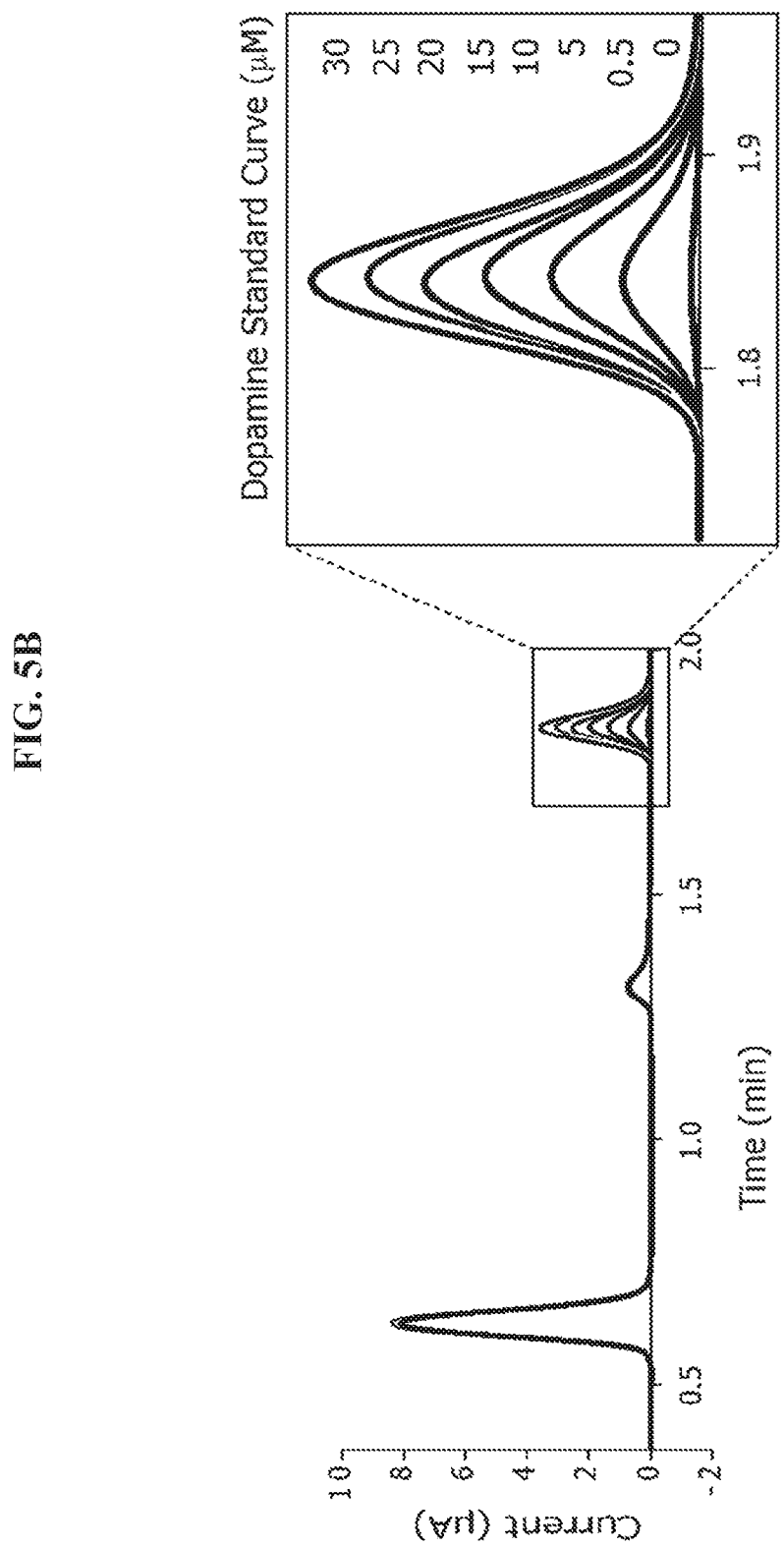

The UHPLC-ECD electrochemical response to dopamine is measured in current (µA). To convert this measurement to the amount of dopamine generated, a dopamine standard curve is utilized. Dopamine was solubilized using 0.1 M HCl and the concentration was determined using the absorbance at 280 nm (extinction coefficient=2.07 $cm^{-1}$ $mM^{-1}$). The extinction coefficient was determined empirically. The dopamine was diluted to 1 mM in water, aliquoted, and frozen at −20° C. The absorbance at 280 nm of the frozen stock is measured when it is thawed for quality assurance. The 1 mM stock was then diluted to the top standard point (80 µM final concentration) in AADC Reaction Buffer. This standard was then serial diluted (2-fold dilutions) in reaction buffer to generate the standard curve. When analyzing each sample in triplicate, there was very little difference in the chromatograms, as shown in FIG. 5B.

When plotting the raw dopamine area, there was some non-linearity at the two most concentrated points. The removal of these two points from the standard curve allows the best-fit line to more closely represent the lower concentrations (FIG. 5A). For reference, the lowest MOI that was measured for AAV2.AADC (49 vg/cell) has a dopamine area of approximately $1×10^{-3}$ µL/min. To allow for quantification of dopamine levels for the lower MOIs, the Y-intercept of the selected best-fit line was as close to zero as possible. The Y-intercept with all of the points in the standard curve was $3.9×10^{-3}$ µA/min. By removing the top two points in the standard curve, the Y-intercept was reduced to $4.0×10^{-4}$ µA/min, which was less than the lowest MOIs. Removing the top four points in the standard curve reduced the Y-intercept to $7.3×10^{-5}$ µA/min. While the removal of the top four points improved the sensitivity at low concentrations of dopamine, it also reduced the range for the higher concentrations of dopamine. For the highest MOIs in the dose response ranges tested, the dopamine areas ranged from $3×10^{-2}$ to $6×10^{-2}$ µA/min. If more than the top two points of the standard curve were removed, then the dopamine concentrations for the higher MOIs could not be accurately determined.

Determination of Stability of Reference Standard

Figure 6:
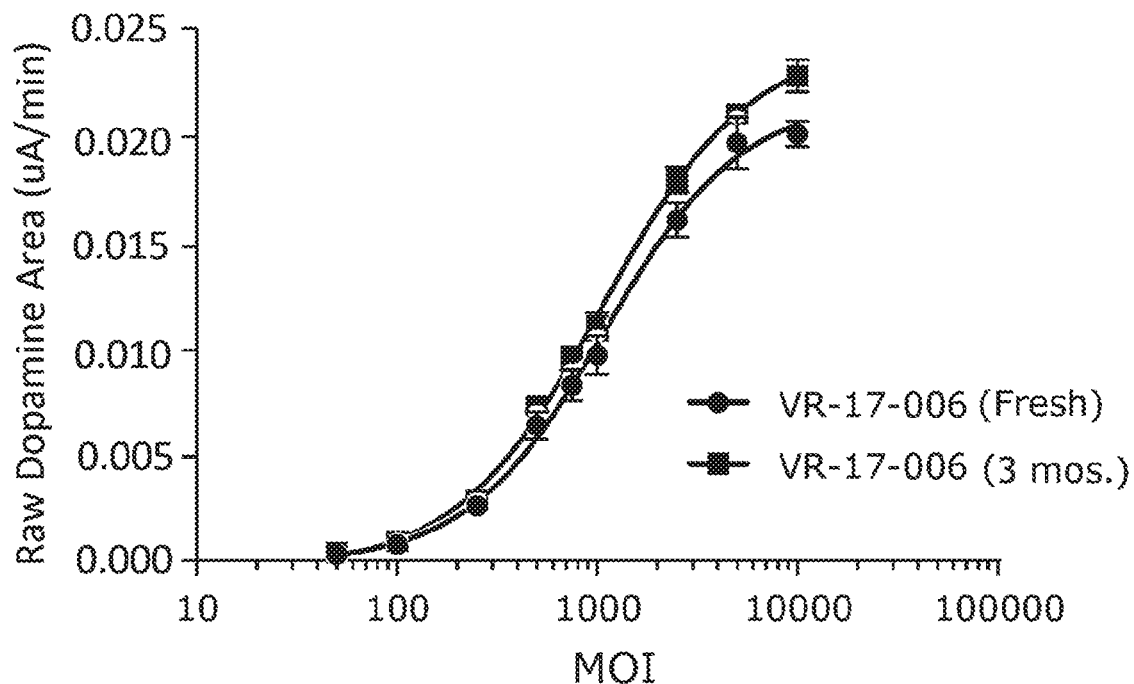
FIG. 6 shows the comparison of enzyme activity of two vials of AAV2.AADC reference standard thawed three months apart and stored at 2-8° C.

The short-term stability at 2-8° C. of the AAV2.AADC vector Reference Standard used in Example 4 (titer of $1.5×10^9$ vg/µL, vialed at 250 µL per vial; highest dose in the dose-response range approximately $2×10^8$ vg per well) was analyzed. Two vials were tested in parallel. One vial was freshly thawed and the other was thawed 3 months prior and stored at 2-8° C. The data between the two samples were comparable (FIG. 6, Table 9). These data indicate that the Reference Standard can be held at 2-8° C. for at least up to 3 months.

TABLE 9

Four-Parameter Curve Fit Data for the Curves in FIG. 6

| Sample | Bottom | Hillslope | Top | $EC_{50}$ |
| --- | --- | --- | --- | --- |
| AAV2.AADC (fresh) | 7.65E−05 | 1.276 | 0.01954 | 1087 |
| AAV2.AADC (3 months) | −1.49E−04 | 1.201 | 0.02186 | 1061 |

Analysis of Lysate Sample Stability

A short-term stability study was conducted on the cell lysate from Example 4.

The lysate samples were held in a 2-8° C. refrigerator, −20° C. freezer, and −80° C. freezer. The lysate was observed to have some loss of activity after the first day at −80° C., followed by a shallow decline in activity after 30 days. In contrast, the cell lysates held at −20° C. and 2-8° C. had a rapid loss of activity over the first 4 days.

Additionally, the lysates were freeze/thawed several times to determine if there is a loss of AADC activity after multiple freeze/thaws. After repeated freeze/thaw cycles at −80° C., a representative lysate was observed to have a decrease (about 40%) in dopamine generation between the first and second freeze/thaw but stabilized after the initial drop.

Lysate samples were also tested to analyze the effect of exposure to heat and UV. The results shown in FIG. 7 and Table 10 showed significant effect of exposure to heat and UV on the lysate sample.

TABLE 10

Figure 7:
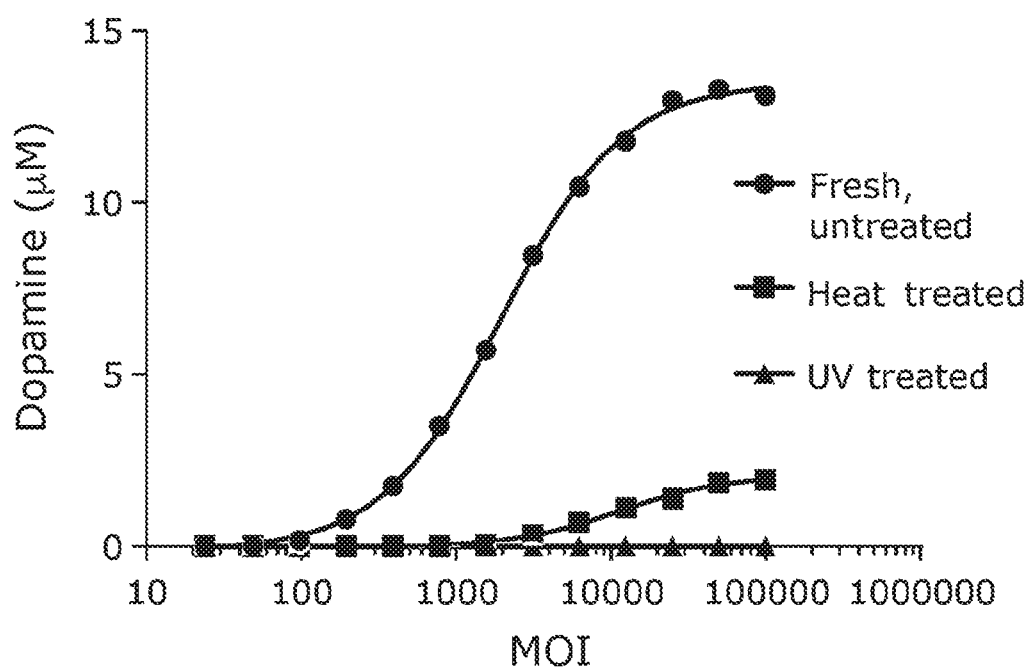
FIG. 7 shows a comparison of enzymatic activity between heat treated samples, UV treated samples, and untreated samples.

Four-Parameter Curve Fit Data for the Curves in FIG. 7

| Vector Sample | Bottom | Hillslope | Top | $EC_{50}$ | % of Reference |
| --- | --- | --- | --- | --- | --- |
| Fresh, Untreated | −0.1349 | 1.122 | 13.48 | 1983 | 100 |
| Heat Treated | −0.02323 | 1.275 | 2.062 | 11266 | 17.60 |
| UV Treated | 0 | * | * | * | * |

Determination of an Appropriate Dose Range (MOI) for Potency Assay

AADC ELISA assays in the art generally use a limited dose range in transductions (63, 125, 250, 500, and 1000 vector genomes per cell). To measure potency relative to a reference standard accurately a full dose response range is required, including both upper and lower asymptotes when plotting MOI (multiplicity of infection) on a log scale.

To determine an appropriate range for this potency assay, HT1080 cells were transduced with an AAV2.AADC vector at an amount of 10 to 10.000 vector genomes (VG) per cell using the methods described in Example 4. The cells were lysed, and enzyme activity was determined, which is shown in FIG. 1. A dose response (dopamine vs. MOI) was plotted and the data was fit to a 4-parameter logistic curve. For this analysis, the fit parameters were used as the readout. Using this dose range of 10 to 10,000 vg/cell, a lower asymptote was observed between 10-25 vector genomes per cell. An upper asymptote was observed at MOIs greater than 2500 vector genomes per cell.

Increasing Throughput of the AADC Potency Assay

The assay described in Example 4F was performed using a 24-well plate. Similar assays were run with %-well plates to test the viability of the 96-well plates for higher assay throughput.

Figure 2:
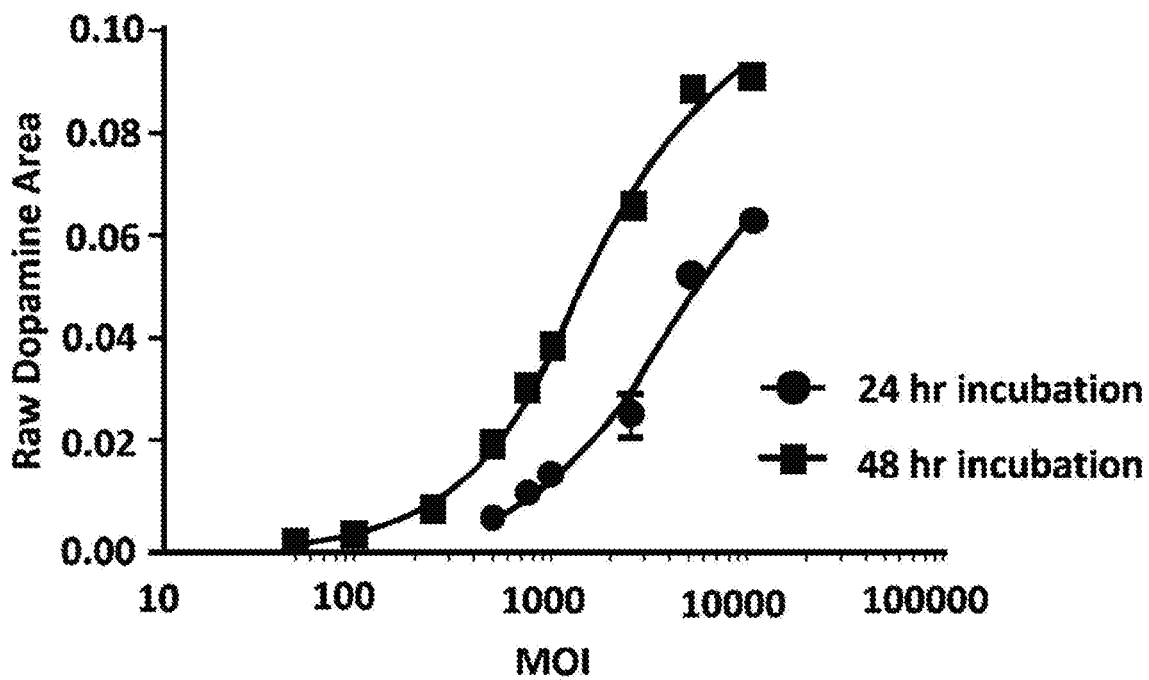
FIG. 2 shows the in vitro dose response curve to the transduction of HT1080 cells using 96-well plates.

First, 96-well plates were tested for variability based on incubation time. HT1080 cells were transduced for 24 or 48 hours in 96-well plates with an AAV2.AADC vector, after which time cells were lysed using the Lysis Buffer described in Example 4. The 24 hour and 48-hour dose response curves in 96-well plates showed transduction time dependence, with a greater AADC activity being seen in the 48-hour transduction time sample (FIG. 2). Nine different MOIs, from 50-10,000 were analyzed. Each dose was tested in triplicate. The measurements of activity in each biological replicate were consistent (coefficient of variance <10%).

Next, 96-well plates were tested for inter-assay variability and reproducibility. An AAV2.AADC vector was used as a reference standard and was analyzed eight times in five separate runs of the AADC potency assay of Example 4. The vector was either freshly prepared (labeled as "fresh") or stored at −80° C. for either 1 or 3 months. The consistency and variability of these runs were examined. The activity for each sample was determined (FIG. 3) and the variability of the data is summarized in Table 11 below.

TABLE 11

Figure 3:
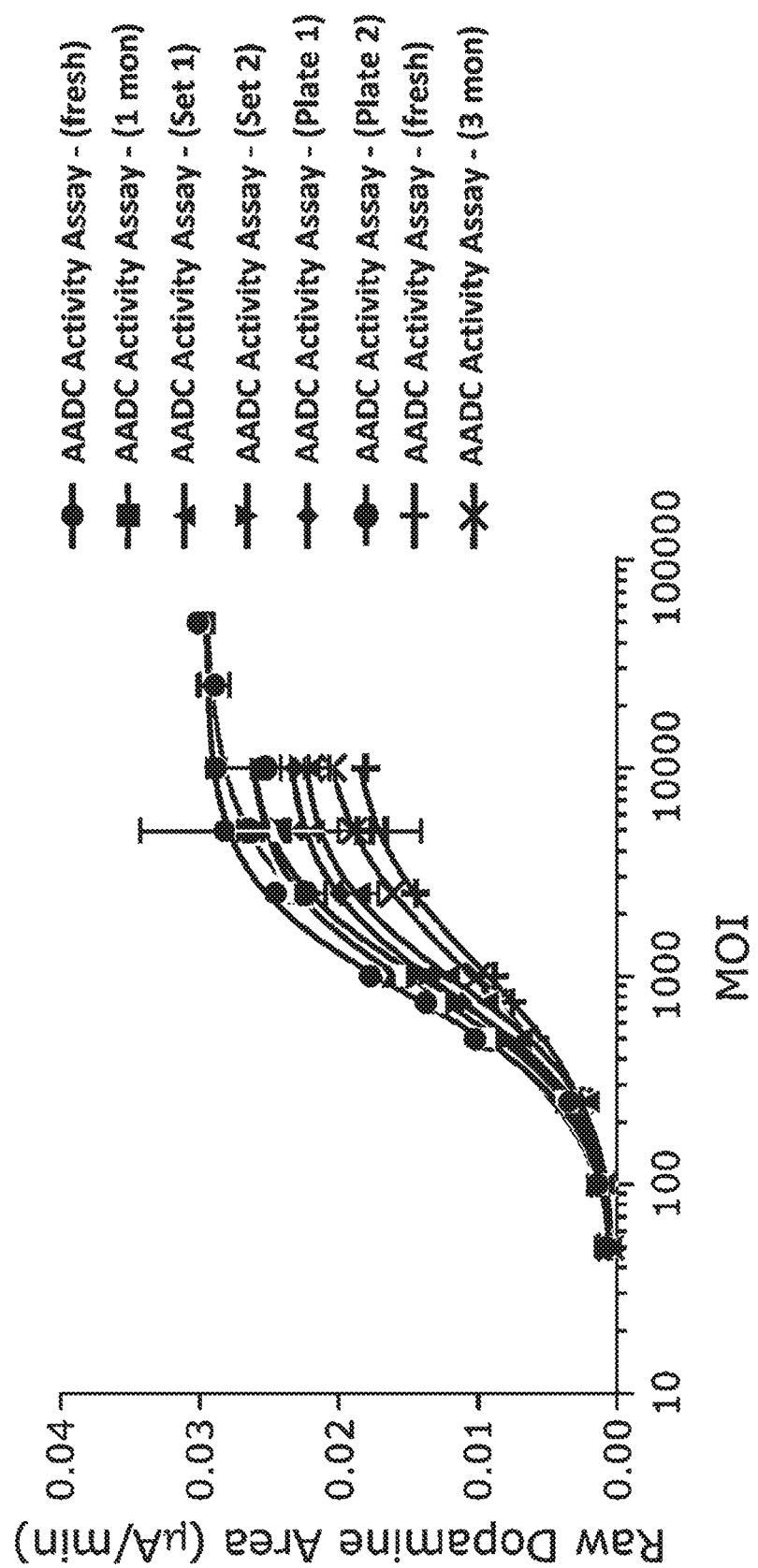
FIG. 3 shows inter-assay variability of the analysis of the reference standard AAV2.AADC.

Four-Parameter Curve Fit Data for the Curves in FIG. 3

| Sample | Bottom | Hillslope | Top | $EC_{50}$ | $logEC_{50}$ |
|---|---|---|---|---|---|
| AADC Activity Assay (fresh) | 0.00009 | 1.540 | 0.02957 | 802.8 | 2.905 |
| AADC Activity Assay (1 mon) | −0.00045 | 1.251 | 0.02959 | 890.2 | 2.949 |
| AADC Activity Assay (Set 1) | 0.00016 | 1.565 | 0.02286 | 936.6 | 2.972 |
| AADC Activity Assay (Set 2) | 0.00017 | 1.540 | 0.02684 | 929.1 | 2.968 |
| AADC Activity Assay (Plate 1) | 0.00015 | 1.492 | 0.02392 | 831.7 | 2.920 |
| AADC Activity Assay (Plate 2) | 0.00031 | 1.619 | 0.02650 | 812.6 | 2.910 |
| AADC Activity Assay (fresh) | 0.00008 | 1.276 | 0.01954 | 1087 | 3.036 |
| AADC Activity Assay (3 mon) | −0.00015 | 1.201 | 0.02186 | 1061 | 3.026 |
| Mean | −0.123 | 1.434 | 11.41 | 918.5 | 2.961 |
| Standard Deviation | 0.108 | 0.1641 | 2.607 | 109.9 | 0.05081 |
| Coefficient of Variation | 523.03% | 11.48% | 14.53% | 11.78% | |

As shown in Table 11, when comparing fit parameter variability, the Top and Bottom baseline values are the most variable. The amount of dopamine generated from the AADC reactions varied.

Examination of AADC Potency Assay Variability Related to Quenching

A potential source of variability is the timing around the quenching of the enzymatic reaction. The reaction in Example 4 occurs at 37° C. for 30 minutes and is quenched using ice-cold perchloric acid (PCA). If the reaction continues at room temperature, then the wells at the bottom of a plate may have more dopamine generation than the wells at the top of the plate (given a top to bottom quenching pattern).

Figure 4A:
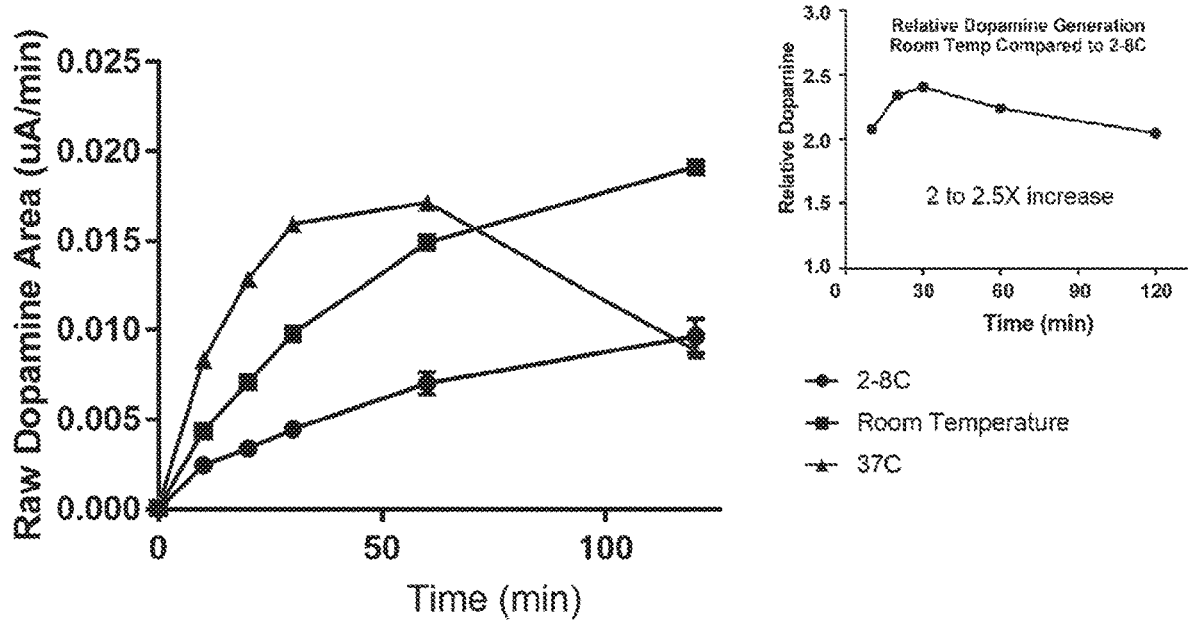
FIG. 4A-4C demonstrating: (4A) the kinetics of dopamine production at three different temperatures (inset is the relative dopamine generation at room temperature compared to 2-8° C.), (4B) an enzyme assay for AAV2.AADC showing less variability of the top baseline, and (4C) use of the enzyme assay in showing the comparability of AADC activity in AADC viral AAV vector produced in HEK293/triple-transfected mammalian cells and AADC viral AAV vector produced in Sf9/baculovirus insect cells.

The rate of dopamine generation was examined at three different temperatures (37° C., room temperature, and 2-8° C.). From the data shown in FIG. 4A, the enzymatic conversion of L-DOPA to dopamine is the slowed when the reaction is held at 2-8° C. as compared to 37° C. or room temperature. The amount of dopamine that is generated at room temperature is roughly 2-2.5 fold greater than the amount of dopamine generated at 2-8° C. (FIG. 4A). These data indicate that the transfer of the plates to 2-8° C. after the 30 minute incubation would significantly reduce the rate of conversion, thereby minimizing the variation between samples while PCA is being added to the wells. Variation can be further minimized through the use of a multi-channel pipette (or 96-well plate pipette) to expedite sample quenching and reduce variation in incubation time. Aligning the methods for the quenching of the wells (halting of the reaction) to the addition of the L-DOPA (initiation of the reaction) reduces the variation in incubation times from row to row across the plate.

To determine if these modifications resulted in decreased variability between samples, cells were transduced in replicate with 10 MOIs, incubated for 30 minutes at 37° C., and then cooled to 2-8° C. using a Bio-Rad Cooling Block (stored upside down in a −20±5° C. freezer) to slow the reaction before quenching. The plates containing the cells were placed on ice and then quenched with ice-cold PCA using an electronic multichannel pipette to control timing and expedite quenching. The application of these modifications greatly reduced the variability in the top slope (FIG. 4B and Table 12):

TABLE 12

Figure 4B:
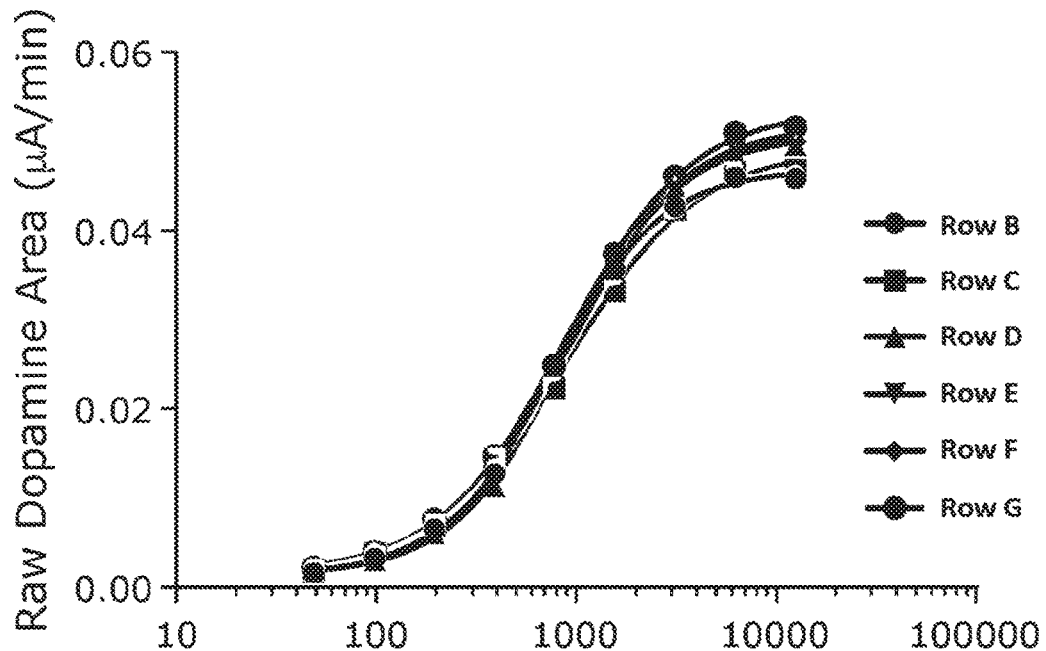
Figure 4C:
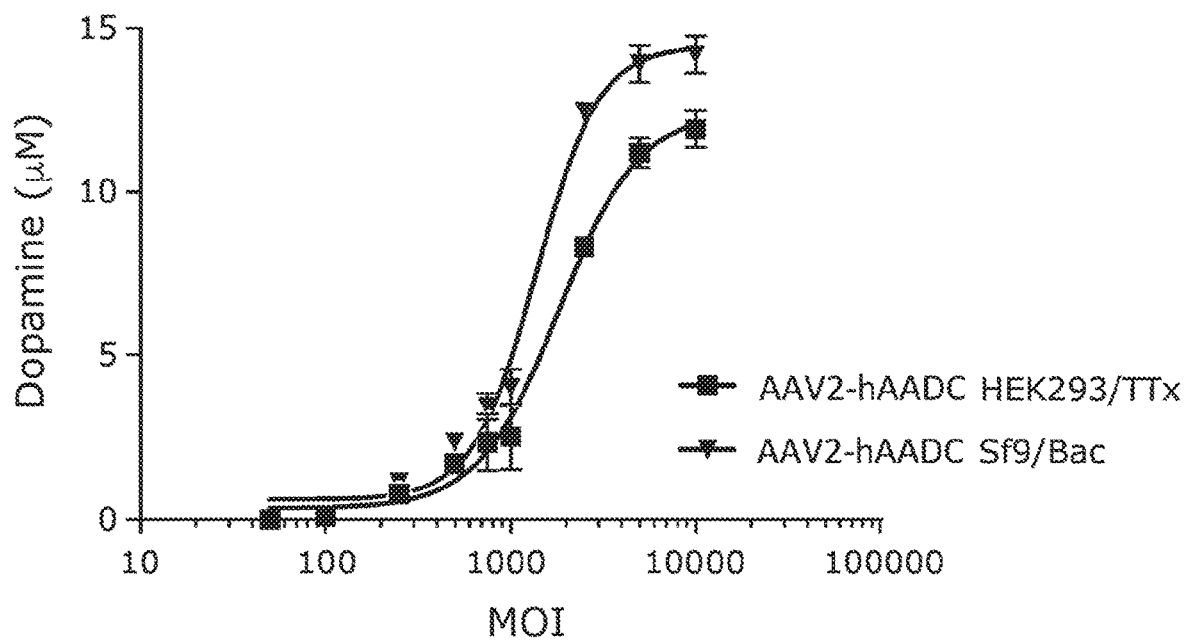

Four-Parameter Curve Fit Data for the Curves in FIG. 4B

| Sample | Bottom | Hillslope | Top | $EC_{50}$ |
|---|---|---|---|---|
| Row B | 0.00138 | 1.595 | 0.04691 | 761.2 |
| Row C | 0.00121 | 1.311 | 0.04922 | 891.5 |
| Row D | 0.00134 | 1.554 | 0.05067 | 890.3 |
| Row E | 0.00134 | 1.457 | 0.05134 | 848.0 |
| Row F | 0.00148 | 1.495 | 0.05181 | 907.9 |
| Row G | 0.00155 | 1.384 | 0.05358 | 880.6 |
| Mean | 0.00138 | 1.466 | 0.05059 | 863.3 |
| Std Dev | 0.00012 | 0.1059 | 0.00230 | 53.8 |
| Coeff of Variation | 8.60% | 7.22% | 4.54% | 6.23% |

Additionally, the doses were more evenly spaced by performing 2-fold serial dilutions of the highest dose. This plate was quenched sequentially from Row B through Row G. There is an upward trend at the highest MOI which contributes to the variation in the top baseline. Each of the rows represent an individually diluted sample rather than using the same serial dilutions for each row. The results presented here show much less variability between the samples than in FIG. 3.

Example 5. AADC Potency/Expression Assay—ELISA—A

HT-1080 Cells are cultured, seeded, diluted, transduced and lysed according to the procedures presented in Example 3.

Preparation of Reagents

Wash/Dilution buffer (1×TBS-T)—Purified water (950 mL) is combined with 50 mL of 20×TBS-T (tris buffered saline+tween, pH 7.4) in a 500 mL graduated cylinder. The process is repeated until 6 L is prepared for wash and dilution.

Blocking Solution (TBS-T with 2% BSA)—1×TBS-T (100 mL) was measured with a graduated cylinder and transferred to a beaker with a magnetic stir bar. 2 g Bovine Serum Albumin (BSA) was added slowly to the solution while stirring. The resulting solution is stored at 4° C., protected from light (up to 2 weeks).

Sample Dilution Buffer (TBS-T with 0.1% BSA)—75 mL of 1×TBS-T is combined with 25 mL the Blocking Solution (TBS-T with 2% BSA). The resulting solution is stored at 4° C., protected from light (up to 2 weeks).

Prepare AADC ELISA Plates with Capture Antibody

Capture Antibody Solution is prepared by combining 10 mL of 50 mM Carbonate Buffer (1 carbonate capsule per 100 mL of autoclaved water) with 0.01 mL of Stock Capture Antibody (2 µg/mL working concentration). Additional Capture Antibody Solution can be produced as need using the same mixture concentrations (10 mL of capture antibody solution for each ELISA plate, with one ELISA assay plate required for each two Test Article samples).

100 µL of diluted capture antibody is added to each well of the ELISA plates (Nunc Maxisorp White Flat Bottom Plates). Plates are sealed and stored overnight. (12-18h) at 2-8° C.

ELISA assay plates are washed three times with 300 µL TBS-T. 300 µL of Blocking Buffer is added to each well of the assay plates using a multichannel pipette. Plates are sealed and incubate on benchtop at room temperature for at least 1 hour. A dilution plate 96-well PCR plate) is prepared by adding Sample Dilution Buffer in the following configuration (Table 13)

TABLE 13

Dilution Plate Setup-Volumes of Sample Dilution Buffer shown in µL

|   | 1 | 2 | 3 | 4 | 5 | 6 | 7 | 8 | 9 | 10 | 11 | 12 |
|---|---|---|---|---|---|---|---|---|---|----|----|----|
| A | Empty | Empty | Empty | 285 | 285 | 285 | 285 | 285 | 285 | 285 | 285 | 285 Sample 1 |
| B | 150 | 150 | Empty | 150 | 150 | 150 | 150 | 150 | 150 | 150 | 150 | 150 |
| C | 150 | 150 | Empty | 150 | 150 | 150 | 150 | 150 | 150 | 150 | 150 | 150 |
| D | 150 | 150 | Empty | 150 | 150 | 150 | 150 | 150 | 150 | 150 | 150 | 150 |
| E | 150 | 150 | Empty | 285 | 285 | 285 | 285 | 285 | 285 | 285 | 285 | 285 Sample 2 |
| F | 150 | 150 | Empty | 150 | 150 | 150 | 150 | 150 | 150 | 150 | 150 | 150 |
| G | 150 | 150 | Empty | 150 | 150 | 150 | 150 | 150 | 150 | 150 | 150 | 150 |
| H | 150 | 150 | Empty | 150 | 150 | 150 | 150 | 150 | 150 | 150 | 150 | 150 |

15 µL of the clarified lysates are added to the 96-well PCR Sample Dilution Buffer plate and serially diluted according to Table 14.

TABLE 14

Serial Dilution of Sample Plate

|   | 1 | 2 | 3 | 4 | 5 | 6 | 7 | 8 | 9 | 10 | 11 | 12 |
|---|---|---|---|---|---|---|---|---|---|----|----|----|
|   | AADC Standard | | | MOI EC70 | | | MOI EC50 | | | MOI EC30 | | |
| A | AADC 50 | AADC 50 | EMPTY | MOI EC70 1:20 | MOI EC70 1:20 | MOI EC70 1:20 | MOI EC50 1:20 | MOI EC50 1:20 | MOI EC50 1:20 | MOI EC30 1:20 | MOI EC30 1:20 | MOI EC30 1:20 Sample 1 |
| B | AADC 25 | AADC 25 | | MOI EC70 1:40 | MOI EC70 1:40 | MOI EC70 1:40 | MOI EC50 1:40 | MOI EC50 1:40 | MOI EC50 1:40 | MOI EC30 1:40 | MOI EC30 1:40 | MOI EC30 1:40 |
| C | AADC 12.5 | AADC 12.5 | | MOI EC70 1:80 | MOI EC70 1:80 | MOI EC70 1:80 | MOI EC50 1:80 | MOI EC50 1:80 | MOI EC50 1:80 | MOI EC30 1:80 | MOI EC30 1:80 | MOI EC30 1:80 |
| D | AADC 6.25 | AADC 6.25 | | MOI BC70 1:160 | MOI EC70 1:160 | MOI EC70 1:160 | MOI EC50 1:160 | MOI EC50 1:160 | MOI EC50 1:160 | MOI EC30 1:160 | MOI EC30 1:160 | MOI EC30 1:160 |
| E | AADC 3.125 | AADC 3.125 | | MOI EC70 1:20 | MOI EC70 1:20 | MOI EC70 1:20 | MOI EC50 1:20 | MOI EC50 1:20 | MOI EC50 1:20 | MOI EC30 1:20 | MOI EC30 1:20 | MOI EC30 1:20 Sample 2 |
| F | AADC 1.563 | AADC 1.563 | | MOI EC70 1:40 | MOI EC70 1:40 | MOI EC70 1:40 | MOJ EC50 1:40 | MOI EC50 1:40 | MOI EC50 1:40 | MOI EC30 1:40 | MOI EC30 1:40 | MOI EC30 1:40 |
| G | AADC 0.781 | AADC 0.781 | | MOI EC70 1:80 | MOI EC70 1:80 | MOI EC70 1:80 | MOI EC50 1:80 | MOI EC50 1:80 | MOI EC50 1:80 | MOI EC30 1:80 | MOI EC30 1:80 | MOI EC30 1:80 |
| H | Neg | Neg | | MOI EC70 1:160 | MOI EC70 1:160 | MOI EC70 1:160 | MOI EC50 1:160 | MOI EC50 1:160 | MOI EC50 1:160 | MOI EC30 1:160 | MOI EC30 1:160 | MOI EC30 1:160 |

The plate is sealed and shaken at 400 rpm for 2 hours at room temperature. 100 µL of Detection Antibody Solution is added to each well using a multichannel pipette. The plate is sealed and shaken at 400 rpm for 1 hour at room temperature, and then protected from light using aluminum foil.

Chemiluminescence

For each assay plate, prepare 10 mL of Luminescence; Solution is prepared for each sample plate by mixing 5 mL of Luminol/Enhancer with 5 mL of Peroxide Solution in a 15 mL conical tube using a SuperSignal West Dura Extended Duration Substrate kit.

100 µL of Luminescence Solution is added to each well (one plate at a time) using a multichannel pipette (left to right). The plate is sealed, protected with aluminum foil, and shaken at 400 rpm for 1 minute. Chemiluminescence is captured using a SpectraMax M5 or similar plate reader using the luminescence setting.

Data Analysis

Raw data is analyzed using SpectraMax M5 software or similar software as follows (with reference to the plate layout in Table 14): (i) Wells H1 and H2 are averaged to get a negative ELISA control; (ii) The negative ELISA control is subtracted from all wells in the plate; (iii) The standard curve that is fit is used to normalize the data from chemiluminescence signal to AADC (ng/mL); (iv) Each test well is adjusted by the appropriate dilution factor (1:20, 1:40, 1:80, or 1:160); (v) The dilutions from each transduced cell culture well are averaged. (vi) The three replicates from each sample MOI are averaged and the standard deviation is determined; (vii) Any values that do not fall within the standard curve range are excluded, and the remaining values are averaged by adjusting the range used for the average and standard deviation in the template (or reported as a single value if only one out of three values are valid).

Data analysis will provide the following: (i) The Four Parameter Fit data for the AADC standard curve; (ii) The correlation coefficient for the standard curve: (iii) The average AADC concentration at each MOI; (iii) The standard deviation of the average relative AADC concentration; and (iv) The average relative AADC concentration of each MOI compared to that MOI of the Reference Standard, according to the following equation:

$$\text{Relative } AADC \text{ Concentration} = 100\% \times \frac{\text{Test article } AADC \text{ Concentration}}{\text{Reference Standard } AADC \text{ Concentration}}$$

Example 6. AADC Potency/Expression Assay—ELISA—B

Preparation of Reagents

Trypsin-EDTA—A 100 mL bottle of Trypsin-EDTA was thawed at 2-8° C. overnight. Once the bottle was completely thawed, 10 mL of solution was transferred to multiple 15 mL polypropylene, sterile, centrifuge tubes. Aliquots were stored at −15 to −30° C. Aliquots were thawed and equilibrated to ambient temperature prior to use. Once thawed, the aliquots were stored at 2-8° C. and assigned a two-week expiration date.

Penicillin-Streptomycin (Pen-Strep) Solution—A 100 mL bottle of Penicillin-Streptomycin was thawed at 2-8° C. overnight. 6 mL of thawed solution was transferred to multiple polypropylene, sterile, centrifuge tubes, and then stored at −15 to −30° C.

Cell Culture Media (CCM) (EMEM, 10% FBS. 1% Pen-Strep)—5.6 mL of Pen-Strep solution was added to a 500 mL bottle of Eagle's Minimal Essential Medium (EMEM). 5.6 mL of fetal bovine serum (FBS) was then added to the bottle of EMEM+Pen-Strep. The resulting CCM solution was passed through a 0.22 µm sterile disposable filter into a sterile receiver bottle and stored at 2-8° C. (protected from light).

Cell Lysis buffer without protease inhibitor (0.1 M sodium phosphate, 0.2% Triton X-100, pH 7.8)—Purified water (400 mL) was added to a 500 mL graduated cylinder, the water was transferred to a IL beaker with magnetic stir bar. Stirring was begun on a stir plate. Sodium phosphate monobasic (0.25 g) and sodium phosphate dibasic (3.24 g) were mixed with the water until dissolved. 1 g of Triton X-100 was poured into the stirring solution. The solution was stirred for 30 minutes at room temperature. The pH was tested, and if the solution was not pH 7.7-7.9, then the pH was adjusted with 0.1N HCl or 0.1N NaOH as needed. The contents of the beaker were transferred to a graduated cylinder and filled to volume of 500 mL with Milli-QV® water. The solution was passed through a 0.22 µm sterile disposable filter into a sterile receiver bottle. The bottle was wrapped in aluminum foil to protect it from light and stored at room temperature.

AADC ELISA coating buffer (carbonate buffer solution)—The carbonate buffer was provided as gelatin capsules. The contents of two capsules were emptied in 200 mL of purified water in a clean, sterile beaker, and a magnetic stir bar was added. The contents were dissolved completely. The solution was passed through a 0.22 µm sterile disposable filter into a sterile receiver bottle. The bottle was labeled with an expiration date of 1 month for the date of preparation and stored at room temperature.

ELISA Wash buffer (1×TBS-T)—Purified water (1800 mL) was measured into a 2 L graduated cylinder, and 200 mL of 10×TBS-T (tris buffered saline+tween, pH 7.4) solution was measured in a 500 mL graduated cylinder. 10×TBS-T was added to the water, and the cylinder was covered with parafilm. The cylinder was inverted 2-3 times to mix. The solution was passed through a 0.22 µm sterile disposable filter into a sterile receiver bottle and stored at room temperature.

ELISA blocking buffer (TBS-T with 2% BSA)—1× TBS-T (80 mL) was measured with a graduated cylinder and transferred to a beaker with a magnetic stir bar. 2 g Bovine Serum Albumin (BSA) was added slowly to the buffer while stirring for less than thirty minutes at room temperature. The beaker was adjusted to a final 100 mL volume with 1×TBS-T. The solution was transferred to a clean, sterile bottle and stored at 2-8° C.

Detection Antibody Dilution Buffer (TBS-T with 0.5% BSA)—1× ELISA wash buffer (100 mL) was measured with a graduated cylinder. The buffer was transferred to a beaker with a magnetic stir bar. 0.5 g of BSA was added to the buffer while stirring for up to 30 minutes at room temperature. The solution was transferred to a clean, sterile bottle and stored at 2-8° C.

ELISA Sample Dilution Buffer (TBS-T with 0.1% BSA)—ELISA wash buffer (100 mL) was measured with a graduated cylinder. The buffer was transferred to a beaker with a magnetic stir bar. 0.1 g of BSA was slowly added to the buffer while stirring for up to 30 minutes at room temperature. The solution was transferred to a clean, sterile bottle and stored at 2-8° C.

AADC ELISA Standard—A lyophilized solid was dissolved with 1 mL of ELISA dilution buffer (TBS-T with 0.5% BSA and vortexed for 5 to 10 seconds to mix. The liquid was allowed to drain to the bottom of the vial for 1-2 minutes. The AADC Standard was aliquoted into 80 µL volumes in 0.5 mL volume microcentrifuge tubes and stored at less than −70° C.

Preparation of Cell Suspension of HT-1080 Cells

The cell suspension was prepared with the seeding density of $7.5 \times 10^4$ cells/well. Alternatively, 100 µL of HT-1080 was plated in DMEM+10% FBS at a density of $5 \times 10'$ cells/well in a 96-well plate. A P300 multichannel pipette was used for this step to avoid shearing the HT-1080 cells. The plates were sealed with porous adhesive film to reduce evaporation and maintain uniformity of gas exchange across plate area, and a lid was placed on top of plate. The cells were incubated at $37 \pm 2°$ C. for $24 \pm 2$ hours. One confluent 175 flask of HT-1080 cells will have roughly $2 \times 10^6$ cells, enough cells for four to five 24 well plates. The complete culture media (CCM). 1×HBSS, and Trypsin-EDTA were warmed in a 37° C. water bath for at least 10 minutes. The media was aspirated from the confluent HT1080 monolayer into a 1:2 bleach solution. The cells were washed by adding 10 mL of 1×HBSS to the flask using a serological pipette. The flask was rocked back and forth to rinse the cells. The HBSS was aspirated into a 1:2 bleach solution. Using a sterile 5 mL serological pipette, 4 mL Trypsin-EDTA was added to the flask. The flask was rocked gently to allow the trypsin to cover the entire bottom of the flask. The flask was incubated for 4-5 minutes in a $37 \pm 2°$ C. with 4-6% $CO_2$ incubator.

The flask was examined under the microscope to confirm that the cells were detached from the flask. The bottom of the flask appeared clear with the cells floating freely in the CCM. Cell detachment was not forced. But once cells detached, trypsin was removed. Once cells were detached from the bottom of the flask, using a 10 mL serological pipette, 8 mL of CCM (warmed to room temperature) was added to block trypsin activity. The flask was rocked back and forth to dislodge remaining adhering cells. The cell suspension was transferred to a sterile 50 mL conical centrifuge tube, and the tube was centrifuged at 400×g for 5 minutes at ambient temperature. The cells formed a pellet at the bottom of the 50 mL sterile centrifuge tube. Working in the biosafety cabinet, as much of the CCM as possible without disturbing the pellet was aspirated to rid the cell suspension of Trypsin-EDTA. Fresh, prewarmed CCM (12 mL) was added to the tube, and CCM was pipetted up and down to break apart the cell pellet. The final suspension had a uniform density and no clumps of cells. The cell suspension was counted.

The HT-1080 cells were diluted 1:2 in a tube by adding 100 µL of cell suspension and 100 µL trypan blue stain to the tube, which were mixed together gently by vortexing. The surface of the hemocytometer was cleaned with 70% alcohol solution and dried with KIMWIPES™ (Kimberly-Clark). A cover slip was positioned over the grooves of the hemocytometer. A 20 µL single channel pipette was used to load 10 µL of the trypan blue stained cell suspension into each of the counting chambers of the hemocytometer. The inverted phase contrast microscope was used to count the number of cells in each of five squares on the two grids of the hemocytometer (10 squares total). If there are more than 100 cells counted in each square, the dilution of cell suspension was increased in trypan blue, and counting was repeated. There should be greater than 30 cells in each square. To count the number of cells in the suspension using a hemocytometer, the cell concentration (cells/mL) was calculated according to the following equations:

$$\text{Cells/mL} = (\text{Total cells} \div 10) \times \text{Dilution factor with trypan blue} \times 10{,}000$$

"10,000" is the volume correction factor for the hemocytometer

One 24-well plate was prepared for each sample being tested, and a separate plate was prepared for the assay control. The cells were diluted with CCM to $7.5 \times 10^4$ cells/mL using the following equations.

$$\text{Dilution Factor} = (\text{Measured cells/mL}) / (7.5 \times 10^4 \text{ cells/mL})$$

$$\text{Required Volume (mL) of cell suspension} = \text{number of assay wells} \times 1 \text{ mL/well} / \text{dilution factor}$$

$$\text{Required Volume (mL) of } CCM \text{ diluent} = \text{number of assay wells} - \text{required volume of cell suspension}$$

After dilution, the cell suspension was plated. All the wells of a 24-well plate were seeded with 1 mL of cell suspension. The cells were dispersed by holding the plate in contact with the incubator shelf and moving it left and right 3-4 times then forward and backward 3-4 times. The cells were incubated 18-24 hours at $37 \pm 2°$ C. and $5 \pm 1\%$ $CO_2$.

Transduction of HT1080 Cells

At the end of the incubation period for preparation of the cell suspension, the CCM, 1×HBSS, and Trypsin-EDTA were warmed in a 37° C. water bath for at least 10 minutes. The medium was aspirated from one 'count' well on each assay plate and washed with HBSS. Trypsin (100 µL) was added to each washed well and incubated at $37 \pm 2°$ C. to detach the cells from the surface. The activity of trypsin was stopped by adding 100 µL of CCM to the wells.

The cell density of the trypsin-treated well was determined using a hemocytometer to ensure each square contained at least 10 cells. The infection protocol was continued if the cells were between $1 \times 10^5$ and $3 \times 10^5$ cells/well.

For each sample to be analyzed, the viral genome (vg) titer was greater than $1 \times 10^{11}$ vg/mL. The concentration of the AAV2.AADC reference standard (LN-2014-088-56; 10 mM sodium phosphate, 350 mM NaCl, 0.001% pluronic) was $3.90 \times 10^{12}$ vg/ml. The target concentration (vg/mL) was calculated for the initial dilution of the AAV2.AADC reference standard (LN-2014-088-56) and the test sample virus to result a multiplicity of infection (MOI) of 1,000 vg/cell using the following formula:

$$\text{Target concentration (vg/mL)} = \text{Cell count/well} \times 2 \times 10^4$$

The $2 \times 10^4$ value also included a correction factor for the sample dilutions and the amount of volume delivered to the well, in addition to the 1,000 MOI.

Alternatively, an aliquot of the AAV2.AADC Reference Standard (LN-2014-088-56) and the test sample was completely thawed or an unexpired aliquot stored at 2-8° C. was used. If the Reference Standard or test sample titer was greater than or equal to $1 \times 10^{11}$ vg/mL, an initial dilution of the test material was performed in 1×PBS.

The volume of test sample and Reference Standard that was needed to prepare 1 mL of the 1,000 vg/cell target concentration was calculated using the formula:

Volume of test sample or ref. standard=(Target concentration×Total volume)/(Test sample or ref.control titer)

The vector dilutions described in Table 15 were prepared in a sterile 2 mL deep-well 96-well plate. Each dilution was prepared in triplicate. The serial dilution was performed using the same tip, but different tips were used between replicates. The final 50 µL was discarded at the end to ensure the final volume in each well is 100 µL.

TABLE 15

Vector dilutions

| Target MOI (vg/cell) | Volume of diluted AAV test sample or Reference Standard (µL) | Volume 1 × PBS (µL) |
|---|---|---|
| 1,000 | 100 µL of 1,000 MOI | 0 |
| 500 | 100 µL of 1,000 MOI | 100 |
| 250 | 100 µL of 500 MOI | 100 |
| 125 | 100 µL of 250 MOI | 100 |
| 63 | 100 µL of 125 MOI | 100 |
| Neg. | NA | 100 |

Each vector dilution was added to 600 µL of Cell Culture Media (CCM) and vortexed 2-3 seconds to mix. The mixture was stored at room temperature. These dilutions were used within two hours of preparation. Three extra samples of 100 µL of 1×PBS and 600 µL of CCM were prepared as negative controls. The media was aspirated from the wells one plate at a time, and the media in the wells was replaced with 350 µL of CCM-diluted reference standard and test samples. The plates were covered and returned to the 37±2° C. and 5±1% $CO_2$ incubator for 22-26 hours. At the end of the incubation period, a bottle of CCM was warmed for at least 10 minutes in a 37±2° C. water bath. The infection medium was aspirated and replace with 1 mL of prewarmed CCM per well. The plates were covered and returned to the 37±2° C. and 5±1% $CO_2$ incubator for 46-50 hours.

Cell lysis buffer was prepared for harvesting of the cells. For each plate, 58 µL of 100×HALT protease inhibitor was added to 5.7 mL of the cell lysis buffer. Working with one plate at a time, aspirate the medium in all wells and wash with 1 mL of 1×HBSS. The HBSS was aspirated, and 300 µL of cell lysis buffer was added to each well. The plate was rocked gently by hand for 10-15 seconds to mix, then the plate was covered and frozen at less than or equal to −60° C. for greater than or equal to 1 hour.

Preparing Samples to Detect Expression of AADC Using ELISA

HT-1080 cells are infected with AAV2-AADC. After 3 days, cells were lysed and the amount of AADC protein was quantified using a DDC Matched ELISA Antibody Pair Set, Human (Sino Biological; Catalog number: SEK10560).

Each 24 well infection plate required one 96-well ELISA plate to assay. 10 mL of diluted capture antibody solution was prepared per 96-well plate. The capture antibody was diluted to a final concentration of 2 µg/mL in the AADC ELISA coating buffer. Using a multichannel pipette, 100 µL of diluted capture antibody was added to each well of a solid white opaque MAXISORP™ 96-well plate (Thermo Fisher). The plates were covered with sealing film and stored overnight (12 to 18 hours) at 2-8° C. with an empty plate above and an empty plate below the coated plate.

For blocking the dopa decarboxylase (DDC) ELISA plates, the plates were washed three times with ELISA wash buffer with 300 µL TBS-T using an automated plate washer. Using a multichannel pipette, 300 µL of ELISA Blocking Buffer was added to all wells of the ELISA plates. The plates were covered with a plate sealer and stored at room temperature for 75±15 minutes (at least one hour).

Cells lysate dilutions were prepared by thawing the 24-well plates at ambient temperature. One at a time, the plates were floated in a room temperature sonicating water bath and sonicated for 30 seconds. The plates were tipped at an angle so that the lysate was collected at the bottom edge of the well. A P1000 pipette was used to transfer the cell lysates to a labeled set of microcentrifuge tubes. The replicated wells were transferred with a single tip but a tip was changed when pipetting samples from cells infected at different MOI. The cell debris was pelleted by centrifugation at 10,000 RPM for 5 minutes at room temperature. The clarified lysate was transferred to a second set of labeled microcentrifuge tubes.

The ELISA template was prepared by thawing an aliquot of the AADC standard stock. The AADC standard stock was diluted with Sample Dilution Buffer to 50 ng/mL. Each plate required 400 µL of 50 ng/mL AADC standard. The template plate was prepared using a low-binding 96-well plate. The template contained three dilutions of each clarified lysate sample and the AADC standard prepared using the ELISA Sample Dilution Buffer. Lysate sample dilutions were 1:20, 1:40, and 1:80.

Conducting ELISA to Detect Expression of AADC

ADDC Matched ELISA Antibody Pair Set, Human (Sino Biological; Catalog number; SEK10560) was used to perform ELISA to confirm expression of AADC in the same lysate to be used in the AADC potency assay described herein. The 96-well ELISA plates were washed three times with TBS-T using the automated plate washer. The plates were inverted and tapped onto a stack of paper towels to drain the residual liquid.

A multichannel pipette fitted with 12 tips was used to aspirate 100 µL of samples and standards to dispense into the corresponding row in the 96-well ELISA plates. Pipette tips were changed for each row. Plates were covered with sealing film and agitated at 200 rpm on an orbital shaker at ambient temperature for 2 hours±15 minutes. For each plate, 10 mL of diluted detection antibody solution was prepared at a final concentration of 0.2 µg/mL.

The 96-well ELISA plates were washed three times with TBS-T using the automated plate washer. The plates were inverted and tapped onto a stack of paper towels to drain the residual liquid. 100 µL of diluted detection antibody solution was added to each well. The plates were covered with sealing film and agitated at 200 rpm on an orbital shaker at ambient temperature for 1 hour±10 minutes.

For each assay plate, 10 mL of the SUPERSIGNAL™ ELISA Pico Chemiluminescent Substrate (Thermo Fisher) was prepared by combining 5 mL of the Luminol/Enhancer with 5 mL of the Horseradish Peroxide Solution. The 96-well ELISA plates were washed three times with TBS-T using the automated plate washer. The plate were inverted and tapped onto a stack of paper towels to drain the residual liquid. 100 L of the SUPERSIGNAL™ ELISA Pico Chemiluminescent Substrate (Thermo Fisher) was added to each well of the plate with a multichannel pipette (left to right) immediately before detection. The solution was added to one plate at a time as the incubation time is short. The plate was agitated on an orbital shaker at 200 rpm for 2±1 minute at ambient temperature.

The plates were read between 2 and 10 minutes after addition of the substrate using the AMQ-021 VERSA-MAX™ Microplate Reader (Molecular Devices LLC). The plate reader reads the luminescence of the ELISA plate and calculates an average blank. The blank is subtracted from all wells and the standards are fit to a four-parameter curve. The test sample concentrations are interpolated off of the standard curve to determine the AADC concentration.

Concentrations within the readable range of the curve are multiplied by the dilution factor, and the dilution-corrected results from MOIs in the readable range are average to obtain the reportable result. Other calculations may be performed as appropriate from the test data. Calculations used in testing will be documented in the final report.

The analysis template from SOFTMAX® Pro software (Molecular Devices LLC) on the VERSAMAX™ Microplate Reader (Molecular Devices LLC) averaged the blank luminescence values and subtracted the average blank luminescence from all wells. The background corrected intensity values were plotted for the AADC Standards vs. the Standard concentrations. A four-parameter logistic regression was performed on the standard points. The regression equation and the background corrected intensity values were used to calculate the concentration of AADC in all wells of the plate.

A dilution corrected concentration for all wells within the readable range of the standard curve was calculated by multiplying the well result by the dilution factor. Wells with calculated AADC concentrations outside of the standard curve range (0.39-25 ng/mL) were excluded. The dilution corrected AADC concentrations from the biological replicates were averaged. Standard deviations and % CV were determined. Dilutions with a % CV greater than 100 were excluded from the analysis.

All valid results from MOI were averaged to get the MOI result. The dilution-corrected result of all samples within the readable range of the standard curve was averaged at each MOI, and a relative potency was determined by dividing the test sample average by the reference control average at each MOI. The MOI result of the test sample was divided by the MOI result of the Reference Standard at each MOI to calculate the relative MOI potency. The average of the relative MOI potencies was calculated to determine the reportable relative potency.

The upper limit of quantification of the MOI is 4000 ng/mL. The lower limit of quantification of the MOI is 7 ng/mL. The AADC ELISA standard regression line must have a $R^2$ correlation coefficient of greater than or equal to 0.98. The average luminescence of the ELISA blank was less than or equal to 10,000 for use in the calculation. The percent CV of the luminescence between triplicate infection wells at a single dilution was less than or equal to 100 for use in the calculation the results at that dilution to be valid. At least 1 valid dilution result was needed at each MOI for the Reference Standard. Invalid assays were repeated. The reported AADC concentration of the uninfected lysates (0 MOI) at the 1:20 dilution of the 0 MOI sample was undetected in valid assays.

What is claimed:

1. A method for measuring aromatic L-amino acid decarboxylase (AADC) viral vector potency, comprising:
   (a) providing an adeno-associated virus (AAV) formulation comprising an AADC viral vector, wherein the AADC viral vector is an AAV that comprises a polynucleotide encoding one or more AADC polypeptides;
   (b) contacting the AAV formulation with a cell under conditions that result in the cell producing one or more AADC polypeptides from the polynucleotide;
   (c) lysing the cell to form a first cell lysate comprising at least a portion of the AADC polypeptides;
   (d) determining the potency of the AADC viral vector by:
      (i) adding L-3,4 dihydroxyphenylalanine (L-DOPA) to the first cell lysate under conditions that allow at least a portion of the AADC polypeptides in the first cell lysate to react with at least a portion of the L-DOPA to produce dopamine;
      (ii) measuring the amount of dopamine in the first cell lysate after the reaction between the AADC polypeptides and the L-DOPA;
      (iii) providing an AADC viral vector reference standard for dopamine production, wherein the AADC viral vector reference standard comprises a polynucleotide encoding one or more AADC polypeptides, and wherein the amount of dopamine produced by the AADC viral vector reference standard is determined by:
         adding L-DOPA to a second cell lysate that comprises at least a portion of the AADC polypeptides, wherein the AADC polypeptides in the second cell lysate are produced by cells transduced with the AADC viral vector reference standard; and
         measuring the amount of dopamine produced in the second cell lysate after the reaction between the AADC polypeptides and the L-DOPA; and
      (iv) comparing the amount of dopamine produced using the AADC viral vector to the AADC viral vector reference standard, such that an AADC Relative Potency of the AADC viral vector is measured.

2. The method of claim 1, wherein the cells are HT1080 cells.

3. The method of claim 2, wherein the HT1080 cells are plated at a density of between $7 \times 10^3$ to $4 \times 10^4$ cells/well, or between $9 \times 10^3$ to $2 \times 10^4$ cells/well.

4. The method of claim 1, wherein the cells are harvested after 18-30 hours post transduction, or after 22-26 hours post transduction.

5. The method claim 1, wherein the AADC viral vector is transduced b into the cells at a concentration of 1 vector genome (vg)/cell to $1\times10^8$ vg/cell, or 10 vg/cell to $1\times10^5$ vg/cell.

6. The method of claim 1, wherein the cells are lysed using chemical lysis, mechanical lysis, or a combination thereof.

7. The method of claim 6, wherein the lysis comprises spinning the cells in a centrifuge at 3650-3800 RPM for 5-20 minutes at room temperature.

8. The method of claim 1, wherein an AADC reaction buffer is added to the first and/or second cell lysate, and wherein the AADC reaction buffer comprises octanesulfonic acid sodium salt, sodium phosphate monobasic, and acetonitrile.

9. The method of claim 8, wherein the AADC reaction buffer comprises 3.0-3.5 mM octanesulfonic acid sodium salt (pH 3.0), 72.5 mM sodium phosphate monobasic ($NaH_2PO_4$), and 10% acetonitrile.

10. The method of claim 1, wherein the concentration of L-DOPA added to the first and/or second cell lysate is 0.01 mM to 1 mM, or 0.03 mM.

11. The method of claim 1, wherein the reaction between AADC polypeptides and L-DOPA is carried out at 37° C.

12. The method of claim 1, wherein the reaction between AADC polypeptides and L-DOPA is carried out for 10-120 minutes, or for 30 minutes.

13. The method of claim 1, wherein the first and/or second cell lysate is exposed to a temperature of 2-8° C. following the AADC reaction with L-DOPA.

14. The method of claim 1, wherein the reaction between AADC polypeptides and L-DOPA is quenched by adding ice-cold perchloric acid.

15. The method of claim 1, wherein the amount of dopamine is measured using Ultra High-Performance Liquid Chromatography with an Electrochemical Detector (UHPLC-ECD) or Ultra High-Performance Liquid Chromatography with an ultraviolet detector (UHPLC-UV).

16. The method of claim 1, wherein the AADC viral vector comprises a polynucleotide comprising at least 85% identity to SEQ ID NO. 2.

17. The method of claim 1, wherein the AADC viral vector comprises an AAV2 capsid.

18. A method of producing a gene therapy product, comprising:
  (a) providing an AAV formulation comprising an AADC viral vector, wherein the AADC viral vector comprises a polynucleotide encoding one or more AADC polypeptides;
  (b) measuring AADC Relative Potency of the AADC viral vector of the AAV formulation using the method of claim 1;
  (c) comparing the AADC Relative Potency to a threshold AADC Relative Potency value; and
  (d) aliquoting the AAV formulation into a formulation container if the AADC Relative Potency is greater than or equal to the threshold AADC Relative Potency value.

19. The method of claim 1, wherein the AADC viral vector has an AADC Relative Potency of 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, 95-100%, 100-105%, 105-110%, 110-115%, 115-120%, 120-125%, 125-130%, 130-135%, 135-140%, 140-145%, 145-150%, 150-155%, 155-160%, 160-165%, 165-170%, 170-175%, 175-180%, 180-185%, 185-190%, 190-195%, or 195-200%.

20. The method of claim 1, wherein the AADC Relative Potency of the AADC viral vector is compared to a threshold AADC Relative Potency value.

* * * * *